US012735506B2

(12) United States Patent
Bailly et al.

(10) Patent No.: US 12,735,506 B2
(45) Date of Patent: Sep. 15, 2026

(54) ARGINASE 1 BINDERS FOR INHIBITING ARGINASE 1 ACTIVITY

(71) Applicant: MERCK SHARP & DOHME LLC, Rahway, NJ (US)

(72) Inventors: Marc Andre Bailly, San Mateo, CA (US); Kalyan Chakravarthy, Woburn, MA (US); Ghassan Najib Fayad, Waban, MA (US); Laurence Fayadat-Dilman, San Carlos, CA (US); Veronica Juan, Redwood City, CA (US); Esther Kofman, San Jose, CA (US); Heping Lin, Wellesley, MA (US); Jennifer E. O'Neil, Dedham, MA (US); Rachel Lynn Palte, Melrose, MA (US); Giovanna Scapin, New York, NY (US); Hussam Hisham Shaheen, Auburn, NH (US); Tao Wang, Cranford, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 609 days.

(21) Appl. No.: 18/253,691

(22) PCT Filed: Nov. 22, 2021

(86) PCT No.: PCT/US2021/060254
§ 371 (c)(1),
(2) Date: May 19, 2023

(87) PCT Pub. No.: WO2022/115350
PCT Pub. Date: Jun. 2, 2022

(65) Prior Publication Data

US 2024/0002533 A1 Jan. 4, 2024

Related U.S. Application Data

(60) Provisional application No. 63/119,260, filed on Nov. 30, 2020.

(51) Int. Cl.
*C07K 16/40* (2006.01)
*A61K 39/00* (2006.01)
*C07K 16/28* (2006.01)

(52) U.S. Cl.
CPC .......... *C07K 16/40* (2013.01); *C07K 16/2818* (2013.01); *C07K 16/2827* (2013.01);
(Continued)

(58) Field of Classification Search
CPC ................ C07K 16/40; C07K 16/2818; C07K 16/2827; C07K 2317/51; C07K 2317/52;
(Continued)

(56) References Cited

U.S. PATENT DOCUMENTS 9,200,011 B2 12/2015 Van Zandt et al.
2014/0363417 A1 12/2014 Cheng et al.

FOREIGN PATENT DOCUMENTS

WO 2016070050 A1 5/2016
WO WO-2017192589 A1 * 11/2017 ......... C07K 16/1018
(Continued)

OTHER PUBLICATIONS

Armour et al., Recombinant Human IgG Molecules Lacking Fcy receptor I Binding and Monocyte Triggering Activities, Eur. J. Immunol., 1999, pp. 2613-2624, 29.
(Continued)

*Primary Examiner* — Scarlett Y Goon
*Assistant Examiner* — Audrey L Buttice
(74) *Attorney, Agent, or Firm* — John David Reilly; John C. Todaro

(57) ABSTRACT

Arginase 1 binders comprising human antibodies and antigen-binding fragments thereof that inhibit the activity of human Arginase 1 (hArg1) are described. These Arginase 1 binders present an alternative mechanism for inhibiting hArg1 activity and highlight the ability to utilize binders as
(Continued)

mAb1 human Arg1 IC50 = 3.3 +/- 0.3 nM
mAb2 human Arg1 IC50 = 5.3 +/- 0.8 nM probes in the discovery and development of peptide and small molecule inhibitors for enzymes in general.

17 Claims, 15 Drawing Sheets

Specification includes a Sequence Listing.

(52) U.S. Cl.
CPC .... *A61K 2039/507* (2013.01); *C07K 2317/51* (2013.01); *C07K 2317/52* (2013.01); *C07K 2317/55* (2013.01); *C07K 2317/565* (2013.01); *C12Y 305/03001* (2013.01)

(58) Field of Classification Search
CPC .......... C07K 2317/55; C07K 2317/565; C07K 2317/21; C07K 2317/24; C07K 2317/35; C07K 2317/71; C07K 2317/76; C07K 2317/92; A61K 2039/507; C12Y 305/03001; A61P 35/00
See application file for complete search history.

(56) References Cited

FOREIGN PATENT DOCUMENTS

| | | | | |
|---|---|---|---|---|
| WO | 2018089490 A1 | | 5/2018 | |
| WO | WO-2020006374 A2 | * | 1/2020 | ............. A61P 35/00 |

OTHER PUBLICATIONS

Ash, David E., Arginine Metabolism: Enzymology, Nutrition, and Clinical Significance—Structure and Function of Arginases, J. Nutr., 2004, 2760S-2764S, 134.
Bronte, Vincenzo et al., L-arginine metabolism in myeloid cells controls T-lymphocyte functions, Trends in Immunology, 2003, 301-305, vol. 24 | No. 6.
Bronte, Vincenzo et al., Tumor-Induced Immune Dysfunctions Caused by Myeloid Suppressor Cells, Journal of Immunotherapy, 2001, 431-446, 24(6).
Cinader, B. et al., Mechanism of Enzyme Inhibition by Antibody—A Study of the Neutralization of Ribonuclease, Immunology, 1964, 342-362, 7.
Cinader, B., Antibodies against enzymes, Rev. Microbiol., 1957, 371-390, 11.
Cox, J. David et al., Arginase-boronic acid complex highlights a physiological role in erectile function, Nature Structural Biology, 1999, 1043-1047, 6(11).
Dahms, Sven O. et al., The structure of a furin-antibody complex explains non-competitive inhibition by steric exclusion of substrate conformers, Scientific Reports, 2016, 1-7, 6:34303.
De Genst, Erwin et al., Molecular basis for the preferential cleft recognition by dromedary heavy-chain antibodies, Proc. Natl. Acad. Sci. U. S. A., 2006, 4586-4591, vol. 103 | No. 12.
Di Costanzo, Luigi et al., Crystal structure of human arginase I at 1.29—A resolution and exploration of inhibition in the immune response, Proc. Natl. Acad. Sci. U. S. A., 2005, 13058-13063, 102.
Ganesan, Rajkumar et al., Structural and mechanistic insight into how antibodies inhibit serine proteases, Biochem. J., 2010, 179-189, 430.
Ganesan, Rajkumar et al., Unraveling the Allosteric Mechanism of Serine Protease Inhibition by an Antibody, Structure, 2009, 1614-1624, 17.
Grilo, António L. et al., The Increasingly Human and Profitable Monoclonal Antibody Market, Trends in Biotechnology, 2019, 9-16, vol. 37 | No. 1.
Holliger et al., Engineered antibody fragments and the rise of single domains, Nat. Biotechnol., 2005, pp. 1126-1136, 23.
Ilies, Monica et al., Binding of α,α-Disubstituted Amino Acids to Arginase Suggests New Avenues for Inhibitor Design, J. Med. Chem., 2011, 5432-5443, 54.
Kaplon, Hélène et al., Antibodies to watch in 2020, mAbs, 2020, 1703531-1-1703531-24, 12:1.
Koschubs, Tobias et al., Allosteric antibody inhibition of human hepsin protease, Biochem. J., 2012, 483-494, 442.
Kumar, Vinit et al., The Nature of Myeloid-Derived Suppressor Cells in the Tumor Microenvironment, Trends in Biotechnology, 2016, 208-220, 37.
Kusmartsev, Sergei et al., Immature myeloid cells and cancer-associated immune suppression, Cancer Immunol Immunother, 2002, 293-298, 51.
Kusmartsev, Sergei et al., Role of Immature Myeloid Cells in Mechanisms of Immune Evasion in Cancer, Cancer Immunol Immunother, 2006, 237-245, 55.
Lauwereys, M., et al., Potent enzyme inhibitors derived from dromedary heavy-chain antibodies, The EMBO Journal, 1998, pp. 3512-3520, vol. 17, No. 13.
Mitcheltree, Matthew J. et al., Discovery and Optimization of Rationally Designed Bicyclic Inhibitors of Human Arginase to Enhance Cancer Immunotherapy, ACS Med. Chem. Lett., 2020, 582-588, 11.
Munder, Markus, Arginase: an emerging key player in the mammalian immune system, British Journal of Pharmacology, 2009, 638-651, 158.
Oyen, David et al., Constraining Enzyme Conformational Change by an Antibody Leads to Hyperbolic Inhibition, J. Mol. Biol., 2011, 138-148, 407.
Pudlo, Marc et al., Arginase Inhibitors: A Rational Approach Over One Century, Med. Res. Rev., 2017, 475-513, 37.
Remy, Marie Helene et al., Characterization of monoclonal antibodies that strongly inhibit Electrophorus electricus acetylcholinesterase, Eur. J. Biochem., 1995, 651-658, 231.
Rodriguez, Paulo C. et al., Arginase | Production in the Tumor Microenvironment by Mature Myeloid Cells Inhibits T-Cell Receptor Expression and Antigen-Specific T-Cell Responses, Cancer Research, 2004, 5839-5849, 64.
Sahin, Emine et al., Macrophage PTEN Regulates Expression and Secretion of Arginase I Modulating Innate and Adaptive Immune Responses, J Immunol, 2014, 1717-1727, 193.
Serafini, Paolo et al., Myeloid suppressor cells in cancer: Recruitment, phenotype, properties, and mechanisms of immune suppression, Seminars in Cancer Biology, 2006, 53-65, 16.
Shields, Robert L. et al., High Resolution Mapping of the Bidning Site on Human IgG1 for FcyRI, FcyRII, FcyRIII, and ReRn and Design of IgG1 Variants with Improved Binding to the FcyR*, The Journal of Biological Chemistry, 2001, 6591-6604, 276(9).
Steggerda, Susanne M. et al., Inhibition of arginase by CB-1158 blocks myeloid cell-mediated immune suppression in the tumor microenvironment, Journal for ImmunoTherapy of Cancer, 2017, 1-18, 5:101.
Tsumoto, Kanta et al., Future perspectives of therapeutic monoclonal antibodies, Immunotherapy, 2019, 119-127, 11.
Van Zandt, Michael C. et al., Discovery of (R) 2-Amino-6-borono-2-(2-(piperidin-1-yl)ethyl)hexanoic Acid and Congeners as Highly Potent Inhibitors of Human Arginases I and II for Treatment of Myocardial Reperfusion Injury, J. Med. Chem., 2013, 2568-2580, 56.
Van Zandt, Michael C. et al., Discovery of N Substituted 3 Amino-4-(3-boronopropyl)pyrrolidine-3-carboxylic Acids as Highly Potent Third-Generation Inhibitors of Human Arginase I and II, J. Med. Chem., 2019, 8164-8177, 62.
Wei, Spencer C. et al., Fundamental Mechanisms of Immune Checkpoint Blockade Therapy, Cancer Discov., 2018, 1069-1086, 8.
Wu, Guoyao et al., Arginine metabolism and nutrition in growth, health and disease, Amino Acids, 2009, 153-168, 37.
Ahn, Meejung et al., Immunohistochemical study of arginase-1 in the spinal cords of rats with clip compression injury, Brain Research, 1445, 11-19, 2012.
Bian, Zhen et al., Arginase-1 is neither constitutively expressed in nor required for myeloid-derived suppressor cell-mediated inhibition of T-cell proliferation, Eur. J. Immunol., 48, 1046-1058, 2018.

(56) References Cited

OTHER PUBLICATIONS

Clark, Ian et al., A subset of well-differentiated hepatocellular carcinomas are Arginase-1 negative, Human Pathology, 69, 90-95, 2017.
Kanda, Hironori et al., Reduction of arginase I activity and manganese levels in the liver during exposure of rats to methylmercury: a possible mechanism, Arch Toxicol, 82, 803-808, 2008.
Lo, Kin-Ming et al., Antibody Engineering, Microbiology Spectrum, N/A, 1-17, 2014.
Martinenaite, Evelina et al., Frequent adaptive immune responses against arginase-1, OncoImmunology, 7(3), e1404215-1-e1404215-9, 2018.
Miret, Juan J. et al., Suppression of Myeloid Cell Arginase Activity leads to Therapeutic Response in a NSCLC Mouse Model by Activating Anti-Tumor Immunity, Journal for ImmunoTherapy of Cancer, 7:32, 1-12, 2019.
Tacha, David E. et al., A novel rabbit monoclonal antibody arginase-1 is highly specific and highly sensitive in hepatocellular carcinoma, Journal of Histotechnology, 38(4), 128-134, 2015.

* cited by examiner

VH1/VH2 (affinity matured) (Kabat)

```
                1       2       3       4       5        6       7       8         9      0
             12345678901234567890123456789012345678901234567890l2a345678901234567890123456789012abc34567890123456789O
VH1     (1)  QVQLVQSGAEVKKPGASVKVSCKASGYTFTNYGISWVRQAPGQGLEWMGWISAYNGNTNYAQKLQGRVTMTTDTSTSTAYMELRSLRSDDTAVYYCAREGAYGY
VH2     (1)  EVQLVQSGAEVKKPGASVKVSCKASGYTFFKYGISWVRQAPGQGLEWMGSISPYTGETHYAQKLQGRVTMTTDTSTSTAYMELRSLRSDDTAVYYCAREGAYGY
                      1
                      1     CDR1                CDR2                                             CDR3
             abcdefgh1234567890123
VH1  (100a)  RSPYHNWFDPWGQGTLVTVSS
VH2  (100a)  RSPYQNWFDPWGQGTLVTVSS
```

VH1/VH2 (affinity matured) (Chothia)

```
                                                                                                      1
                1       2       3       4       5        6       7       8         9      0
             12345678901234567890123456789012345678901234567890l2a345678901234567890123456789012abc34567890123456789O
VH1     (1)  QVQLVQSGAEVKKPGASVKVSCKASGYTFTNYGISWVRQAPGQGLEWMGWISAYNGNTNYAQKLQGRVTMTTDTSTSTAYMELRSLRSDDTAVYYCAREGAYGY
VH2     (1)  EVQLVQSGAEVKKPGASVKVSCKASGYTFFKYGISWVRQAPGQGLEWMGSISPYTGETHYAQKLQGRVTMTTDTSTSTAYMELRSLRSDDTAVYYCAREGAYGY
                      1
                      1   CDR1                CDR2                                               CDR3
             abcdefgh1234567890123
VH1  (100a)  RSPYHNWFDPWGQGTLVTVSS
VH2  (100a)  RSPYQNWFDPWGQGTLVTVSS
```

FIG.1A

VH1/VH2 (affinity matured) (Kabat+ Chothia)

```
                                                                                                 1
              1         2         3         4         5           6         7         8            9        0
       123456789012345678901234567890123456789012345678901 2a3456789012345678901234567890 12abc34567890123456 7890
VH1 (1) QVQLVQSGAEVKKPGASVKVSCKASGYTFTNYGISWVRQAPGQGLEWMGWISAYNGNTNYAQKLQGRVTMTTDTSTSTAYMELRSLRSDDTAVYYCAREGAYGY
VH2 (1) EVQLVQSGAEVKKPGASVKVSCKASGYTFFKYGISWVRQAPGQGLEWMGSISPYTGETHYAQKLQGRVTMTTDTSTSTAYMELRSLRSDDTAVYYCAREGAYGY
                      1
                      1    CDR1                 CDR2                                          CDR3
       abcdefgh1234567890123
VH1 (100a) RSPYHNWFDPWGQGTLVTVSS
VH2 (100a) RSPYQNWFDPWGQGTLVTVSS
```

VH1/VH2 (affinity matured) (AbM)

```
                                                                                                 1
              1         2         3         4         5           6         7         8            9        0
       123456789012345678901234567890123456789012345678901 2a3456789012345678901234567890 12abc34567890123456 7890
VH1 (1) QVQLVQSGAEVKKPGASVKVSCKASGYTFTNYGISWVRQAPGQGLEWMGWISAYNGNTNYAQKLQGRVTMTTDTSTSTAYMELRSLRSDDTAVYYCAREGAYGY
VH2 (1) EVQLVQSGAEVKKPGASVKVSCKASGYTFFKYGISWVRQAPGQGLEWMGSISPYTGETHYAQKLQGRVTMTTDTSTSTAYMELRSLRSDDTAVYYCAREGAYGY
                      1
                      1    CDR1              CDR2                                             CDR3
       abcdefgh1234567890123
VH1 (100a) RSPYHNWFDPWGQGTLVTVSS
VH2 (100a) RSPYQNWFDPWGQGTLVTVSS
```

FIG. 1B

VH1/VH2 (affinity matured) (IMGT)

```
                                                                                                   1
                1         2         3         4         5          6         7         8            9         0
           1234567890123456789012345678901234567890123456789012a345678901234567890123456789012abc34567890123456789 0
VH1    (1) QVQLVQSGAEVKKPGASVKVSCKASGYTFTNYGISWVRQAPGQGLEWMGWISAYNGNTNYAQKLQGRVTMTTDTSTSTAYMELRSLRSDDTAVYYCAREGAYGY
VH2    (1) EVQLVQSGAEVKKPGASVKVSCKASGYTFFKYGISWVRQAPGQGLEWMGSISPYTGETHYAQKLQGRVTMTTDTSTSTAYMELRSLRSDDTAVYYCAREGAYGY
                         1
                                CDR1                  CDR2                                             CDR3
                         1
           abcdefgh1234567890123
VH1 (100a) RSPYHNWFDPWGQGTLVTVSS
VH2 (100a) RSPYQNWFDPWGQGTLVTVSS
```

VH1/VH2 (affinity matured) (Contact)

```
                                                                                                   1
                1         2         3         4         5          6         7         8            9         0
           1234567890123456789012345678901234567890123456789012a345678901234567890123456789012abc34567890123456789 0
VH1    (1) QVQLVQSGAEVKKPGASVKVSCKASGYTFTNYGISWVRQAPGQGLEWMGWISAYNGNTNYAQKLQGRVTMTTDTSTSTAYMELRSLRSDDTAVYYCAREGAYGY
VH2    (1) EVQLVQSGAEVKKPGASVKVSCKASGYTFFKYGISWVRQAPGQGLEWMGSISPYTGETHYAQKLQGRVTMTTDTSTSTAYMELRSLRSDDTAVYYCAREGAYGY
                         1
                                  CDR1              CDR2                                                CDR3
                         1
           abcdefgh1234567890123
VH1 (100a) RSPYHNWFDPWGQGTLVTVSS
VH2 (100a) RSPYQNWFDPWGQGTLVTVSS
```

FIG.1C

VL (Kabat/Chothia/Kabat+Chothia/AbM)

```
                                                                                                             1
                   1         2         3         4         5         6         7         8         9         0
          1234567890123456789012345678901234567890123456789012345678901234567890123456789012345678901234567890
VL    (1) EIVMTQSPATLSLSPGERATLSCRASQSVSSYLAWYQQKPGQAPRLLIYDASNRATGIPARFSGSGSGTDFTLTISSLEPEDFAVYYCQQHSLLPRTFGG
                                    CDR1                     CDR2                                    CDR3
          1234567
VL  (101) GTKVEIK
```

VL (IMGT)

```
                                                                                                             1
                   1         2         3         4         5         6         7         8         9         0
          1234567890123456789012345678901234567890123456789012345678901234567890123456789012345678901234567890
VL    (1) EIVMTQSPATLSLSPGERATLSCRASQSVSSYLAWYQQKPGQAPRLLIYDASNRATGIPARFSGSGSGTDFTLTISSLEPEDFAVYYCQQHSLLPRTFGG
                                     CDR1                  CDR2                                      CDR3
          1234567
VL  (101) GTKVEIK
```

VL (Contact)

```
                                                                                                             1
                   1         2         3         4         5         6         7         8         9         0
          1234567890123456789012345678901234567890123456789012345678901234567890123456789012345678901234567890
VL    (1) EIVMTQSPATLSLSPGERATLSCRASQSVSSYLAWYQQKPGQAPRLLIYDASNRATGIPARFSGSGSGTDFTLTISSLEPEDFAVYYCQQHSLLPRTFGG
                                        CDR1               CDR2                                     CDR3
          1234567
VL  (101) GTKVEIK
```

FIG. 1D

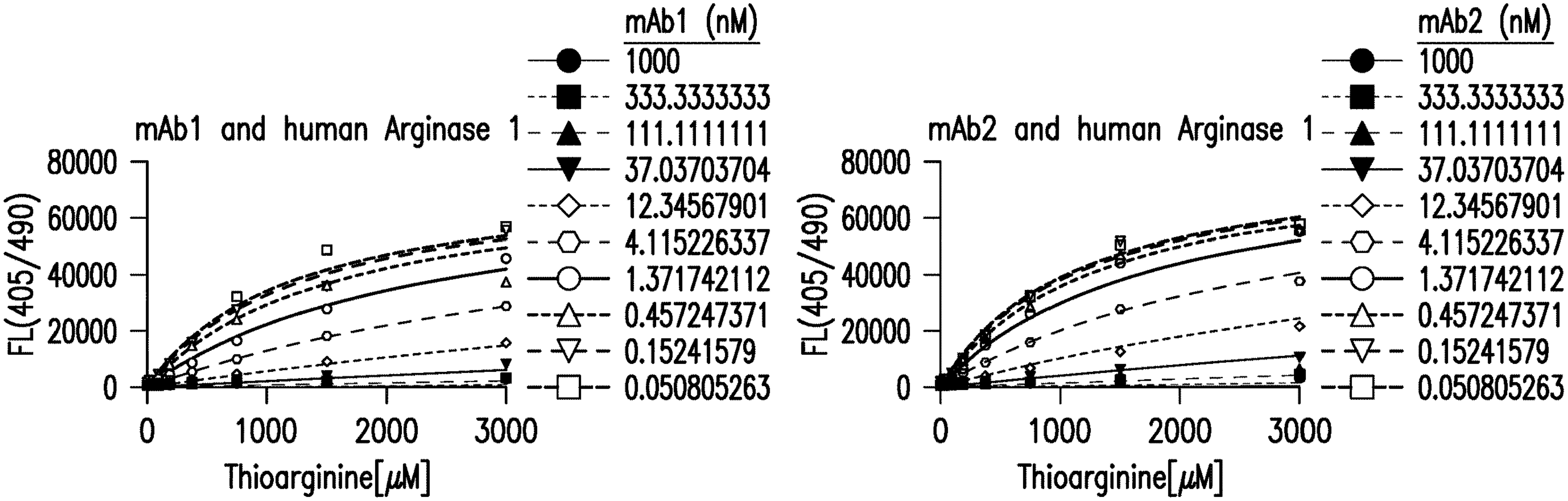

| | Global (shared) |
|---|---|
| Comparison of Fits | |
| Simpler model | Competitive inhibition |
| Probability it is correct | 99.99% |
| Alternate model | Noncompetitive inhibition |
| Probability it is correct | 0.015% |
| Preferred model | Competitive inhibition |
| Difference in AICc | −17.62 |

| | Global (shared) |
|---|---|
| Comparison of Fits | |
| Simpler model | Competitive inhibition |
| Probability it is correct | 99.98% |
| Alternate model | Noncompetitive inhibition |
| Probability it is correct | 0.02% |
| Preferred model | Competitive inhibition |
| Difference in AICc | −17.18 |

FIG. 2 mAb1 human Arg1 IC50 = 3.3 +/- 0.3 nM
mAb2 human Arg1 IC50 = 5.3 +/- 0.8 nM

Human Arginase 1

```
                                                                                                   1
         1         2         3         4         5         6         7         8         9         0
1234567890123456789012345678901234567890123456789012345678901234567890123456789012345678901234567890
MSAKSRTIGIIGAPFSKGQPRGGVEEGPTVLRKAGLLEKLKEQECDVKDYGDLPFADIPNDSPFQIVKNPRSVGKASEQLAGKVAEVKKNGRISLVLGGD

         1         1         1         1         1         1         1         1         1         2
         1         2         3         4         5         6         7         8         9         0
1234567890123456789012345678901234567890123456789012345678901234567890123456789012345678901234567890
HSLAIGSISGHARVHPDLGVIWVDAHTDINTPLTTTSGNLHGQPVSFLLKELKGKIPDVPGFSWVTPCISAKDIVYIGLRDVDPGEHYILKTLGIKYFSM

         2         2         2         2         2         2         2         2         2         3
         1         2         3         4         5         6         7         8         9         0
1234567890123456789012345678901234567890123456789012345678901234567890123456789012345678901234567890
TEVDRLGIGKVMEETLSYLLGRKKRPIHLSFDVDGLDPSFTPATGTPVVGGLTYREGLYITEEIYKTGLLSGLDIMEVNPSLGKTPEEVTRTVNTAVAITL

         3         3
         1         2
1234567890123456789012
LACFGLAREGNHKPIDYLNPPK
```

FIG. 9

ARGINASE 1 BINDERS FOR INHIBITING ARGINASE 1 ACTIVITY

CROSS-REFERENCE TO RELATED APPLICATIONS

This application is a U.S. National Stage application of International Patent Application No. PCT/US21/060254, filed Nov. 22, 2021, which claims priority to U.S. Provisional Patent Application No. 63/119,260, filed Nov. 30, 2020.

REFERENCE TO SEQUENCE LISTING SUBMITTED ELECTRONICALLY

The sequence listing of the present application is submitted electronically via EFS-Web as an ASCII formatted sequence listing with a file name "25132WOPCTSEQ.txt", that was filed with the international application on Nov. 22, 2021, and a size of 125 kilobytes. This sequence listing submitted via EFS-Web is part of the specification and is herein incorporated by reference in its entirety.

BACKGROUND OF THE INVENTION

(1) Field of the Invention

The present invention relates to Arginase 1 binders comprising human anti-human arginase 1 (hArg1) antibodies and antigen-binding fragments thereof that inhibit hArg1 through orthosteric and allosteric mechanisms.

(2) Description of Related Art

Human Arginase 1 is a metalloenzyme that catalyzes the hydrolysis of L-arginine to L-ornithine and urea and is a critical endogenous regulator of the immune system and a key player in T-cell function. This enzyme is constitutively expressed by myeloid derived suppressor cells (MDSCs), which are known immune system regulators. MDSCs have emerged as a key mediator of immunosuppression in human T-cells biology leading to significant decreases in the induction of antitumor activity (Bronte et al., J. Immunother. 24, 431-446 (2001); Kusmartsev. & Gabrilovich, Cancer Immunol. Immunother. 51, 293-298 (2002); Serafini et al., Semin. Cancer Biol. 16, 53-65 (2006); Kumar et al., Trends Immunol. 37, 208-220 (2016)). hArg1 catalyzes the degradation of the conditionally essential amino acid L-arginine into L-ornithine and urea in the final step of the urea cycle (Kumar et al., Ibid; Bronte et al., Trends Immunol. 24, 301-305 (2003); Rodriguez et al., Cancer Res. 64, 5839-5849 (2004)). This enzyme is present both intracellularly and excreted into the extracellular environment in a paracrine manner, with extracellular hArg1 maintaining its ability to deplete L-arginine (Pudlo et al., Med. Res. Rev. 37, 475-513 (2017); Sahin et al., J. Immunol. 193, 1717-1727 (2014); Munder, Br. J. Pharmacol. 158, 638-651 (2009); Wu et al., Amino Acids 37, 153-168 (20089)). As T-cells are dependent on L-arginine for growth and proliferation, its depletion leads to the effective suppression of T-cell immune responses and consequently supports the proliferation of tumor cells both in vitro and in vivo (Kumar et al. op. cit.; Rodriquez et al., op. cit. Activation of lymphocytes, specifically T-cells, via therapeutics targeted at immune checkpoint molecules enhances tumor cell killing and has led to long-lasting responses across various cancers (Wei et al., Cancer Discov. 8, 1069-1086 (2018)). High levels of hArg1 activity have been correlated with various types of cancer (Rodriquez et al., op. cit.; Kusmartsev & Gabrilovich, Cancer Immunol Immunother. 55, 237-245 (2006)).

hArg1 is a trimeric metalloenzyme in which each monomer is approximately 35 kDa in size with an extended, narrow active site approximately 15 Å deep that is terminated by two catalytic manganese (Mn) ions 3.3 Å apart (Ash, J. Nutr. 134, 2760-2764 (2004)). Several residues within the active site are critical for bridging the two Mn ions and in binding L-arginine (Ash, op. cit.; Costanzo et al., Proc. Natl. Acad. Sci. U.S.A 102, 13058-13063 (2005) and have been the main target of small molecule inhibitors (Ilies et al., J. Med. Chem. 54, 5432-5443 (2011); Cox et al., Nat. Struct. Biol. 6, 1043-1047 (1999); Van Zandt & Jagdmann Jr., Ring Constrained Analogs As Arginase Inhibitors. 1-21 (2015); Van Zandt et al., J. Med. Chem. 62, 8164-8177 (2019); Van Zandt et al., J. Med. Chem. 56, 2568-2580 (2013); Mitcheltree et al., ACS Med. Chem. Lett. 11, 582-588 (2020); Steggerda et al., Cancer 5, 1-18 (2017)). Efforts to discover pharmacological agents to inhibit hArg1 have been focused on amino acid-derived small molecules of usually less than 350 Da (Pudlo, op. cit.) that are able to enter and bind to residues within the hArg1 (Costanzo, op. cit.) active site. One avenue not previously described in literature for hArg1 inhibition is the use of therapeutic antibodies.

Monoclonal antibodies (mAbs) both in monotherapy and in combination regiments has emerged as one of the fastest growing and most effective therapeutic strategies for the treatment of solid tumors and hematological diseases. Between 2015 and 2017, the U.S. Food and Drug Administration approved 27 therapeutic mAbs (Tsumoto et al., Immunotherapy 11, 119-127 (2019)) increasing the total of clinically used mAbs and biosimilars in 2017 to 57 and 11, respectively (Grilo & Mantalaris, Trends Biotechnol. 37, 9-16 (2019)). As of late 2019, numerous companies were supporting over 550 novel antibody therapeutics in early phase clinical trials, with approximately half of these against oncology targets (Kaplon et al., MAbs 12, 1-24 (2020)).

Numerous published studies focused on the use of antibody fragments such as nanobodies, antigen-binding fragments (Fabs), and single-chain variable domain fragments (scFvs) as potent inhibitors of enzyme activity 25-34 (Dahms et al., Sci. Rep. 6, 1-7 (2016); Ganesan et al., Structural and mechanistic insight into how antibodies inhibit serine proteases. Biochem. J. 430, 179-189 (2010); Cinader. & Lafferty, Immunology 7, 342-362 (1964); Lauwereys et al., EMBO J. 17, 3512-3520 (1998); Holliger & Hudson, Nat. Biotechnol. 23, 1126-1136 (2005); Remy et al., Eur. J. Biochem. 231, 651-658 (1995); Oyen et al., J. Mol. Biol. 407, 138-148 (2011); Ganesan, Structure 17, 1614-1624 (2009); De Genst et al., Proc. Natl. Acad. Sci. U.S.A 103, 4586-4591 (2006); Koschubs, T. et al. Biochem. J. 442, 483-494 (2012)). The proposed mechanisms of inhibition by antibodies include adaptation to the catalytic site; adaptation to a site other than but near to the catalytic center thereby causing steric hindrance; aggregation of the antigen-antibody complex leading to steric hindrance by the structure of the aggregate; and interference with multimerization that may inhibit enzyme activity (Cinader, Annu. Rev. Microbiol. 11, 371-390 (1957)). Nevertheless, as noted by others, despite the myriad antibodies that have been and could be developed, the number of full-length monoclonal antibodies acting as enzyme inhibitors is "disappointingly low." (Lauwereys, op. cit.). MAbs excel in their ability to bind an antigen with high specificity and potency and function mainly by binding to large, flat surfaces on some receptors and protein:protein interaction surfaces that traditional small molecules cannot bind with suitable potency. Full-length neutralizing antibodies often lack the ability to access the narrow clefts and active site pockets of traditional enzymes due to their larger size, which often eliminates the ability to inhibit enzymatic activity.

Arginase-targeted therapies have been pursued across several disease areas including immunology, oncology, nervous system dysfunction, and cardiovascular dysfunction and diseases. Currently, all published hArg1 inhibitors are small molecules usually less than 350 Da in size.

BRIEF SUMMARY OF THE INVENTION

The present invention provides potent Arginase 1 binders that inhibit human arginase 1 (hArg1) comprising human anti-hArg1 antibodies and antigen-binding fragments thereof through orthosteric and allosteric mechanisms. These Arginase I binders may be useful for treating cancers and proliferative diseases.

The Arginase 1 binder of the present invention comprises three complementarity determining regions (CDRs) of an antibody heavy chain variable domain (VH) comprising the amino acid sequence set forth for VH1 in SEQ ID NO: 2 or an antibody VH comprising the amino acid sequence set forth for VH2 in SEQ ID NO: 3; and the three CDRs of an antibody light chain variable domain (VL) comprising the amino acid sequence set forth in SEQ ID NO: 4. Arginase 1 binders as disclosed herein specifically bind to arginase 1, and are capable of binding to two arginase 1 trimers to form a complex comprising three Arginase 1 binders and one arginase trimer. Arginase 1 binders as disclosed herein are capable of inhibiting arginase 1 activity. CDR sequences can be determined by any suitable numbering scheme including but not limited to Kabat, Chothia, Kabat+Chothia, AbM, ImMunoGeneTics (IMGT), or Contact numbering scheme.

In a further embodiment of the Arginase 1 binder, the VH CDRs comprise a VH1-CDR1 comprising the amino acid sequence set forth in SEQ ID NO: 5, a VH1-CDR2 comprising the amino acid sequence set forth in SEQ ID NO: 6, and a VH1-CDR3 comprising the amino acid sequence set forth in SEQ ID NO: 7; and the VL CDRs comprise a VL-CDR1 comprising the amino acid sequence set forth in SEQ ID NO: 31, a VL-CDR2 comprising the amino acid sequence set forth in SEQ ID NO: 32, and a VL-CDR3 comprising the amino acid sequence set forth in SEQ ID NO: 33. The CDR sequences are determined using the Kabat numbering scheme.

In a further embodiment of the Arginase 1 binder, the VH CDRs comprise a VH2-CDR1 comprising the amino acid sequence set forth in SEQ ID NO: 18, a VH2-CDR2 comprising the amino acid sequence set forth in SEQ ID NO: 19, and a VH2-CDR3 comprising the amino acid sequence set forth in SEQ ID NO: 20; and the VL CDRs comprise a VL-CDR1 comprising the amino acid sequence set forth in SEQ ID NO: 31, a VL-CDR2 comprising the amino acid sequence set forth in SEQ ID NO: 32, and a VL-CDR3 comprising the amino acid sequence set forth in SEQ ID NO: 33, wherein the CDR sequences are defined by Kabat.

In a further embodiment, the Arginase 1 binder comprises an antibody or antigen-binding fragment VH1 comprising the amino acid sequence set forth in SEQ ID NO: 2 and a VL1 comprising the amino acid sequence set forth in SEQ ID NO: 4.

In a further embodiment, the Arginase 1 binder comprises an antibody or antigen-binding fragment VH2 comprising the amino acid sequence set forth in SEQ ID NO: 3 and a VL comprising the amino acid sequence set forth in SEQ ID NO: 4.

In a further embodiment, the Arginase 1 binder further comprises a heavy chain constant domain of the IgG1, IgG2, IgG3, or IgG4 isotype.

In a further embodiment, the heavy chain constant domain of the IgG1, IgG2, IgG3, or IgG4 isotype comprises an Fc domain comprising one or more mutations that render the Fc domain effector-silent.

In a further embodiment, the light chain may comprise a human kappa light chain constant domain or a lambda light chain constant domain. In further embodiments disclosed herein, the light chain may comprise a human kappa light chain constant domain comprising SEQ ID NO: 58 or a lambda light chain constant domain comprising SEQ ID NO: 64.

The present invention further comprises a composition comprising the Arginase 1 binder disclosed herein and a pharmaceutically acceptable carrier or diluent.

The present invention further provides an Arginase 1 binder that is an antibody or an antigen binding fragment thereof comprising two identical Fabs, a first Fab comprising a first heavy chain variable domain (VH) and a first light chain variable domain (VL) and a second Fab comprising a second VH and a second VL, wherein the Arginase 1 binder binds two arginase 1 trimers, a first arginase 1 trimer and a second arginase 1 trimer, each comprising three arginase 1 monomers, wherein the first Fab binds to an epitope of two adjacent monomers of the first trimer and the second Fab binds to an epitope of two adjacent monomers of the second trimer, wherein (i) the VH of the first Fab binds to a portion of the epitope that spans two adjacent monomers of the first arginase 1 trimer and the VL of the first Fab binds to a portion of the epitope located solely on one monomer of the two adjacent monomers of the first arginase 1 trimer, and (ii) the VH of the second Fab binds to a portion of the epitope that spans two adjacent monomers of the second arginase 1 trimer and the VL of the second Fab binds to a portion of the epitope located solely on one monomer of the two adjacent monomers of the second arginase 1 trimer. The 2:3 ratio of two trimers to three antibodies may be identified using both isothermal titration calorimetry (ITC) and size exclusion chromatography with multi-angle light scattering (SEC-MALS) and/or cryo-electron microscopy.

In further embodiments, VH comprises a VH1-CDR1 comprising the amino acid sequence set forth in SEQ ID NO: 5, a VH1-CDR2 comprising the amino acid sequence set forth in SEQ ID NO: 6, and a VH1-CDR3 comprising the amino acid sequence set forth in SEQ ID NO: 7; and VL comprises a VL-CDR1 comprising the amino acid sequence set forth in SEQ ID NO: 31, a VL-CDR2 comprising the amino acid sequence set forth in SEQ ID NO: 32, and a VL-CDR3 comprising the amino acid sequence set forth in SEQ ID NO: 33; wherein for VH and VL, the CDR sequences are determined using the Kabat numbering scheme.

In a further embodiments, the VH is VH1 or VH2 and VH1 and VH2 comprise the amino acid sequence set forth in SEQ ID NO: 2 or 3, respectively, and VL comprises the amino acid sequence set forth in SEQ ID NO:4.

In a further embodiment of the Arginase 1 binder, (a) the VH of the first Fab and the second Fab each binds to (i) amino acids Lys39, Thr290, Pro286, Lys33, Ala34, Gly35, and Glu38 of a monomer (the first monomer) of the two adjacent monomers of the first arginase 1 trimer and second arginase 1 trimer, respectively, and (ii) amino acids Asp181, Lys284, Arg21, Pro20, Thr246, His126, Asp128, As130, Ser137, His141, Gly142, Asp183, Glu186, Thr136, Lys68, and Asn139 of another monomer (the second monomer) of the two adjacent monomers of the first arginase 1 trimer and second arginase 1 trimer, respectively; and (b) the VL of the first Fab and the second Fab each binds to amino acids Glu125, Ser16, Lys17, Asn69, Asp57, Pro20, Gly22, and Ser281 of one monomer of the two adjacent monomers of the first arginase 1 trimer and second arginase 1 trimer, respectively.

In a further embodiment of the Arginase 1 binder, the Arginase 1 binder binds two arginase 1 trimers to form a complex comprising a three to two ratio of Arginase 1 binder to arginase 1 trimer.

The present invention further provides an Arginase 1 binder comprising an antibody tetramer comprising two HC+LC pairs, wherein each HC and LC comprises a VH and a VL, respectively, and each VH and VL of a HC+LC pair forms a Fab to provide a first Fab comprising the VH and VL of one of the two HC+LC pairs and a second Fab comprising the VH and VL of the other of the two HC+LC pairs, and wherein the VH of the first Fab and the second Fab each binds to (i) amino acids Arg32, Lys33, Ala34, Gly35, Glu38, Lys39, Pro286, and Thr290 of the first monomer of two adjacent monomers of a first arginase 1 trimer and a second arginase 1 trimer, respectively, and (ii) amino acids Pro20, Arg21, Lys68, His126, Asp128, As130, Thr136, Ser137, Asn139, His141, Gly142, Asp181, Asp183, Glu186, Lys284, and Thr246 of the second monomer of the two adjacent monomers of the first arginase 1 trimer and the second arginase 1 trimer, respectively; and the VL of the first Fab and the second Fab each binds to amino acids Ser16, Lys17, Pro20, Gly22, Asp57, Asn69, Glu125, and Ser281 of one monomer of the two adjacent monomers of the first arginase 1 trimer and second arginase 1 trimer, respectively.

The present invention further provides an Arginase 1 binder that binds two adjacent monomers of an Arginase 1 trimer, wherein the Arginase 1 binder comprises a VH and a VL, wherein (i) the VH binds to the first monomer by interacting with amino acids Arg32, Lys33, Ala34, Gly35, Glu38, Lys39, Pro286, and Thr290 of the first monomer and amino acids Pro20, Arg21, Lys68, His126, Asp128, Asn130, Thr136, Ser137, Asn139, His141, Gly142, Asp181, Asp183, Glu186, Thr246, and Lys284, of the second monomer, and (ii) the VL binds the second monomer by interacting with amino acids Ser16, Lys17, Pro20, Gly22, Glu25, Asn69, Asp57, and Ser281 of the second monomer.

The present invention further provides an Arginase 1 binder comprising a VH comprising an amino acid sequence with at least 90% identity to the amino acid sequence set forth in SEQ ID NO: 2 and further comprising amino acids Tyr54, Gly56, Asn57 or Glu57, Thr58, Asn59 or His59, Thr69, Thr72, Asp73, Thr74, Ser75, Tyr102, Gly103, Tyr104, Arg105, Ser106, Pro107, and Tyr108, each amino acid position corresponding to the position shown in SEQ ID NO: 2; and a VL comprising an amino acid sequence with at least 90% identity to the amino acid sequence set forth in SEQ ID NO: 4 and further comprising amino acids Ser28, Tyr32, Ser67, Ser92, and Leu93, each amino acid position corresponding to the position shown in SEQ ID NO: 4.

The present invention further provides an Arginase 1 binder comprising a VH comprising an amino acid sequence with at least 90% identity to the amino acid sequence set forth in SEQ ID NO: 2 and further comprising amino acids Tyr54, Gly56, Asn57, Thr58, Asn59, Thr69, Thr72, Asp73, Thr74, Ser75, Tyr102, Gly103, Tyr104, Arg105, Ser106, Pro107, and Tyr108, each amino acid position corresponding to the position shown in SEQ ID NO: 2; and a VL comprising an amino acid sequence with at least 90% identity to the amino acid sequence set forth in SEQ ID NO: 4 and further comprising amino acids Ser28, Tyr32, Ser67, Ser92, and Leu93, each amino acid position corresponding to the position shown in SEQ ID NO: 4.

The present invention further provides an Arginase 1 binder comprising a VH comprising an amino acid sequence with at least 90% identity to the amino acid sequence set forth in SEQ ID NO: 3 and further comprising amino acids Tyr54, Gly56, Glu57, Thr58, His59, Thr69, Thr72, Asp73, Thr74, Ser75, Tyr102, Gly103, Tyr104, Arg105, Ser106, Pro107, and Tyr108, each amino acid position corresponding to the position shown in SEQ ID NO: 3; and a VL comprising an amino acid sequence with at least 90% identity to the amino acid sequence set forth in SEQ ID NO: 4 and further comprising amino acids Ser28, Tyr32, Ser67, Ser92, and Leu93, each amino acid position corresponding to the position shown in SEQ ID NO: 4.

The present invention further provides a composition comprising an Arginase 1 binder disclosed herein and a pharmaceutically acceptable carrier.

The present invention further provides a method for treating cancer or proliferative disease in an individual in need of the treatment comprising administering to the individual a therapeutically effective amount an Arginase 1 binder disclosed herein or a composition disclosed herein to treat the cancer or a proliferative disease.

The present invention further provides an arginase 1 binder or composition disclosed herein for treatment of cancers or proliferative diseases.

The present invention further provides for the use of an Arginase 1 binder disclosed herein for the manufacture of a medicament for treating cancer or proliferative disease.

The present invention further provides a combination therapy for treating a cancer or proliferative disease comprising an arginase 1 binder or composition disclosed herein and a therapeutic agent. In a further embodiment, the therapeutic agent is a chemotherapy agent or a therapeutic antibody. In a further still embodiment, the antibody is an anti-PD1 or anti-PD-L1 antibody.

The present invention further provides a nucleic acid molecule encoding the VH of an Arginase 1 binder disclosed herein and/or VL of an Arginase 1 binder disclosed herein. Further provided is an expression vector comprising one or more of the nucleic acid molecules disclosed herein. Further provided is host cell comprising an expression vector comprising one or more of the nucleic acid molecules disclosed herein.

The present invention further provides a method for producing an Arginase 1 binder comprising (a) providing a host cell comprising an expression vector comprising one or more of the nucleic acid molecules disclosed herein; (b) cultivating the host cell in a medium under conditions suitable for expressing the Arginase 1 binder; and (c) isolating the Arginase 1 binder from the medium.

In any one of the embodiments disclosed herein, the Arginase 1 binder further comprises a heavy chain constant domain of the IgG1, IgG2, IgG3, or IgG4 isotype. In a further embodiment thereof, the heavy chain constant domain of the IgG1, IgG2, IgG3, or IgG4 isotype comprises an Fc domain comprising one or more mutations that render the Fc domain effector-silent.

In any one of the embodiments disclosed herein, the light chain may comprise a human kappa light chain constant domain or a lambda light chain constant domain. In any one of the embodiments disclosed herein, the light chain may comprise a human kappa light chain constant domain comprising SEQ ID NO: 58 or a lambda light chain constant domain comprising SEQ ID NO: 64.

BRIEF DESCRIPTION OF THE DRAWINGS

FIG. 1A. Shows the CDRs of the VHT comprising the amino acid sequence set forth in SEQ ID NO: 2 (parent) and the VH2 comprising the amino acid sequence set forth in SEQ ID NO: 3 (affinity matured), each as defined according to Kabat and to Chothia. The amino acids in the affinity matured VH2 that differ from the amino acids in the parent VHT are shown in bold.

FIG. 1B. Shows the CDRs of the VHT comprising the amino acid sequence set forth in SEQ ID NO: 2 (parent) and the VH2 comprising the amino acid sequence set forth in SEQ ID NO: 3 (affinity matured), each as defined according to Kabat+Chothia and to AbM. The amino acids in the affinity matured VH2 that differ from the amino acids in the parent VHT are shown in bold.

FIG. 1C. Shows the CDRs of the VHT comprising the amino acid sequence set forth in SEQ ID NO: 2 (parent) and the VH2 comprising the amino acid sequence set forth in SEQ ID NO: 3 (affinity matured), each as defined according to IMGT and to Contact. The amino acids in the affinity matured VH2 that differ from the amino acids in the parent VHT are shown in bold.

FIG. 1D. Shows the CDRs of the VL comprising the amino acid sequence set forth in SEQ ID NO: 4, each as defined according to Kabat, to Chothia, to Kabat+Chothia to AbM, to IMGT; and to Contact.

FIG. 2. Shows the potency and multiplicity of infection (MOI) for mAb1 (left panel) and mAb2 (right panel). Antibody mAb1 comprises human VHT fused to mouse IgG2a constant domain and human VL fused to mouse kappa constant domain. Antibody mAb2 comprises human VHT fused to mouse IgG1 (D265A) constant domain and human VL fused to mouse kappa constant domain.

FIG. 9. Shows the amino acid sequence for human Arginase 1 (SEQ ID NO: 1). The amino acids boxed are amino acids at the mouth of the active site and the amino acids underlined are those amino acids involved in monomer:monomer interactions.

DETAILED DESCRIPTION OF THE INVENTION

Definitions

Figure 3:
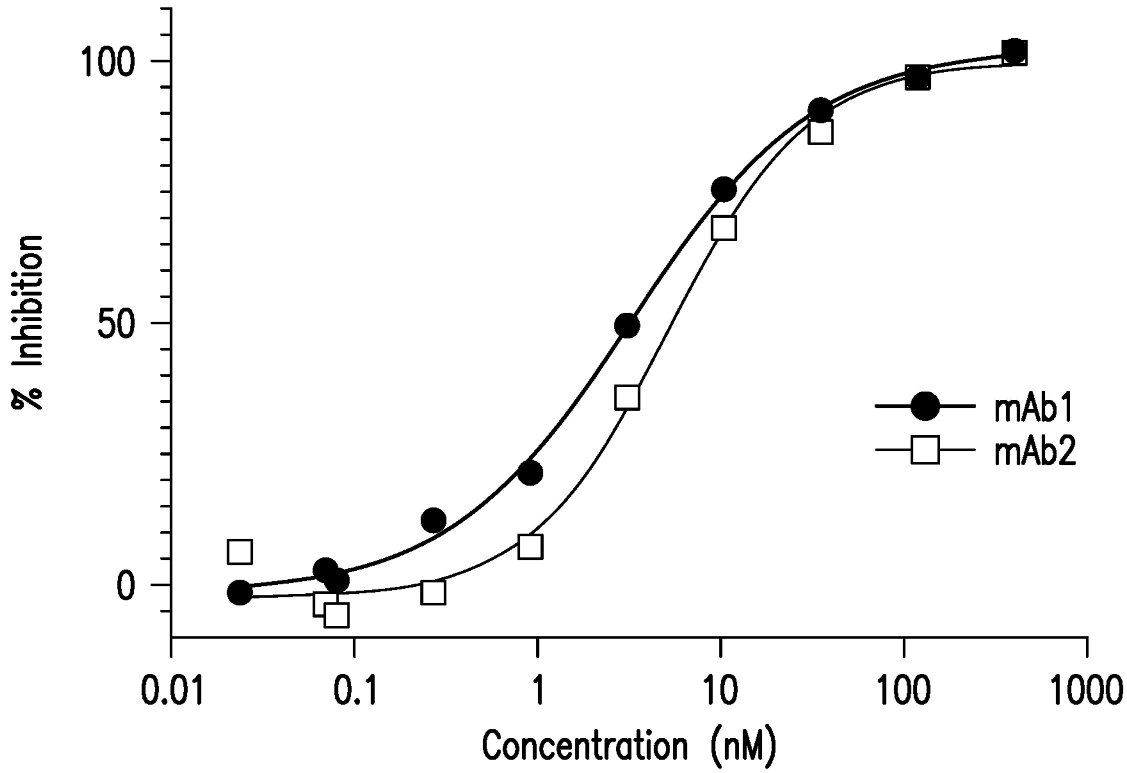
FIG. 3. Shows a dose response curve for mAb1 and Mab2 as determined by LC-MS.

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

As used herein, the term "Arginase" refers to a manganese-containing enzyme (EC 3.5.3.1, arginine amidinase, canavanase, L-arginase, arginine transamidinase) that catalyzes the conversion of arginine to ornithine+urea. It is the final enzyme of the urea cycle and is ubiquitous to all domains of life. Two isozymes of this arginase exist: arginase 1, which functions in the urea cycle, and is located primarily in the cytoplasm of hepatocytes (liver cells); and. arginase 2, which may be involved in the regulation of intracellular arginine/ornithine levels, and is located in mitochondria of several tissues in the body, with most abundance in the kidney and prostate and at lower levels in macrophages, lactating mammary glands, and brain. The amino acid sequence of human Arginase 1 is set forth in SEQ ID NO: 1 and shown in FIG. 9.

As used herein, the term "hArg1" refers to human arginase 1.

As used herein, the term "Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including KinExA and Biacore. Specific illustrative and exemplary embodiments for measuring binding affinity are described in the following.

As used herein, the term "administration" and "treatment," as it applies to an animal, human, experimental subject, cell, tissue, organ, or biological fluid, refers to contact of an exogenous pharmaceutical, therapeutic, diagnostic agent, or composition comprising an Arginase 1 binder as disclosed herein to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., human, rat, mouse, dog, cat, rabbit). In a preferred embodiment, the term "subject" refers to a human.

As used herein, the term "amino acid" refers to a simple organic compound containing both a carboxyl (—COOH) and an amino (—$NH_2$) group. Amino acids are the building blocks for proteins, polypeptides, and peptides. Amino acids occur in L-form and D-form, with the L-form in naturally occurring proteins, polypeptides, and peptides. Amino acids and their code names are set forth in the following chart.

| Amino acid | Three letter code | One letter code |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |

-continued

| Amino acid | Three letter code | One letter code |
|---|---|---|
| Tyrosine | Tyr | Y |
| Valine | Val | V |

As used herein, the term "antibody" or "immunoglobulin" as used herein refers to a glycoprotein comprising either (a) at least two heavy chains (HCs) and two light chains (LCs) inter-connected by disulfide bonds, or (b) in the case of a species of camelid antibody, at least two heavy chains (HCs) inter-connected by disulfide bonds. Each HC is comprised of a heavy chain variable region or domain (VH) and a heavy chain constant region or domain. Each light chain is comprised of an LC variable region or domain (VL) and a LC constant domain. In certain naturally occurring IgG, IgD and IgA antibodies, the heavy chain constant region is comprised of three domains, CH1, CH2 and CH3. In general, the basic antibody structural unit for antibodies is a Y-shaped tetramer comprising two HC/LC pairs (2H+2L), except for the species of camelid antibodies comprising only two HCs (2H), in which case the structural unit is a homodimer. Each tetramer includes two identical pairs of polypeptide chains, each pair having one LC (about 25 kDa) and HC chain (about 50-70 kDa) (H+L). Each HC:LC pair comprises one VH: one VL pair. The one VH:one VL pair may be referred to by the term "Fab". Thus, each antibody tetramer comprises two Fabs, one per each arm of the Y-shaped antibody.

The LC constant domain is comprised of one domain, CL. The human VH includes seven family members: VH1, VH2, VH3, VH4, VH5, VH6, and VH7; and the human VL includes 16 family members: Vκ1, Vκ2, Vκ3, Vκ4, Vκ5, Vκ6, Vλ1, Vλ2, Vλ3, Vλ4, Vλ5, Vλ6, Vλ7, Vλ8, Vλ9, and Vλ10. Each of these family members can be further divided into particular subtypes. The VH and VL can be further subdivided into regions of hypervariability, termed complementarity determining region (CDR) areas, interspersed with regions that are more conserved, termed framework regions (FR). Each VH and VL is composed of three CDR regions and four FR regions, arranged from amino-terminus to carboxy-terminus in the following order: FR1, CDR1, FR2, CDR2, FR3, CDR3, FR4. Numbering of the amino acids in a VH or VHH may be determined using the Kabat numbering scheme. See Béranger, et al., Ed. Ginetoux, *Correspondence between the IMGT unique numbering for C-DOMAIN, the IMGT exon numbering, the Eu and Kabat numberings: Human IGHG*, Created: 17 May 2001, Version: 8 Jun. 2016, which is accessible at www.imgt.org.

The constant regions of the antibodies may mediate the binding of the immunoglobulin to host tissues or factors, including various cells of the immune system (e.g., effector cells) and the first component (C1q) of the classical complement system. Typically, the numbering of the amino acids in the heavy chain constant domain begins with number 118, which is in accordance with the Eu numbering scheme. The Eu numbering scheme is based upon the amino acid sequence of human IgG1 (Eu), which has a constant domain that begins at amino acid position 118 of the amino acid sequence of the IgG1 described in Edelman et al., Proc. Natl. Acad. Sci. USA. 63: 78-85 (1969), and is shown for the IgG1, IgG2, IgG3, and IgG4 constant domains in Béranger, et al., op. cit.

The variable regions of the heavy and light chains contain a binding domain comprising the CDRs that interacts with an antigen. A number of methods are available in the art for defining CDR sequences of antibody variable domains (see Dondelinger et al., Frontiers in Immunol. 9: Article 2278 (2018)). The common numbering schemes include the following.

- Kabat numbering scheme is based on sequence variability and is the most commonly used (See Kabat et al. Sequences of Proteins of Immunological Interest, 5th Ed. Public Health Service, National Institutes of Health, Bethesda, Md. (1991) (defining the CDR regions of an antibody by sequence);
- Chothia numbering scheme is based on the location of the structural loop region (See Chothia & Lesk J. Mol. Biol. 196: 901-917 (1987); Al-Lazikani et al., J. Mol. Biol. 273: 927-948 (1997));
- AbM numbering scheme is a compromise between the two used by Oxford Molecular's AbM antibody modelling software (see Karu et al, *ILAR Journal* 37: 132-141 (1995);
- Contact numbering scheme is based on an analysis of the available complex crystal structures (See www.bioinf.org.uk: Prof Andrew C. R. Martin's Group; Abhinandan & Martin, Mol. Immunol. 45:3832-3839 (2008)).
- IMGT (ImMunoGeneTics) numbering scheme is a standardized numbering system for all the protein sequences of the immunoglobulin superfamily, including variable domains from antibody light and heavy chains as well as T cell receptor chains from different species and counts residues continuously from 1 to 128 based on the germ-line V sequence alignment (see Giudicelli et al., Nucleic Acids Res. 25:206-11 (1997); Lefranc, Immunol Today 18:509(1997); Lefranc et al., Dev Comp Immunol. 27:55-77 (2003)).

The following general rules disclosed in www.bioinforg.uk: Prof Andrew C. R. Martin's Group and reproduced in Table 1 below may be used to define the CDRs in an antibody sequence that includes those amino acids that specifically interact with the amino acids comprising the epitope in the antigen to which the antibody binds. There are rare examples where these generally constant features do not occur; however, the Cys residues are the most conserved feature.

TABLE 1

| Loop | Kabat | AbM | Chothia[1] | Contact[2] | IMGT |
|---|---|---|---|---|---|
| L1 | L24--L34 | L24--L34 | L24--L34 | L30--L36 | L27--L32 |
| L2 | L50--L56 | L50--L56 | L50--L56 | L46--L55 | L50--L51 |
| L3 | L89--L97 | L89--L97 | L89--L97 | L89--L96 | L89--L97 |
| H1 | H31--H35B (Kabat Numbering)[3] | H26--H35B | H26--H32 . . . 34 | H30--H35B | H26--H35B |
| H1 | H31--H35 (Chothia Numbering) | H26--H35 | H26--H32 | H30--H35 | H26--H33 |
| H2 | H50--H65 | H50--H58 | H52--H56 | H47--H58 | H51--H56 |
| H3 | H95--H102 | H95--H102 | H95--H102 | H93--H101 | H93--H102 |

[1]Some of these numbering schemes (particularly for Chothia loops) vary depending on the individual publication examined.
[2]Any of the numbering schemes can be used for these CDR definitions, except the Contact numbering scheme uses the Chothia or Martin (Enhanced Chothia) definition.
[3]The end of the Chothia CDR-H1 loop when numbered using the Kabat numbering convention varies between H32 and H34 depending on the length of the loop. (This is because the Kabat numbering scheme places the insertions at H35A and H35B.)
If neither H35A nor H35B is present, the loop ends at H32
If only H35A is present, the loop ends at H33
If both H35A and H35B are present, the loop ends at H34

The entire nucleotide sequence of the heavy chain and light chain variable regions are commonly numbered according to Kabat while the three CDRs within the variable region may be defined according to any one of the aforementioned numbering schemes.

In general, the state of the art recognizes that in many cases, the CDR3 region of the heavy chain is the primary determinant of antibody specificity, and examples of specific antibody generation based on CDR3 of the heavy chain alone are known in the art (e.g., Beiboer et al., J. Mol. Biol. 296: 833-849 (2000); Klimka et al., British J. Cancer 83: 252-260 (2000); Rader et al., Proc. Natl. Acad. Sci. USA 95: 8910-8915 (1998); Xu et al., Immunity 13: 37-45 (2000).

As used herein, the term "Fc domain", or "Fc" as used herein is the crystallizable fragment domain or region obtained from an antibody that comprises the CH2 and CH3 domains of an antibody. In an antibody, the two Fc domains are held together by two or more disulfide bonds and by hydrophobic interactions of the CH3 domains. The Fc domain may be obtained by digesting an antibody with the protease papain. Typically, amino acids in the Fc domain are numbered according to the Eu numbering convention (See Edelmann et al., Biochem. 63: 78-85 (1969)).

As used herein, the term "antigen" as used herein refers to any foreign substance which induces an immune response in the body.

As used here, the term "Arginase 1 binder" refers to a polypeptide or protein molecule that binds to arginase 1. An Arginase 1 binder includes but is not limited to a bivalent antibody tetramer (2H+2L), a monovalent antibody (H+L), a bi-specific antibody that targets arginase 1 and another target, a Fab fragment, a Fab' fragment, a F(ab')2 fragment, an Fv region, and an ScFv. Unless otherwise indicated, the Arginase 1 binders herein bind to and inhibit the activity of hARG1.

As used herein, the term "antigen binding fragment" refers to a polypeptide or polypeptides comprising a fragment of a full length antibody, which retains the ability to specifically bind to the antigen bound by the full length antibody, and/or to compete with the full length antibody for specifically binding to the antigen. Examples of antigen binding fragments include but are not limited to Fab fragment, Fab' fragment, F(ab')2 fragment, Fv region, and scFv.

As used herein, the term "Fab fragment" refers to an antigen binder comprising one antibody light chain and the CH1 and VH of one antibody heavy chain. The heavy chain of a Fab molecule cannot form a disulfide bond with another heavy chain molecule. A "Fab fragment" can be the product of papain cleavage of an antibody.

As used herein, the term "Fab' fragment" refers to an antigen binder comprising one antibody light chain and a portion or fragment of one antibody heavy chain that contains the VH and the CH1 domain up to a region between the CH1 and C H2 domains, such that an interchain disulfide bond can be formed between the two heavy chains of two Fab' fragments to form a F(ab')2 molecule.

As used herein, the term "F(ab')2 fragment" refers to an antigen binder comprising two antibody light chains and two heavy chains containing the VH and the CH1 domain up to a region between the CH1 and CH2 domains, such that an interchain disulfide bond is formed between the two heavy chains. An F(ab')2 fragment thus is composed of two Fab' fragments that are held together by a disulfide bond between the two heavy chains. An "F(ab')2 fragment" can be the product of pepsin cleavage of an antibody.

As used herein, the term "Fv region" refers to an antigen binder comprising the variable regions from both the heavy and light chains of an antibody, but lacks the constant regions.

As used herein, the term "ScFv" or "single-chain variable fragment" refers to a fusion protein comprising a VH and VL fused or linked together by a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker.

As used herein, the term "diabody" refers to an antigen binder comprising a small antibody fragment with two antigen-binding regions, which fragments comprise a heavy chain variable domain (VH) connected to a light chain variable domain (VL) in the same polypeptide chain (VH-VL or VL-VH). By using a linker that is too short to allow pairing between the two domains on the same chain, the domains are forced to pair with the complementarity domains of another chain and create two antigen-binding regions. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

These and other potential constructs are described at Chan & Carter (2010) Nat. Rev. Immunol. 10:301. These antibody fragments are obtained using conventional techniques known to those with skill in the art, and the fragments are screened for utility in the same manner as are intact antibodies. Antigen-binding fragments can be produced by recombinant DNA techniques, or by enzymatic or chemical cleavage of intact immunoglobulins.

As used herein, the term "isolated" antibodies or antigen-binding fragments thereof (e.g., antigen binders such as Arginase 1 binders) are at least partially free of other biological molecules from the cells or cell cultures in which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

As used herein, the term "monoclonal antibody" refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J.* Mol. Biol. 222: 581-597, for example. See also Presta (2005) *J. Allergy Clin. Immunol.* 116:731.

As used herein, the term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include non-expressed DNA segments that, for example, form recognition sequences for other proteins. "Genes" can be obtained from a variety of sources, including cloning from a source of interest or synthesizing from known or predicted sequence information, and may include sequences designed to have desired parameters. Genes include both naturally occurring nucleotide sequences encoding a molecule of interest and synthetically derived nucleotide sequences encoding a molecule of interest, for example, complementary DNA (cDNA) obtained from a messenger RNA (mRNA) nucleotide sequence.

As used herein, the term "germline" or "germline sequence" refers to a sequence of unrearranged immunoglobulin DNA sequences. Any suitable source of unrearranged immunoglobulin sequences may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. (2005) Nucleic Acids Res. 33:D256-D261.

As used herein, the term "library" as used herein is, typically, a collection of related but diverse polynucleotides that are, in general, in a common vector backbone. For example, a light chain or heavy chain immunoglobulin library may contain polynucleotides, in a common vector backbone, that encode light and/or heavy chain immunoglobulins, which are diverse but related in their nucleotide sequence; for example, which immunoglobulins are functionally diverse in their abilities to form complexes with other immunoglobulins, e.g., in an antibody display system of the present invention, and bind a particular antigen.

As used herein, the term "polynucleotides" discussed herein form part of the present invention. A "polynucleotide", "nucleic acid" or "nucleic acid molecule" include DNA and RNA, single- or double-stranded. Polynucleotides e.g., encoding an immunoglobulin chain or component of the antibody display system of the present invention, may, in an embodiment of the invention, be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

Polynucleotides e.g., encoding an immunoglobulin chain or component of the antibody display system of the present invention, may be operably associated with a promoter. A "promoter" or "promoter sequence" is, in an embodiment of the invention, a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease Si), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the β-lactamase promoter (Villa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

As used herein, the terms "vector", "cloning vector" and "expression vector" include a vehicle (e.g., a plasmid) by which a DNA or RNA sequence can be introduced into a host cell, so as to transform the host and, optionally, promote expression and/or replication of the introduced sequence. Polynucleotides encoding an immunoglobulin chain or component of the antibody display system of the present invention may, in an embodiment of the invention, be in a vector.

As used herein, the terms "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, the term "control sequences" or "regulatory sequences" refers to DNA sequences necessary for the expression of an operably linked coding sequence in a particular host organism. The control sequences that are suitable for expression in eukaryotes, for example, include a promoter, operator or enhancer sequences, transcription termination sequences, and polyadenylation sequences for expression of a messenger RNA encoding a protein and a ribosome binding site for facilitating translation of the messenger RNA.

As used herein, a nucleic acid is "operably linked" when it is placed into a functional relationship with another nucleic acid sequence, e.g., a regulatory sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "expression" as used herein is defined as the transcription and/or translation of a particular nucleotide sequence.

As used herein, the term "inhibits arginase 1 activity" means the ability to inhibit the formation of ornithine from arginine. Inhibition may be determined in an assay that detects formation of thioomithine from thioarginine, for example, the assay taught in Example 4 or by liquid chromatography-mass spectroscopy (LC-MS), for example, as taught in Example 5.

As used herein, the term "treat" or "treating" means to administer a therapeutic agent, such as a composition containing any of the Arginase binders of the present invention, topically, subcutaneously, intramuscular, intradermally, or systemically to an individual in need. The amount of a therapeutic agent that is effective to treat cancer or proliferative disease in the individual may vary according to factors such as the injury or disease state, age, and/or weight of the individual, and the ability of the therapeutic agent to elicit a desired response in the individual. Whether the therapeutic objective has been achieved can be assessed by the individual and/or any clinical measurement typically used by physicians or other skilled healthcare providers to assess the severity or progression status of the treatment. Thus, the terms denote that a beneficial result has been or will be conferred on a human or animal individual in need.

As used herein, the term "treatment," as it applies to a human or veterinary individual, refers to therapeutic treatment, as well as diagnostic applications. "Treatment" as it applies to a human or veterinary individual, encompasses contact of the antibodies or antigen binding fragments of the present invention to a human or animal subject. As used herein, the term "therapeutically effective amount" refers to a quantity of a specific substance sufficient to achieve a desired effect in an individual being treated. For instance, this may be the amount necessary to inhibit or reduce the severity of a disease or disorder in an individual.

As used herein, the term "Combination therapy" refers to treatment of a human or animal individual comprising administering a first therapeutic agent and a second therapeutic agent consecutively or concurrently to the individual. In general, the first and second therapeutic agents are administered to the individual separately and not as a mixture; however, there may be embodiments where the first and second therapeutic agents are mixed prior to administration.

Arginase 1 Binders

The Arginase 1 binders of the present invention are fully human antibodies obtained by screening synthetically constructed human IgG pre-immune yeast display libraries with a diversity of $10^{10}$ with hArg1. The Arginase 1 binders of the present invention comprise VH (designated VH1) and VL derived from a single antibody obtained from the library, which in a further embodiment said VH1 domain was affinity matured to produce an affinity matured VH2 domain.

These Arginase 1 binders of the present invention comprise six complementarity determining regions (CDRs) comprising a particular combination of three CDRs as presented in the table below. The CDR amino acid sequences shown in Tables 2-7 and FIGS. 1A-1D are set forth according to the Kabat, Chothia, Kabat+Chothia, AbM, IMGT, and Contact numbering schemes for identifying CDR amino acid sequences. A particular CDR amino acid sequence determined using any one of the these schemes advanced for identifying CDR amino acid sequences (See Table 1) have more or less amino acids than that of CDR amino acid sequences identified according to any other numbering scheme but will overlap the CDR amino acid sequences. Thus, the CDR amino acid sequences shown herein are not to be construed as limiting and any Arginase 1 binder in which the CDR amino acid sequences have been identified by another numbering scheme will fall within the scope of the Arginase 1 binders of the present invention provided the amino acid sequences for such Arginase 1 binders comprise the six CDR amino acid sequences as identified by any one of the numbering schemes and shown in Tables 2-7 and shown FIGS. 1A-1D. For all antibodies disclosed herein unless indicated otherwise, the amino acids comprising the variable domains are numbered according to the Kabat numbering scheme independently of how the amino acids are defined using Kabat, Chothia, Kabat+Chothia, AbM, IMGT, or Contact schemes and the constant domains are numbered according to the Eu numbering scheme.

The Arginase 1 binders comprise a VH1 or VH2 and a VL, each domain comprising three CDRs and four Frameworks (FR) in the following arrangement

FR1-CDR1-FR2-CDR2-FR3-CDR3-FR4.

The Arginase 1 binder VH-CDRs and VL-CDRs may comprise the amino acid sequences shown in Table 2-7 as defined according to Kabat, Chothia, Kabat+Chothia, AbM, IMGT, and Contact numbering schemes, respectively.

TABLE 2

Amino Acid Sequences of Arginase 1 Binders VH1, VH2, and VL CDRs as defined by Kabat

| | VH1-CDR1 | VH1-CDR2 | VH1-CDR3 |
|---|---|---|---|
| VH1 | NYGIS (SEQ IF NO: 5) | WISAYNGNTNYAQKLQG (SEQ ID NO: 6) | EGAYGYRSPYHNWFDP (SEQ ID NO: 7) |
| | VH2-CDR1 | VH2-CDR2 | VH2-CDR3 |
| VH2 | **K**YGIS (SEQ ID NO: 18) | SIS**PYTGETH**YAQKLQG (SEQ ID NO: 19) | EGAYGYRSPY**Q**NWFDP (SEQ ID NO: 20) |
| | VL-CDR1 | VL-CDR2 | VL-CDR3 |
| VL | RASQSVSSYLA (SEQ ID NO: 31) | DASNRAT (SEQ ID NO: 32) | QQHSLLPRT (SEQ ID NO: 33) |

VH2 amino acids in bold indicate the amino acid is a substitution of the corresponding amino acid in VH1

TABLE 3

Amino Acid Sequences of Arginase 1 Binders VH1, VH2, and VL CDRs as defined by Chothia

| | VH1-CDR1 | VH1-CDR2 | VH1-CDR3 |
|---|---|---|---|
| VH1 | GYTFTNY (SEQ IF NO: 8) | SAYNGN (SEQ ID NO: 9) | EGAYGYRSPYHNWFDP (SEQ ID NO: 7) |
| | VH2-CDR1 | VH2-CDR2 | VH2-CDR3 |
| VH2 | GYTF**FK**Y (SEQ ID NO: 21) | S**PYTGE** (SEQ ID NO: 22) | EGAYGYRSPY**Q**NWFDP (SEQ ID NO: 20) |

TABLE 3-continued

| Amino Acid Sequences of Arginase 1 Binders VH1, VH2, and VL CDRs as defined by Chothia | | | |
|---|---|---|---|
| | VL-CDR1 | VL-CDR2 | VL-CDR3 |
| VL | RASQSVSSYLA (SEQ ID NO: 31) | DASNRAT (SEQ ID NO: 32) | QQHSLLPRT (SEQ ID NO: 33) |

VH2 amino acids in bold indicate the amino acid is a substitution of the corresponding amino acid in VH1

TABLE 4

| Amino Acid Sequences of Arginase 1 Binders VH1, VH2, and VL CDRs as defined by Kabat + Chothia | | | |
|---|---|---|---|
| | VH1-CDR1 | VH1-CDR2 | VH1-CDR3 |
| VH1 | GYTFTNYGIS (SEQ IF NO: 10) | WISAYNGNTNYAQKLQG (SEQ ID NO: 6) | EGAYGYRSPYHNWFDP (SEQ ID NO: 7) |
| | VH2-CDR1 | VH2-CDR2 | VH2-CDR3 |
| VH2 | GYTF**FK**YGIS (SEQ ID NO: 23) | SIS**PYTGETH**YAQKLQG (SEQ ID NO: 19) | EGAYGYRSPY**Q**NWFDP (SEQ ID NO: 20) |
| | VL-CDR1 | VL-CDR2 | VL-CDR3 |
| VL | RASQSVSSYLA (SEQ ID NO: 31) | DASNRAT (SEQ ID NO: 32) | QQHSLLPRT (SEQ ID NO: 33) |

VH2 amino acids in bold indicate the amino acid is a substitution of the corresponding amino acid in VH1

TABLE 5

| Amino Acid Sequences of Arginase 1 Binders VH1, VH2, and VL CDRs as defined by AbM | | | |
|---|---|---|---|
| | VH1-CDR1 | VH1-CDR2 | VH1-CDR3 |
| VH1 | GYTFTNYGIS (SEQ IF NO: 10) | WISAYNGNTN (SEQ ID NO: 11) | EGAYGYRSPYHNWFDP (SEQ ID NO: 7) |
| | VH2-CDR1 | VH2-CDR2 | VH2-CDR3 |
| VH2 | GYTF**FK**YGIS (SEQ ID NO: 23) | SIS**PYTGETH**YAQKLQG (SEQ ID NO: 24) | EGAYGYRSPY**Q**NWFDP (SEQ ID NO: 20) |
| | VL-CDR1 | VL-CDR2 | VL-CDR3 |
| VL | RASQSVSSYLA (SEQ ID NO: 31) | DASNRAT (SEQ ID NO: 32) | QQHSLLPRT (SEQ ID NO: 33) |

VH2 amino acids in bold indicate the amino acid is a substitution of the corresponding amino acid in VH1

TABLE 6

| Amino Acid Sequences of Arginase 1 Binders VH1, VH2, and VL CDRs as defined by IMGT | | | |
|---|---|---|---|
| | VH1-CDR1 | VH1-CDR2 | VH1-CDR3 |
| VH1 | GYTFTNYG (SEQ IF NO: 12) | ISAYNGN (SEQ ID NO: 13) | AREGAYGYRSPYHNWFDP (SEQ ID NO: 14) |
| | VH2-CDR1 | VH2-CDR2 | VH2-CDR3 |
| VH2 | GYTF**FK**YG (SEQ ID NO: 25) | IS**PYTGE** (SEQ ID NO: 26) | AREGAYGYRSPY**Q**NWFDP (SEQ ID NO: 27) |

TABLE 6-continued

| Amino Acid Sequences of Arginase 1 Binders VH1, VH2, and VL CDRs as defined by IMGT | | | |
|---|---|---|---|
| | VL-CDR1 | VL-CDR2 | VL-CDR3 |
| VL | QSVSSYLA (SEQ ID NO: 32) | DA | QQHSLLPRT (SEQ ID NO: 33) |

VH2 amino acids in bold indicate the amino acid is a substitution of the corresponding amino acid in VH1

TABLE 7

| Amino Acid Sequences of Arginase 1 Binders VH1, VH2, and VL CDRs as defined by Contact | | | |
|---|---|---|---|
| | VH1-CDR1 | VH1-CDR2 | VH1-CDR3 |
| VH1 | TNYGIS (SEQ IF NO: 15) | WMGWISAYNGNTN (SEQ ID NO: 16) | AREGAYGYRSPYHNWFD (SEQ ID NO: 17) |
| | VH2-CDR1 | VH2-CDR2 | VH2-CDR3 |
| VH2 | **FK**YGIS (SEQ ID NO: 28) | WMGSIS**PYTGE**TN (SEQ ID NO: 29) | AREGAYGYRSPY**Q**NWFD (SEQ ID NO: 30) |
| | VL-CDR1 | VL-CDR2 | VL-CDR3 |
| VL | SSYLAWY (SEQ ID NO: 35) | LLIYDASNRA (SEQ ID NO: 36) | QQHSLLPR (SEQ ID NO: 37) |

VH2 amino acids in bold indicate the amino acid is a substitution of the corresponding amino acid in VH1

In particular embodiments of the invention, the Arginase 1 binder comprises (a) a VH1-CDR1 comprising the amino acid sequence set forth in SEQ ID NO: 5, a VH1-CDR2 comprising the amino acid sequence set forth in SEQ ID NO: 6, and a VH1-CDR3 comprising the amino acid sequence set forth in SEQ ID NO: 7; and (b) a VL-CDR1 comprising the amino acid sequence set forth in SEQ ID NO: 31, a VL-CDR2 comprising the amino acid sequence set forth in SEQ ID NO: 32, and a VL-CDR3 comprising the amino acid sequence set forth in SEQ ID NO: 33. The Arginase 1 binders specifically bind arginase 1 and inhibit arginase 1 activity. CDR sequences are determined using the Kabat numbering scheme.

In particular embodiments of the invention, the Arginase 1 binder comprises (a) a VH2-CDR1 comprising the amino acid sequence set forth in SEQ ID NO: 18, a VH2-CDR2 comprising the amino acid sequence set forth in SEQ ID NO: 19, and a VH2-CDR3 comprising the amino acid sequence set forth in SEQ ID NO: 20; and (b) a VL-CDR1 comprising the amino acid sequence set forth in SEQ ID NO: 31, a VL-CDR2 comprising the amino acid sequence set forth in SEQ ID NO: 32, and a VL-CDR3 comprising the amino acid sequence set forth in SEQ ID NO: 33. The Arginase 1 binders specifically bind arginase 1 and inhibit arginase 1 activity. CDR sequences are determined using the Kabat numbering scheme.

In particular embodiments of the invention, the Arginase 1 binder comprises (a) a VH1-CDR1 comprising the amino acid sequence set forth in SEQ ID NO: 8, a VH1-CDR2 comprising the amino acid sequence set forth in SEQ ID NO: 9, and a VH1-CDR3 comprising the amino acid sequence set forth in SEQ ID NO: 7; and (b) a VL-CDR1 comprising the amino acid sequence set forth in SEQ ID NO: 31, a VL-CDR2 comprising the amino acid sequence set forth in SEQ ID NO: 32, and a VL-CDR3 comprising the amino acid sequence set forth in SEQ ID NO: 33. The Arginase 1 binders specifically bind arginase 1 and inhibit arginase 1 activity. CDR sequences are determined using the Chothia numbering scheme.

In particular embodiments of the invention, the Arginase 1 binder comprises (a) a VH2-CDR1 comprising the amino acid sequence set forth in SEQ ID NO: 21, a VH2-CDR2 comprising the amino acid sequence set forth in SEQ ID NO: 22, and a VH2-CDR3 comprising the amino acid sequence set forth in SEQ ID NO: 20; and (b) a VL-CDR1 comprising the amino acid sequence set forth in SEQ ID NO: 31, a VL-CDR2 comprising the amino acid sequence set forth in SEQ ID NO: 32, and a VL-CDR3 comprising the amino acid sequence set forth in SEQ ID NO: 33. The Arginase 1 binders specifically bind arginase 1 and inhibit arginase 1 activity. CDR sequences are determined using the Chothia numbering scheme.

In particular embodiments of the invention, the Arginase 1 binder comprises (a) a VH1-CDR1 comprising the amino acid sequence set forth in SEQ ID NO: 10, a VH1-CDR2 comprising the amino acid sequence set forth in SEQ ID NO: 6, and a VH1-CDR3 comprising the amino acid sequence set forth in SEQ ID NO: 7; and (b) a VL-CDR1 comprising the amino acid sequence set forth in SEQ ID NO: 31, a VL-CDR2 comprising the amino acid sequence set forth in SEQ ID NO: 32, and a VL-CDR3 comprising the amino acid sequence set forth in SEQ ID NO: 33. The Arginase 1 binders specifically bind arginase 1 and inhibit arginase 1 activity. CDR sequences are determined using the Kabat+Chothia numbering scheme.

In particular embodiments of the invention, the Arginase 1 binder comprises (a) a VH2-CDR1 comprising the amino acid sequence set forth in SEQ ID NO: 23, a VH2-CDR2 comprising the amino acid sequence set forth in SEQ ID NO: 19, and a VH2-CDR3 comprising the amino acid sequence set forth in SEQ ID NO: 20; and (b) a VL-CDR1 comprising the amino acid sequence set forth in SEQ ID NO: 31, a VL-CDR2 comprising the amino acid sequence set forth in SEQ ID NO: 32, and a VL-CDR3 comprising the amino acid sequence set forth in SEQ ID NO: 33. The Arginase 1 binders specifically bind arginase 1 and inhibit arginase 1 activity. CDR sequences are determined using the Kabat+Chothia numbering scheme.

In particular embodiments of the invention, the Arginase 1 binder comprises (a) a VH1-CDR1 comprising the amino acid sequence set forth in SEQ ID NO: 10, a VH1-CDR2 comprising the amino acid sequence set forth in SEQ ID NO: 11, and a VH1-CDR3 comprising the amino acid sequence set forth in SEQ ID NO: 7; and (b) a VL-CDR1 comprising the amino acid sequence set forth in SEQ ID NO: 31, a VL-CDR2 comprising the amino acid sequence set forth in SEQ ID NO: 32, and a VL-CDR3 comprising the amino acid sequence set forth in SEQ ID NO: 33. The Arginase 1 binders specifically bind arginase 1 and inhibit arginase 1 activity. CDR sequences are determined using the AbM numbering scheme.

In particular embodiments of the invention, the Arginase 1 binder comprises (a) a VH2-CDR1 comprising the amino acid sequence set forth in SEQ ID NO: 23, a VH2-CDR2 comprising the amino acid sequence set forth in SEQ ID NO: 24, and a VH2-CDR3 comprising the amino acid sequence set forth in SEQ ID NO: 20; and (b) a VL-CDR1 comprising the amino acid sequence set forth in SEQ ID NO: 31, a VL-CDR2 comprising the amino acid sequence set forth in SEQ ID NO: 32, and a VL-CDR3 comprising the amino acid sequence set forth in SEQ ID NO: 33. The Arginase 1 binders specifically bind arginase 1 and inhibit arginase 1 activity. CDR sequences are determined using the AbM numbering scheme.

In particular embodiments of the invention, the Arginase 1 binder comprises (a) a VH1-CDR1 comprising the amino acid sequence set forth in SEQ ID NO: 12, a VH1-CDR2 comprising the amino acid sequence set forth in SEQ ID NO: 13, and a VH1-CDR3 comprising the amino acid sequence set forth in SEQ ID NO: 14; and (b) a VL-CDR1 comprising the amino acid sequence set forth in SEQ ID NO: 34, a VL-CDR2 comprising the amino acid sequence DA, and a VL-CDR3 comprising the amino acid sequence set forth in SEQ ID NO: 33. The Arginase 1 binders specifically bind arginase 1 and inhibit arginase 1 activity. CDR sequences are determined using the IMGT numbering scheme.

In particular embodiments of the invention, the Arginase 1 binder comprises (a) a VH2-CDR1 comprising the amino acid sequence set forth in SEQ ID NO: 25, a VH2-CDR2 comprising the amino acid sequence set forth in SEQ ID NO: 26, and a VH2-CDR3 comprising the amino acid sequence set forth in SEQ ID NO: 27; and (b) a VL-CDR1 comprising the amino acid sequence set forth in SEQ ID NO: 34, a VL-CDR2 comprising the amino acid sequence DA, and a VL-CDR3 comprising the amino acid sequence set forth in SEQ ID NO: 33. The Arginase 1 binders specifically bind arginase 1 and inhibit arginase 1 activity. CDR sequences are determined using the IMGT numbering scheme.

In particular embodiments of the invention, the Arginase 1 binder comprises (a) a VH1-CDR1 comprising the amino acid sequence set forth in SEQ ID NO: 15, a VH1-CDR2 comprising the amino acid sequence set forth in SEQ ID NO: 16, and a VH1-CDR3 comprising the amino acid sequence set forth in SEQ ID NO: 17; and (b) a VL-CDR1 comprising the amino acid sequence set forth in SEQ ID NO: 35, a VL-CDR2 comprising the amino acid sequence set forth in SEQ ID NO: 36, and a VL-CDR3 comprising the amino acid sequence set forth in SEQ ID NO: 37. The Arginase 1 binders specifically bind arginase 1 and inhibit arginase 1 activity. CDR sequences are determined by using the Contact numbering scheme.

In particular embodiments of the invention, the Arginase 1 binder comprises (a) a VH2-CDR1 comprising the amino acid sequence set forth in SEQ ID NO: 28, a VH2-CDR2 comprising the amino acid sequence set forth in SEQ ID NO: 29, and a VH2-CDR3 comprising the amino acid sequence set forth in SEQ ID NO: 30; and (b) a VL-CDR1 comprising the amino acid sequence set forth in SEQ ID NO: 35, a VL-CDR2 comprising the amino acid sequence set forth in SEQ ID NO: 36, and a VL-CDR3 comprising the amino acid sequence set forth in SEQ ID NO: 37. The Arginase 1 binders specifically bind arginase 1 and inhibit arginase 1 activity. CDR sequences are determined using the Contact numbering scheme.

In further embodiments, the Arginase 1 binder comprises a VH comprising the amino acid sequence set forth for VH1 in SEQ ID NO: 2 and a VL comprising the amino acid sequence set forth in SEQ ID NO: 4.

In further embodiments, the Arginase 1 binder comprises a VH comprising the amino acid sequence set forth for VH2 in SEQ ID NO: 3 and a VL comprising the amino acid sequence set forth in SEQ ID NO: 4.

In further embodiments of the invention, the Arginase 1 binder comprises a heavy chain constant domain of the IgG1, IgG2, IgG3, or IgG4 isotype. In particular embodiments, the heavy chain constant domain comprises 1, 2, 3, 4, 5, 6, 7, 8, 9, or 10 amino acid substitutions, additions, deletions, or combinations thereof compared to the amino acid sequence of the native IgG1, IgG2, IgG3, or IgG4 isotype, wherein the Arginase 1 binder specifically binds arginase 1 and inhibits arginase 1 activity.

In further embodiments, the arginase binder inhibits arginase 1 activity by at least 50%, 60%, 70%, 80%, or 90%. In further embodiments, the arginase binder inhibits arginase 1 activity at an $IC_{50}$ of less than 100 nM, 50 nM, 20 nM, or 10 nM. In a further embodiment, the $IC_{50}$ is about 3.3+/−0.3 nM or about 5.3+/−0.8 nM.

In further embodiments of the invention, the Arginase 1 binder comprises a heavy chain constant domain of the human IgG1 or IgG4 isotype. In particular embodiments, the heavy chain constant domain comprises 1, 2, 3, 4, 5, 6, 7, 8, 9, or 10 amino acid substitutions, additions, deletions, or combinations thereof compared to the amino acid sequence of the native IgG1 or IgG4 isotype, wherein the Arginase 1 binder specifically binds arginase 1 and inhibits arginase 1 activity. In a further aspect, the heavy chain constant domain is of the IgG4 isotype and further includes a substitution of the serine residue at position 228 (EU numbering) with proline, which corresponds to position 108 of SEQ ID NO: 52 (Serine at position 108).

In further aspects or embodiments of the invention, the antibody comprises a IgG1 heavy chain constant domain comprising the amino acid sequence shown in SEQ ID NO: 38 or a variant thereof comprising 1, 2, 3, 4, 5, 6, 7, 8, 9, or 10 amino acid substitutions, additions, deletions, or combinations thereof, wherein the Arginase 1 binder specifically binds arginase 1 and inhibits arginase 1 activity.

In further aspects or embodiments of the invention, the antibody comprises a IgG2 heavy chain constant domain comprising the amino acid sequence shown in SEQ ID NO: 46 and further comprising 1, 2, 3, 4, 5, 6, 7, 8, 9, or 10 amino acid substitutions, additions, deletions, or combinations thereof, wherein the Arginase 1 binder specifically binds arginase 1 and inhibits arginase 1 activity.

In further aspects or embodiments of the invention, the antibody comprises a IgG4 heavy chain constant domain comprising the amino acid sequence shown in SEQ ID NO: 53 and further comprising 1, 2, 3, 4, 5, 6, 7, 8, 9, or 10 amino acid substitutions, additions, deletions, or combinations thereof, wherein the Arginase 1 binder specifically binds arginase 1 and inhibits arginase 1 activity.

In particular embodiments of the invention, the constant domains as disclosed herein may comprise a C-terminal lysine or lack either a C-terminal lysine or a C-terminal glycine-lysine dipeptide.

In any one of the embodiments disclosed herein, the light chain may comprise a human kappa light chain constant domain comprising SEQ ID NO: 58 or a lambda light chain constant domain comprising SEQ ID NO: 64.

Arginase 1 Binders Comprising an Effector-Silent Fc Domain

Effector-silent Arginase 1 binders of the present invention are antibodies that comprise an HC constant domain or Fc domain thereof that has been modified such that the antibody displays no measurable binding to one or more FcRs or displays reduced binding to one or more FcRs compared to that of an unmodified antibody of the same IgG isotype. The effector-silent antibodies may in further embodiments display no measurable binding to each of FcγRIIIa, FcγRIIa, and FcγRI or display reduced binding to each of FcγRIIIa, FcγRIIa, and FcγRI compared to that of an unmodified antibody of the same IgG isotype. In particular embodiments, the HC constant domain or Fc domain is a human HC constant domain or Fc domain.

In particular embodiments, the effector-silent antibody comprises an Fc domain of an IgG1 or IgG2, IgG3, or IgG4 isotype that has been modified to lack N-glycosylation of the asparagine (Asn) residue at position 297 (Eu numbering system) of the HC constant domain. The consensus sequence for N-glycosylation is Asn-Xaa-Ser/Thr (wherein Xaa at position 298 is any amino acid except Pro); in all four isotypes the N-glycosylation consensus sequence is Asn-Ser-Thr. The modification may be achieved by replacing the codon encoding the Asn at position 297 in the nucleic acid molecule encoding the HC constant domain with a codon encoding another amino acid, for example Ala, Asp, Gln, Gly, or Glu, e.g. N297A, N297Q, N297G, N297E, or N297D. Alternatively, the codon for Ser at position 298 may be replaced with the codon for Pro or the codon for Thr at position 299 may be replaced with any codon except the codon for Ser. In a further alternative each of the amino acids comprising the N-glycosylation consensus sequence is replaced with another amino acid. Such modified IgG molecules have no measurable effector function. In particular embodiments, these mutated HC molecules may further comprise 1, 2, 3, 4, 5, 6, 7, 8, 9, or 10 additional amino acid substitutions, insertions, and/or deletions, wherein said substitutions may be conservative mutations or non-conservative mutations. In further embodiments, such IgGs modified to lack N-glycosylation at position 297 may further include one or more additional mutations disclosed herein for eliminating measurable effector function.

An exemplary IgG1 HC constant domain mutated at position 297, which abolishes the N-glycosylation of the HC constant domain, is set forth in SEQ ID NO: 44, an exemplary IgG2 HC constant domain mutated at position 297, which abolishes the N-glycosylation of the HC constant, is set forth in SEQ ID NO: 50, and an exemplary IgG4 HC constant domain mutated at position 297 to abolish N-glycosylation of the HC constant domain is set forth in SEQ ID NO: 56. In particular embodiments, these mutated HC molecules may further comprise 1, 2, 3, 4, 5, 6, 7, 8, 9, or 10 additional amino acid substitutions, insertions, and/or deletions, wherein said substitutions may be conservative mutations or non-conservative mutations.

In particular embodiments, the Fc domain of the IgG1 IgG2, IgG3, or IgG4 HC constant domain comprising the effector-silent antibody is modified to include one or more amino acid substitutions selected from E233P, L234A, L235A, L235E, N297A, N297D, D265S, and P331S (wherein the positions are identified according to Eu numbering) and wherein said HC constant domain is effector-silent. In particular embodiments, the modified IgG1 further comprise 1, 2, 3, 4, 5, 6, 7, 8, 9, or 10 additional amino acid substitutions, insertions, and/or deletions, wherein said substitutions may be conservative mutations or non-conservative mutations.

In particular embodiments, the HC constant domain comprises L234A, L235A, and D265S substitutions (wherein the positions are identified according to Eu numbering). In particular embodiments, the HC constant domain comprises an amino acid substitution at position Pro329 and at least one further amino acid substitution selected from E233P, L234A, L235A, L235E, N297A, N297D, D265S, and P331S (wherein the positions are identified according to Eu numbering). These and other substitutions are disclosed in WO9428027; WO2004099249; WO20121300831, U.S. Pat. Nos. 9,708,406; 8,969,526; 9,296,815; Sondermann et al. Nature 406, 267-273 (2000)).

In particular embodiments of the above, the HC constant domain comprises an L234A/L235A/D265A; L234A/L235A/P329G; L235E; D265A; D265A/N297G; or V234A/G237A/P238S/H268A/V309L/A330S/P331S substitutions, wherein the positions are identified according to Eu numbering. In particular embodiments, the HC molecules further comprise 1, 2, 3, 4, 5, 6, 7, 8, 9, or 10 additional amino acid substitutions, insertions, and/or deletions, wherein said substitutions may be conservative mutations or non-conservative mutations.

In particular embodiments, the effector-silent antibody comprises an IgG1 isotype, in which the Fc domain of the HC constant domain has been modified to be effector-silent by substituting the amino acids from position 233 to position 236 of the IgG1 with the corresponding amino acids of the human IgG2 HC and substituting the amino acids at positions 327, 330, and 331 with the corresponding amino acids of the human IgG4 HC, wherein the positions are identified according to Eu numbering (Armour et al., Eur. J. Immunol. 29(8):2613-24 (1999); Shields et al., J. Biol. Chem. 276(9): 6591-604(2001)). In particular embodiments, the modified IgG1 further comprise 1, 2, 3, 4, 5, 6, 7, 8, 9, or 10 additional amino acid substitutions, insertions, and/or deletions, wherein said substitutions may be conservative mutations or non-conservative mutations.

In particular embodiments, the effector-silent antibody comprises a VH fused or linked to a hybrid human immunoglobulin HC constant domain, which includes a hinge region, a CH2 domain and a CH3 domain in an N-terminal to C-terminal direction, wherein the hinge region comprises an at least partial amino acid sequence of a human IgD hinge region or a human IgG1 hinge region; and the CH2 domain is of a human IgG4 CH2 domain, a portion of which, at its N-terminal region, is replaced by 4-37 amino acid residues of an N-terminal region of a human IgG2 CH2 or human IgD CH2 domain. Such hybrid human HC constant domain is disclosed in U.S. Pat. No. 7,867,491, which is incorporated herein by reference in its entirety.

In particular embodiments, the effector-silent antibody comprises an IgG4 HC constant domain in which the serine at position 228 according to the Eu system is substituted with proline, see for example SEQ ID NO: 52. This modification prevents formation of a potential inter-chain disulfide bond between the cysteines at positions Cys226 and Cys229 in the EU numbering scheme and which may interfere with proper intra-chain disulfide bond formation. See Angal et al. Mol. Imunol. 30:105 (1993); see also (Schuurman et al., Mol. Immunol. 38: 1-8, (2001)). In further embodiments, the IgG4 constant domain includes in addition to the S228P substitution, a P239G, D265A, or D265A/N297G amino acid substitution, wherein the positions are identified according to Eu numbering. In particular embodiments of the above, the IgG4 HC constant domain is a human HC constant domain. In particular embodiments, the HC molecules further comprise 1, 2, 3, 4, 5, 6, 7, 8, 9, or 10 additional amino acid substitutions, insertions, and/or deletions, wherein said substitutions may be conservative mutations or non-conservative mutations.

Exemplary IgG1 HC constant domains include HC constant domains comprising an amino acid sequence selected from the group consisting of amino acid sequences set forth in SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 58, and SEQ ID NO: 59. Exemplary IgG2 HC constant domains have an amino acid sequence selected from the group consisting of amino acid sequences set forth in SEQ ID NO: 47, SEQ ID NO: 48, SEQ ID NO: 49, SEQ ID NO: 50, SEQ ID NO: 51, and SEQ ID NO: 52. Exemplary IgG4 HC constant domains have an amino acid sequence selected from the group consisting of amino acid sequences set forth in SEQ ID NO: 54, SEQ ID NO: 55, SEQ ID NO: 56, and SEQ ID NO: 57.

In particular embodiments of the Arginase 1 binder, the Arginase 1 binder is an antibody comprising an IgG1, IgG2, or IgG4 Fc domain as disclosed herein, which further comprises a C-terminal lysine or lack either a C-terminal lysine or a C-terminal glycine-lysine dipeptide.

In any one of the embodiments disclosed herein, the light chain may comprise a human kappa light chain constant domain comprising SEQ ID NO: 58 or a lambda light chain constant domain comprising SEQ ID NO: 64.

Nucleic Acid Molecules Encoding the Arginase 1 Binders

The present invention further provides nucleic acid molecules that encode the Arginase 1 binders of the present invention. In particular embodiments, the Arginase 1 binder comprises a VH1 or VH2 domain encoded by a nucleic acid molecule comprising the nucleotide sequence set forth in SEQ ID NO: 65 or SEQ ID NO: 66, respectively. In a further embodiment, Arginase 1 binder further comprises a VL encoded by a nucleic acid molecule comprising the nucleotide sequence set forth in SEQ ID NO: 67.

In further embodiments, the Arginase 1 binder comprises a VH1 or VH2 domain encoded by a nucleic acid molecule comprising the nucleotide sequence set forth in SEQ ID NO: 65 or SEQ ID NO: 66, respectively, and a VL encoded by a nucleic acid molecule comprising the nucleotide sequence set forth in SEQ ID NO: 67.

In further embodiments, the Arginase 1 binder comprises a VH1 or VH2 domain encoded by a nucleic acid molecule comprising the nucleotide sequence set forth in SEQ ID NO: 65 or SEQ ID NO: 66, respectively, and a VL encoded by a nucleic acid molecule comprising the nucleotide sequence set forth in SEQ ID NO: 67, wherein the nucleic acid molecule encoding the VH1 or VH2 is linked to a nucleic acid molecule encoding an IgG1, IgG2, IGG3, or IgG4 heavy chain constant domain and the nucleic acid molecule encoding the VL is linked to a nucleic acid molecule encoding kappa or lambda light chain constant domain.

Exemplary IgG1 heavy chain constant domains may be encoded by a nucleic acid molecule comprising the nucleotide sequence set forth in SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 89, or SEQ ID NO: 90.

Exemplary IgG2 heavy chain constant domains may be encoded by a nucleic acid molecule comprising the nucleotide sequence set forth in SEQ ID NO: 76, SEQ ID NO: 77, SEQ ID NO: 78, SEQ ID NO: 79, SEQ ID NO: 80, SEQ ID NO: 81, or SEQ ID NO: 82.

Exemplary IgG4 heavy chain constant domains may be encoded by a nucleic acid molecule comprising the nucleotide sequence set forth in SEQ ID NO: 83, SEQ ID NO: 84, SEQ ID NO: 85, SEQ ID NO: 86, or SEQ ID NO: 87.

Exemplary light chain constant domains may be encoded by a nucleic acid molecule comprising the nucleotide sequence set forth in SEQ ID NO: 88 or SEQ ID NO: 91.

In particular embodiments, the HC and LC (or VH and VL) are expressed as a fusion protein in which the N-terminus of the HC and the LC (or VH and VL) are fused to a leader peptide to facilitate the transport of the antibody through the secretory pathway. Examples of leader peptides that may be used include MSVPTQVLGLLLLWLTDARC (SEQ ID NO: 95) encoded by the nucleotide sequence set forth in SEQ ID NO: 97 or MEWSWVFLFFLSVTTGVHS (SEQ ID NO: 96) encoded by the nucleotide sequence set forth in SEQ ID NO: 98. Thus, in particular embodiments, the aforementioned nucleic acid molecules may comprise a polynucleotide encoding a leader peptide linked to the 5' end of the nucleic acid molecule.

The nucleic acid molecules disclosed herein may include one or more substitutions that optimize one or more of the codons for enhancing the expression of the nucleic acid molecule in a particular host cell, e.g., yeast or fungal host cell, non-human mammalian hot cell, human host cell, insect host cell, or prokaryote host cell. Methods and computer programs for optimizing a nucleic acid molecule for enhancing expression in a particular host cell are well known in the art, e.g. the IDT Codon Optimization Tool commercially available from Integrated DNA Technologies, Inc. 1710 Commercial Park, Coralville, Iowa 52241, USA.; U.S. Pat. No. 8,326,547; WO2020024917A1.

Methods for Making Arginase 1 Binders

The present invention includes recombinant methods for making Arginase 1 binders comprising introducing into a host cell (i) an expression vector that encodes the VH and VL of an Arginase 1 binder or the HC and LC of an Arginase 1 binder, or (ii) two expression vectors, one encoding the VH of an Arginase 1 binder or the HC of an Arginase 1 binder the other encoding the VL of an Arginase 1 binder or the LC of an Arginase 1 binder. The nucleic acid molecules or polynucleotides encoding the VH, VL, HC, or LC are operably linked to a promoter and other transcription and translation regulatory sequences (as used herein "VH" refers to either VH1 or VH2). The host cell is cultured under conditions and a time period suitable for expression of the nucleic acid molecules followed by isolating the Arginase 1 binder from the host cell and/or medium in which the host cell is grown. See e.g., WO 04/041862, WO 2006/122786, WO 2008/020079, WO 2008/142164 or WO 2009/068627. The expression vector may be a plasmid or viral vector. The invention also relates to hosts or host cells that contain such nucleic acid molecule encoding the Arginase 1 binders or components thereof, e.g., solely the VH or HC or solely the VL or HC Eukaryotic and prokaryotic host cells, including mammalian cells as hosts for expression of the Arginase 1 binder are well known in the art and include many immortalized cell lines available from the American Type Culture Collection (ATCC). These include, but are not limited to, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Thus, mammalian host cells include human, mouse, rat, dog, monkey, pig, goat, bovine, horse and hamster cells. Cell lines of particular preference are selected through determining which cell lines have high expression levels. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia pastoris, Saccharomyces cervisiea*, and *Trichoderma reesei*. The present invention includes any host cell comprising an Arginase 1 binder of the present invention or comprising one or more nucleic acid molecules encoding such an Arginase 1 binder or comprising an expression vector that comprises one or more nucleic acid molecules encoding such Arginase 1 binder.

Further, expression of an Arginase 1 binder from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4. Thus, in an embodiment of the invention, the mammalian host cells lack a glutamine synthetase gene and are grown in the absence of glutamine in the medium wherein, however, the nucleic acid molecule encoding the immunoglobulin chain comprises a glutamine synthetase gene which complements the lack of the gene in the host cell. Such host cells containing the Arginase 1binder or nucleic acid(s) or expression vector(s) as discussed herein as well as expression methods, as discussed herein, for making the Arginase 1 binder using such a host cell are part of the present invention.

The present invention includes methods for purifying an Arginase 1 binder comprising introducing a sample (e.g., culture medium, cell lysate or cell lysate fraction, e.g., a soluble fraction of the lysate) comprising the Arginase 1 binder to a purification medium (e.g., cation-exchange medium, anion-exchange medium and/or hydrophobic exchange medium) and either collecting purified Arginase 1 binder from the flow-through fraction of said sample that does not bind to the medium; or, discarding the flow-through fraction and eluting bound Arginase 1 binder from the medium and collecting the eluate. In an embodiment of the invention, the medium is in a column to which the sample is applied. In an embodiment of the invention, the purification method is conducted following recombinant expression of the Arginase 1 binder in a host cell, e.g., wherein the host cell is first lysed and, optionally, the lysate is purified of insoluble materials prior to purification on a medium; or wherein the Arginase 1 binder is secreted into the culture medium by the host cell and the medium or a fraction thereof is applied to the purification medium.

In general, glycoproteins produced in a particular cell line or transgenic animal will have a glycosylation pattern that is characteristic for glycoproteins produced in the cell line or transgenic animal. Therefore, the particular glycosylation pattern of an Arginase 1 binder will depend on the particular cell line or transgenic animal used to produce the Arginase 1 binder. Arginase 1 binders comprising only non-fucosylated N-glycans are part of the present invention and may be advantageous, because non-fucosylated antibodies have been shown to typically exhibit more potent efficacy than their fucosylated counterparts both in vitro and in vivo (See for example, Shinkawa et al., J. Biol. Chem. 278: 3466-3473 (2003); U.S. Pat. Nos. 6,946,292 and 7,214,775). These Arginase 1binders with non-fucosylated N-glycans are not likely to be immunogenic because their carbohydrate structures are a normal component of the population that exists in human serum IgG.

Figure 8:
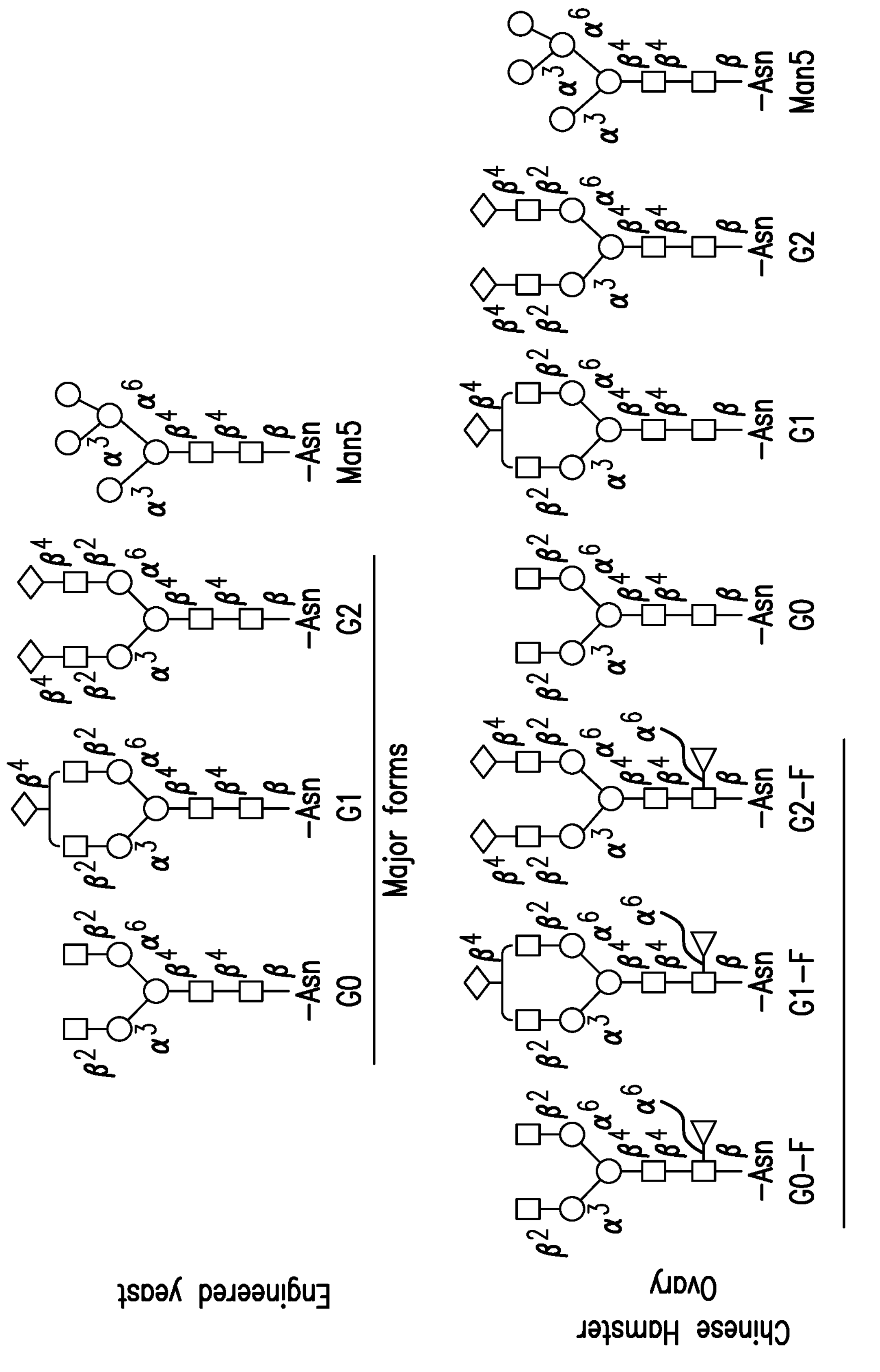
FIG. 8. Predominant N-linked glycans for monoclonal antibodies produced in Chinese hamster ovary cells (CHO N-linked glycans) and in engineered yeast cells (engineered yeast N-linked glycans): squares: N-acetylglucosamine (GlcNac); circles: mannose (Man); diamonds: galactose (Gal); triangles: fucose (Fuc).

The present invention includes Arginase 1 binders comprising N-linked glycans that are typically added to immunoglobulins produced in Chinese hamster ovary cells (CHO N-linked glycans) or to engineered yeast cells (engineered yeast N-linked glycans), such as, for example, *Pichia pastoris*. For example, in an embodiment of the invention, the Arginase 1 binder comprises one or more of the "engineered yeast N-linked glycans" or "CHO N-linked glycans" (e.g., G0 and/or G0-F and/or G1 and/or GT-F and/or and/or G2-F and/or Man5, see FIG. 8). In an embodiment of the invention, the Arginase 1binder comprises the engineered yeast N-linked glycans, i.e., G0 and/or G1 and/or G2, optionally, further including Man5. In an embodiment of the invention, the Arginase 1 binders comprise the CHO N-linked glycans, i.e., G0-F, G1-F and G2-F, optionally, further including G0 and/or G1 and/or G2 and/or Man5. In an embodiment of the invention, about 80% to about 95% (e.g., about 80-90%, about 85%, about 90% or about 95%) of all N-linked glycans on the Arginase 1 binders are engineered yeast N-linked glycans or CHO N-linked glycans. See Nett et al. Yeast. 28(3): 237-252 (2011); Hamilton et al. Science. 313(5792): 1441-1443 (2006); Hamilton et al. Curr Opin Biotechnol. 18(5): 387-392 (2007). For example, in an embodiment of the invention, an engineered yeast cell is GFI5.0 or YGLY8316 or strains set forth in U.S. Pat. No. 7,795,002 or Zha et al. Methods Mol Biol. 988:31-43 (2013). See also international patent application publication no. WO2013/066765.

Administration Pharmaceutical Compositions

The Arginase 1 binder may be provided in suitable pharmaceutical compositions comprising the Arginase 1 binder and a pharmaceutically acceptable carrier. The carrier may be a diluent, adjuvant, excipient, or vehicle with which the Arginase 1 binder is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules or of the invention in such pharmaceutical formulation may vary widely, i.e., from less than about 0.5%, usually to at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21.sup.st Edition, Troy, D. B. ed., Lipincott Williams and Wilkins, Philadelphia, Pa. 2006, Part 5, Pharmaceutical Manufacturing pp 691-1092, see especially pp. 958-989.

The mode of administration of the Arginase 1 binder may be any suitable route such as parenteral administration, e.g., intradermal, intramuscular, intraperitoneal, intravenous or subcutaneous, pulmonary, transmucosal (oral, intranasal, intravaginal, rectal) or other means appreciated by the skilled artisan, as well known in the art.

The Arginase 1 binder may be administered to an individual (e.g., patient) by any suitable route, for example parentally by intravenous (i.v.) infusion or bolus injection, intramuscularly or subcutaneously, or intraperitoneally. i.v. infusion may be given over for, example, 15, 30, 60, 90, 120, 180, or 240 minutes, or from 1, 2, 3, 4, 5, 6, 7, 8, 9, 10, 11 or 12 hours.

The dose given to an individual having cancer or malignancy is sufficient to alleviate or at least partially arrest the disease being treated ("therapeutically effective amount") and may be sometimes 0.005 mg/kg to about 100 mg/kg, e.g. about 0.05 mg/kg to about 30 mg/kg or about 5 mg to about 25 mg/kg, or about 4 mg/kg, about 8 mg/kg, about 16 mg/kg or about 24 mg/kg, or, e.g., about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 $mg/m^2$. Usually between 1 and 8 doses, (e.g., 1, 2, 3, 4, 5, 6, 7 or 8) may be administered to treat cancer or malignancy, but 9, 10, 11, 12, 13, 14, 15, 16, 17, 18, 19, 20 or more doses may be given.

The administration of the Arginase 1 binder may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the Arginase 1 binder in the methods of the invention may be administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

The Arginase 1 binder may be administered by maintenance therapy, such as, e.g., once a week for a period of 6 months or more. For example, Arginase 1 binder in the methods of the invention may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

The Arginase 1 binder may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

The Arginase 1 binder may be lyophilized for storage and reconstituted in a suitable carrier prior to use. This technique has been shown to be effective with conventional protein preparations and well known lyophilization and reconstitution techniques can be employed.

Combination Therapy Treatments

The combination therapy of the present invention comprises an Arginase 1 binder and another therapeutic agent (small molecule or antibody) may be used for the treatment any proliferative disease, in particular, treatment of cancer. In particular embodiments, the combination therapy of the present invention may be used to treat melanoma, non-small cell lung cancer, head and neck cancer, urothelial cancer, breast cancer, gastrointestinal cancer, multiple myeloma, hepatocellular cancer, non-Hodgkin lymphoma, renal cancer, Hodgkin lymphoma, mesothelioma, ovarian cancer, small cell lung cancer, esophageal cancer, anal cancer, biliary tract cancer, colorectal cancer, cervical cancer, thyroid cancer, or salivary cancer.

In another embodiment, the combination therapy of the present invention may be used to treat pancreatic cancer, bronchus cancer, prostate cancer, pancreatic cancer, stomach cancer, ovarian cancer, urinary bladder cancer, brain or central nervous system cancer, peripheral nervous system cancer, uterine or endometrial cancer, cancer of the oral cavity or pharynx, liver cancer, kidney cancer, testicular cancer, biliary tract cancer, small bowel or appendix cancer, adrenal gland cancer, osteosarcoma, chondrosarcoma, or cancer of hematological tissues.

Combination Therapy Comprising an Arginase 1 Binder and a Chemotherapy Agent

The combination therapy of the present invention may be administered to an individual having a cancer in combination with chemotherapy. The individual may undergo the chemotherapy at the same time the individual is undergoing the combination therapy of the present invention. The individual may undergo the combination therapy of the present invention after the individual has completed chemotherapy. The individual may be administered the chemotherapy after completion of the combination therapy. The combination therapy of the present invention may also be administered to an individual having recurrent or metastatic cancer with disease progression or relapse cancer and who is undergoing chemotherapy or who has completed chemotherapy.

The chemotherapy may include a chemotherapy agent selected from the group consisting of (i) alkylating agents, including but not limited to, bifunctional alkylators, cyclophosphamide, mechlorethamine, chlorambucil, and melphalan;

(ii) monofunctional alkylators, including but not limited to, dacarbazine, nitrosoureas, and temozolomide (oral dacarbazine);

(iii) anthracyclines, including but not limited to, daunorubicin, doxorubicin, epirubicin, idarubicin, mitoxantrone, and valrubicin;

(iv) cytoskeletal disruptors (taxanes), including but not limited to, paclitaxel, docetaxel, abraxane, and taxotere;

(v) epothilones, including but not limited to, ixabepilone, and utidelone;

(vi) histone deacetylase inhibitors, including but not limited to, vorinostat, and romidepsin;

(vii) inhibitors of topoisomerase i, including but not limited to, irinotecan, and topotecan;

(viii) inhibitors of topoisomerase ii, including but not limited to, etoposide, teniposide, and tafluposide;

(ix) kinase inhibitors, including but not limited to, bortezomib, erlotinib, gefitinib, imatinib, vemurafenib, and vismodegib;

(x) nucleotide analogs and precursor analogs, including but not limited to, azacitidine, azathioprine, fluoropyrimidines (e.g., such as capecitabine, carmofur, doxifluridine, fluorouracil, and tegafur) cytarabine, gemcitabine, hydroxyurea, mercaptopurine, methotrexate, and tioguanine (formerly thioguanine);

(xi) peptide antibiotics, including but not limited to, bleomycin and actinomycin; a platinum-based agent, including but not limited to, carboplatin, cisplatin, and oxaliplatin;

(xii) retinoids, including but not limited to, tretinoin, alitretinoin, and bexarotene; and xiii) vinca alkaloids and derivatives, including but not limited to, vinblastine, vincristine, vindesine, and vinorelbine.

Selecting a dose of the chemotherapy agent for chemotherapy depends on several factors, including the serum or tissue turnover rate of the entity, the level of symptoms, the immunogenicity of the entity, and the accessibility of the target cells, tissue or organ in the individual being treated. The dose of the additional therapeutic agent should be an amount that provides an acceptable level of side effects. Accordingly, the dose amount and dosing frequency of each additional therapeutic agent will depend in part on the particular therapeutic agent, the severity of the cancer being treated, and patient characteristics. Guidance in selecting appropriate doses of antibodies, cytokines, and small molecules are available. See, e.g., Wawrzynczak (1996) Antibody Therapy, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert et al. (2003) *New Engl. J Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J Med.* 342:613-619; Ghosh et al. (2003) *New Engl. J Med.* 348:24-32; Lipsky et al. (2000) *New Engl. J Med.* 343:1594-1602; Physicians' Desk Reference 2003 (Physicians' Desk Reference, 57th Ed); Medical Economics Company; ISBN: 1563634457; 57th edition (November 2002). Determination of the appropriate dose regimen may be made by the clinician, e.g., using parameters or factors known or suspected in the art to affect treatment or predicted to affect treatment, and will depend, for example, the individual's clinical history (e.g., previous therapy), the type and stage of the cancer to be treated and biomarkers of response to one or more of the therapeutic agents in the combination therapy.

Thus, the present invention contemplates embodiments of the combination therapy of the present invention that further includes a chemotherapy step comprising platinum-containing chemotherapy, pemetrexed and platinum chemotherapy or carboplatin and either paclitaxel or nab-paclitaxel. In particular embodiments, the combination therapy with a chemotherapy step may be used for treating at least NSCLC and HNSCC.

The combination therapy further in combination with a chemotherapy step may be used for the treatment any proliferative disease, in particular, treatment of cancer. In particular embodiments, the combination therapy of the present invention may be used to treat melanoma, non-small cell lung cancer, head and neck cancer, urothelial cancer, breast cancer, gastrointestinal cancer, multiple myeloma, hepatocellular cancer, non-Hodgkin lymphoma, renal cancer, Hodgkin lymphoma, mesothelioma, ovarian cancer, small cell lung cancer, esophageal cancer, anal cancer, biliary tract cancer, colorectal cancer, cervical cancer, thyroid cancer, or salivary cancer.

In another embodiment, the combination therapy further in combination with a chemotherapy step may be used to treat pancreatic cancer, bronchus cancer, prostate cancer, pancreatic cancer, stomach cancer, ovarian cancer, urinary bladder cancer, brain or central nervous system cancer, peripheral nervous system cancer, uterine or endometrial cancer, cancer of the oral cavity or pharynx, liver cancer, kidney cancer, testicular cancer, biliary tract cancer, small bowel or appendix cancer, adrenal gland cancer, osteosarcoma, chondrosarcoma, or cancer of hematological tissues.

In particular embodiments, the combination therapy with a chemotherapy step may be used to treat one or more cancers selected from melanoma (metastatic or unresectable), primary mediastinal large B-cell lymphoma (PMBCL), urothelial carcinoma, MSIHC, gastric cancer, cervical cancer, hepatocellular carcinoma (HCC), Merkel cell carcinoma (MCC), renal cell carcinoma (including advanced), and cutaneous squamous carcinoma.

Combination Therapy Comprising an Arginase 1 Binder and a Therapeutic Antibody

The Arginase 1 binder of the present invention may be administered in combination with one or more therapeutic agent, which is an antibody, for treatment of cancer or proliferative disease. The individual may undergo treatment with the therapeutic antibody at the same time the individual is undergoing the combination therapy of the present invention. The individual may undergo the combination therapy of the present invention after the individual has completed treatment with the therapeutic antibody. The individual may be administered the treatment with the therapeutic antibody after completion of the combination therapy. The combination therapy of the present invention may also be administered to an individual having recurrent or metastatic cancer with disease progression or relapse cancer and who is undergoing chemotherapy or who has completed chemotherapy. In particular embodiments, the therapeutic agent targets the programmed death 1 receptor or ligand., PD-1 and PD-L1, respectively.

Exemplary anti-PD-1 antibodies that may be used in a combination therapy with the Arginase 1 binder include any antibody that binds PD-1 and inhibits PD-1 from binding PD-L1. In a further embodiment, the exemplary anti-PD-1 antibody is selected from the group consisting of nivolumab, pembrolizumab, and cemiplimab-rwlc. Exemplary antibodies include the following anti-PD-1 antibodies and compositions comprising an anti-PD1 antibody and a pharmaceutically acceptable salt.

Pembrolizumab, also known as KEYTRUDA, lambrolizumab, MK-3475 or SCH-900475, is a humanized anti-PD-1 antibody described in U.S. Pat. No. 8,354,509 and WO2009/114335 and disclosed, e.g., in Hamid, et al., New England J. Med. 369 (2): 134-144 (2013).

Nivolumab, also known as OPDIVO, MDX-1106-04, ONO-4538, or BMS-936558, is a fully human IgG4 anti-PD-1 antibody described in WO2006/121168 and U.S. Pat. No. 8,008,449.

Cemiplimab-rwlc, also known as cemiplimab, LIBTAYO or REGN2810, is a recombinant human IgG4 monoclonal antibody that is described in WO2015112800 and U.S. Pat. No. 9,987,500.

In particular embodiments, the anti-PD-1 antibody comprises (i) a VH comprising the three HC-CDRs of pembrolizumab fused or linked to an effector-silent HC constant domain and (ii) a VL comprising the three LC-CDRs of pembrolizumab fused or linked to a LC kappa or lambda constant domain.

In particular embodiments, the anti-PD-1 antibody comprises (i) a VH comprising the three HC-CDRs of nivolumab fused or linked to an effector-silent HC constant domain and (ii) a VL comprising the three LC-CDRs of nivolumab fused or linked to a LC kappa or lambda constant domain.

In particular embodiments, the anti-PD-1 antibody comprises (i) a VH comprising the three HC-CDRs of cemiplimab-rwlc fused or linked to an effector-silent HC constant domain and (ii) a VL comprising the three LC-CDRs of nivolumab fused or linked to a LC kappa or lambda constant domain.

In particular embodiments, the anti-PD-1 antibody VH may be fused or linked to an IgG1, IgG2, IgG3, or IgG4 HC constant domain that is not currently linked to the particular VH or is linked to an IgG1, IgG2, IgG3, or IgG4 HC constant domain has been modified to include one or more mutations in the Fc domain that render the resulting anti-PD-1 antibody effecter-silent.

Injection device for administering an Arginase 1 binder

The present invention also provides an injection device comprising an Arginase 1 binder as set forth herein or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., comprising the Arginase 1 binder or a pharmaceutical composition thereof), a needle for piecing skin and/or blood vessels for injection of the fluid; and a plunger for pushing the fluid out of the cylinder and through the needle bore. In an embodiment of the invention, an injection device that comprises an Arginase 1 binder or a pharmaceutical composition thereof is an intravenous (IV) injection device. Such a device includes the Arginase 1 binder or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$) and optionally including glucose) introduced into the body of the subject through the cannula or trocar/needle.

The Arginase 1 binder or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrowjet of liquid which penetrate the epidermis to introduce the Arginase 1 binder or a pharmaceutical composition thereof to a patient's body. External infusion pumps are medical devices that deliver the Arginase 1 binder or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

Kits Comprising an Arginase 1 Binder

Further provided are kits comprising one or more components that include, but are not limited to, an Arginase 1 binder, as discussed herein in association with one or more additional components including, but not limited to, a further therapeutic agent, as discussed herein. The Arginase 1 binder and/or the therapeutic agent can be formulated as a pure composition or in combination with a pharmaceutically acceptable carrier, in a pharmaceutical composition.

In one embodiment, the kit includes an Arginase 1 binder or a pharmaceutical composition thereof in one container (e.g., in a sterile glass or plastic vial) and a further therapeutic agent in another container (e.g., in a sterile glass or plastic vial).

In another embodiment, the kit comprises a combination of the invention, including an Arginase 1 binder or pharmaceutical composition thereof in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above. Thus, the present invention includes a kit comprising an injection device and the Arginase 1 binder, e.g., wherein the injection device includes Arginase 1 binder or wherein the Arginase 1 binder is in a separate vessel.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

The following examples are intended to promote a further understanding of the present invention.

Example 1

Expression and Purification of hArg1

Full-length untagged hArg1 was expressed in *E. coli* BL21 (DE3) cells using superbroth media. Expression was induced with 1 mM Isopropyl β-d-1-thiogalactopyranoside (IPTG) at $OD_{600}$ of 0.8 and cells were grown for four hours at 37° C. Cell pellets were resuspended in lysis buffer (10 mM Tris pH 7.5, 5 mM $MnCl_2$, 2 mM beta-mercaptoethanol (BME), 1 mg/mL lysozyme), passed through a microfluidizer three times at 15,000 pounds per square inch (PSI) and the soluble fraction was clarified by centrifugation at 11,000×g. Clarified lysates were heat treated at 60° C. for 20 minutes. Heat treated lysates were passed through a HiTRAP-SP column (GE). Flow through containing hArg1 was diluted to about 40 mM NaCl and reloaded on another HiTRAP-SP column. hArg1 was eluted from the column using a linear gradient from 20 mM NaCl to 1 M NaCl. Pooled fractions were concentrated and loaded on a HiLoad Superdex 200 26/60 size exclusion column in 25 mM HEPES pH 7.3, 150 mM NaCl, 1 mM MnCl. Peak fractions were analyzed by SDS-PAGE, pooled and concentrated. Purification adapted from Strickland Acta Cryst. (2011). F67, 90-93.

Example 2

Antibody Discovery and Optimization

De novo antibody discovery for identifying the fully human antibody against hArg1 used to construct mAb1, mAb2, and mAb3 were executed on pre-immune yeast display libraries with a diversity of $10^{10}$ (Sivasubramanian et al., *MAbs* 9: 29-42. (2017)). Briefly, a yeast IgG library was subjected to multiple rounds of selection by magnetic and florescence activated cell sorting (BD ARIA III) in phosphate buffered saline (PBS) buffer containing 1 mM $MnCl_2$. Selections were performed using 100 nM hArg1 followed by rounds of enrichment using decreased antigen concentrations to enhance for higher affinity binders. Top clones were isolated by affinity maturing its parental clone through shuffling the light chain and optimizing heavy chain CDR1 and CDR2 sequences. The selection of optimization libraries was repeated using 10 nM arginase 1 and the isolated clones were then sequenced to identify the unique antibodies and screened for binding profiles by Octet Red.

Antibody mAb1 is a chimeric antibody comprising the human VH1 and VL obtained from the fully human antibody identified from the yeast display libraries that binds hArg1 on a mouse IgG2a/kappa constant domain backbone. Antibody mAb2 is a chimeric antibody comprising the same human VH1 and VL on a mouse IgG1 D265A/kappa constant domain backbone. Antibody mAb3 is a chimeric antibody comprising human VH2 and VL on a human IgG4 P228/kappa constant domain backbone wherein the human VH2 is an affinity matured variant of the human VH1 and the VL is the same (FIGS. 1A-1D). The soluble proteins used in the yeast display selections were biotinylated recombinant proteins. All proteins were analytically and verified by size-exclusion chromatography (SEC) and sodium dodecyl sulfate polyacrylamide gel electrophoresis (SDS-PAGE).

Example 3

Antibody Production

ExpiCHO-S cells growing in suspension were transfected with antibody expression plasmids (HC+LC) using commercially available protocols and ExpiFectamine CHO reagents (Thermo-Fisher) (Sivasubramanian et al., op. cit.)). In brief, cells were transfected day 0 using 1 μg total DNA (3:2 ratio LC:HC) per 1 mL cells at a density of 6 million cells per mL and a viability >95% measured using a Vi-Cell (Beckman-Coulter). On day one, ExpiCHO feed and enhancer were added and culture temperature was lowered to 32° C. On day five, a second EXPI-CHO feed was performed and cell viability was measured using a Vi-Cell (Beckman-Coulter). Cultures were harvested between day 8and day 12 depending on a cell viability greater than 80%. Antibody was purified from clarified supernatant using Protein A chromatography (mAbSelect Sure LX, GE Healthcare). Protein A was incubated with the clarified supernatant overnight in 4° C. on a roller mixer. Resin was then collected from supernatant mixture and transferred into a column and washed with 10 column volumes (CV) of PBS. Elution of antibody was achieved using 20 mM sodium acetate, pH 3.5. One column volume (CV) fractions were collected and tested by Bradford assay to determine presence of protein. In some cases, Protein A purification was followed by anion exchange chromatography (Capto Q, GE Healthcare). Purified antibodies were buffer exchanged into the final formulation buffer of 20 mM sodium acetate, 9% sucrose, pH 5.5. Purified antibody was checked for purity by reduced and non-reduced Capillary electrophoresis sodium dodecyl sulfate (CE-SDS) (Perkin-Elmer), concentration was measured by A280, and aggregate content was analyzed by size exclusion ultra performance liquid chromatography (SEC-UPLC) using a BEH200 UPLC-SEC analytical column (Waters corporation). Endotoxin was quantified using Endosafe® nexgen-MCS™ (Charles River). Intact mass was confirmed via Synapt G2S QTOF or Xevo-TOF (Waters).

Example 4

Antibody Potency and Mechanism of hArg1 Inhibition

To evaluate antibody potency and mechanism of hArg1 inhibition, the antibodies to be tested were diluted in assay buffer (50 mM Tris pH 7.5, 50 mM sodium chloride, 1 mM MnCl, and 0.05% bovine serum albumin) to a concentration 2.5-fold higher than desired assay concentrations. To each well of a Greiner black 384-well assay plate (catalog #781086) was added 10 μL of antibody solution followed by 10 μL of assay buffer or assay buffer with 1 nM human or mouse Arg1. After 30 minutes of incubation at room temperature, 5 μL of a 5× solution of thioarginine (variable concentrations) was added. The assay was allowed to proceed for 60 minutes then quenched by addition of 15 μL of a solution of 375 μM 7-Diethylamine-3-(4-maleimidophenyl)-4-methylcoumarin (Sigma Chemical) in 70% ethanol to quench the reaction and detect thioornithine. The plate was briefly shaken to mix and the fluorescence was measured in a Spectramax plate reader (Molecular Devices) with a 410 nm excitation wavelength and a 490 nm emission wavelength. Kinetic data were fit to various models of enzyme inhibition (competitive, mixed, noncompetitive, and uncompetitive) using GraphPad Prism.

An alternate assessment of antibody potency was performed by serially diluting antibodies in assay buffer and performing the assay described above except that a fixed concentration of 1 mM thioarginine was used. Data were normalized to wells containing either no antibody (no effect control) or no arginine (max effect control). The percent inhibition was then fit to a four-parameter logistic equation in GraphPad Prism to determine the IC50.

Potency and MOI for mAb1 and mAb2 are shown in FIG. 2.

Example 5

Determination of hArg1 Activity by Liquid Chromatography-Mass Spectroscopy (LC-MS)

Arginase enzyme was diluted to 1.25 nM in assay buffer containing 50 mM Tris pH 7.5, 50 mM NaCl, 1 mM $MnCl_2$ and 0.05% Bovine serum albumin and 20 μL of the dilution were added to black 384 well assay plates (Greiner Bio-One Inc., Monroe, CA). Titrations of antibodies were added to appropriate wells on the plate, following which samples were incubated at 37° C. for 30 minutes in an oven. The arginine substrate was diluted in assay buffer to 1.5 mM and 5 μL were added into assay plate (final substrate concentration=300 μM). The reaction was carried out for one hour at 37° C. At the end of the reaction, 15 μL of ethanol containing internal standards (40 μM [$^{13}$C6]-Arginine and [$^{13}$C5]-Ornithine) were added to the mixture to quench the reaction. The assay plate was then stored at −80° C. until sample derivatization.

Then, 10 μL of thawed sample were transferred from the assay plate to a 384 deep-well plate and 90 μL methanol were added. Samples were centrifuged at 2,500 rpm for 10 minutes at room temperature and five μL of supernatant were transferred to a fresh 384 well SiliGuard-coated plate containing 35 μL of neat borate buffer. AccQ-Tag Ultra reagent (Waters Corporation, Milford, MA) was initially prepared according to the manufacturer's instructions and then diluted an additional two-fold with acetonitrile. Then, 10 mL of the reconstituted AccQ-Tag were added to each well and plates were sealed with pierceable aluminum foil (Agilent Technologies, Santa Clara, CA). The derivatization reaction was carried out by incubating at 55° C. in an oven for 30 minutes. Plates were then stored at 4° C. prior to LC-MS analysis.

Samples were analyzed on a Thermo TSQ Vantage triple quadrupole mass spectrometer with an electrospray ionization source operating in the positive ion mode (Thermo Fisher Scientific; Waltham, MA). Separation was achieved using an Acquity UPLC HSS-T3 2.1×30 mm, 1.8 μM column (Waters Corporation, Milford, MA) at ambient temperature. A binary solvent system composed of 0.1% formic acid in $H_2O$ (mobile phase A) and 0.1% formic acid in acetonitrile (mobile phase B) was used for chromatographic separation. Selected reaction monitoring was used to quantify the analytes and internal standards, with the specific precursor to product transitions of Arginine (344.96>70.14), [$^{13}$C6]Arginine (351.102>74.3), Ornithine (473.29>171.15), [$^{13}$C5]Ornithine (478.29>171.15). During analysis, samples were maintained at 10° C. in the autosampler chamber. For injection, 12 μL of sample were over-filled into a 5 μL sample loop. All results were analyzed using the response ratio of analyte peak area/internal standard peak area for data normalization.

FIG. 3 shows dose response curves for mAb1 and mAb2 as determined by LCMS.

Example 6

Affinity Measurement of Anti-Arg1 Antibodies to Human Arg1 by Surface Plasmon Resonance Monomeric hArg1 was previously created by the mutagenesis of Arg308 found at the monomeric interfaces to an alanine residue (Mortier et al., Sci. Rep. 7, 1-9 (2017)). Arg308 is important for maintaining a salt bridge between each hArg1 monomer and mutation of this residue leads to monomerization of hArg1 and nearly 85% loss in enzymatic activity (Ibid.) We sought to explore the affinity changes of these antibodies when bound to monomeric hArg1 versus trimeric hArg1.

The binding affinities of anti-hArg1 antibodies to monomeric and trimeric hArg1 were measured by capturing human mouse chimeric antibodies on an anti-mouse IgG surface or human/humanized antibodies on an anti-human Fc surface on a Series S Sensor Chip CM5 (Cytiva) using a Biacore T200 or Biacore 4000 biosensor (Cytiva). Immobilization and affinity measurements were performed in 10 mM HEPES, 150 mM NaCl, 0.05% v/v Surfactant P20, 3 mM Ethylenediaminetetraacetic acid (EDTA), pH 7.4 (Cytiva) at 25° C. The anti-mouse IgG and anti-human Fc capture antibodies were immobilized on all surfaces of the chip following Cytiva's Amine Coupling Kit, Mouse Antibody Capture Kit, and Human Antibody Capture Kit protocols. To measure the affinity of each interaction, the anti-hArg1 antibodies were captured at 2 nM at 10 μL/minutes and 5-6 concentrations of a two-fold dilution of hArg1 from 100 nM were injected for three minutes at 30 or 50 μL/min. A reference flow cell without captured antibody was also included. After the antigen injections, the dissociation of the interaction was monitored for 5 or 10 minutes. The antibody and antigen were removed from the chip with a 30 second injection of 10 mM glycine at pH 1.5 for anti-mouse IgG captures or 3 M $MgCl_2$ for anti-human Fc captures between binding cycles.

The data were processed and fit using Biacore T200 Evaluation Software version 2.0 or Biacore 4000 Evaluation Software version 1.1 (Cytiva). The data were "double referenced" by subtracting the response from the reference control flow cell and that from a buffer injection. The data were then fit with the '1:1 Binding' model to determine the association rate constant, ka ($M^{-1}s^{-1}$, where "M" equals molar and "s" equals seconds) and the dissociation rate constant, kd ($s^{-1}$). These rate constants were used to calculate the equilibrium dissociation constant, KD (M)=kd/ka.

The affinity measurements of mAb3 binding to both trimeric and monomeric hArg1 were determined by surface plasmon resonance (SPR) studies to gain insight into how hArg1 oligomerization corresponds to antibody binding. MAb3's binding to trimeric hArg1 was quite potent (KD=0.74 nM) and there was no measurable binding between mAb3 and monomeric hArg1 (Table 8).

TABLE 8

SPR data for mAb3 affinitiy for monomeric and trimeric hArg1

| hArg1 Trimeric | | | | |
|---|---|---|---|---|
| Antibody | Ka (1/Ms) | Kd (1/s) | KD (M) | STD KD (M) |
| mAb3 | 1.7 × 10E6 | 1.2 × 10E−3 | 0.74 × 10E−9 | 8.9 × 10E−11 |
| hArg1 monomeric | | | | |
| Antibody | Ka (1/Ms) | Kd (1/s) | KD (M) | STD KD (M) |
| mAb3 | No binding | | | |

Example 7

Antibody Binding Affinities to Trimeric hArg1 and Monomeric hArg1

The antibodies have interactions spanning across the hArg1 monomeric interfaces when hArg1 is present in the natural, trimeric form. SPR assays revealed the reduction or loss of binding potencies of the mAbs when hArg1 was forced into a monomeric state.

The affinity matured mAb3 has numerous interactions with two monomers and we therefore hypothesized that mAb3 would have drastically reduced binding potency when hArg1 is monomerized. Indeed, while the binding of mAb3 to trimeric hArg1 was quite potent, measurable binding between mAb3 and monomeric hArg1 was completely lost (Table 8). When considering the surface area between hArg1 and mAb3, one monomer shares 372 $Å^2$ and 1 salt bridge with mAb3; the other monomer shares 1020 $Å^2$ of surface area but no salt bridges (Table 9). The nearly 75% reduction in shared surface area or interactions resulted in loss of all measurable mAb interaction.

TABLE 9

Surface area, hydrogen bonds, and salt bridges between antibodies and hArg1

| Antibody | hArg1 monomer | Antibody chain | Surface area ($Å^2$) | # Hydrogen bonds | # salt bridges |
|---|---|---|---|---|---|
| mAb1-mAb3 | MonA | HC | 372 | 3 | 1 |
| | MonB | LC | 366 | 4 | 0 |
| | MonB | HC | 654 | 9 | 0 |

Surface area calculations done with proximal isovelocity surface area (PISA) (Krissinel & Henrick, J. Mol. Biol. 372, 774-797 (2007))

Example 8

Size Exclusion Chromatography with Multi-Angle Light Scattering (SECMALS)

Figure 4:
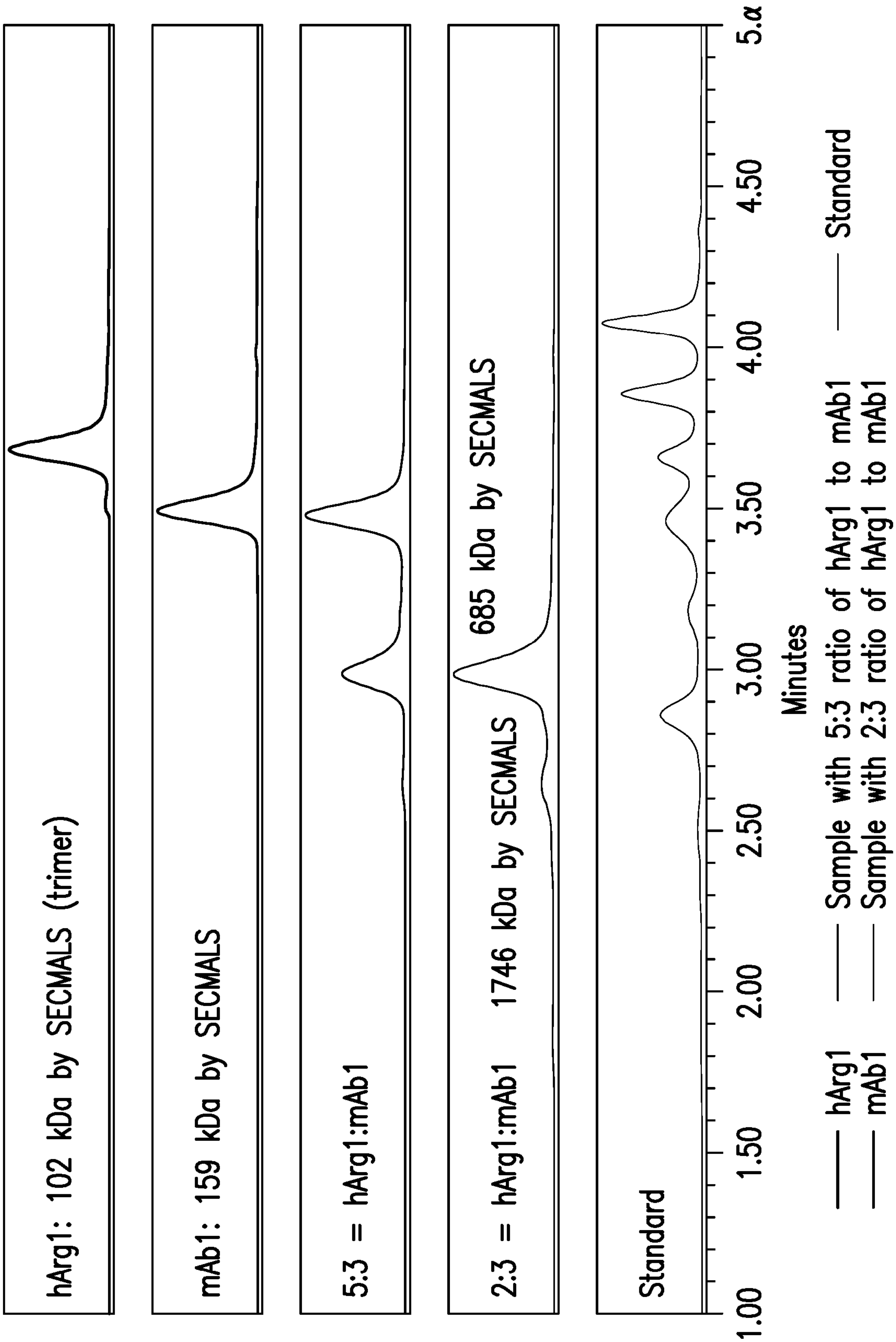
FIG. 4. Shows size exclusion chromatography with multi-angle light scattering (SECMALS) results of hArg1 and mAb1 mixed together in two ratios, i.e., 5:3 ratio and 2:3 ratio. The results verify that the best fit for the hArg:mAb1 ratio is 2:3.

SEC was performed on a Waters ACQUITY UPLC H-Class system equipped with a ethylene-bridged hybrid (BEH) 450 Å, 2.5 μm column (Waters). The sample was prepared by diluting to a final concentration of 1 mg/mL, and injecting 20 μg. Isocratic flow of mobile phase buffer, 1×PBS, 0.02% sodium azide (pH 7.0) was run at 0.5 mL/minutes. The separation was conducted at ambient temperature and the column effluent was monitored at 280 nm. MALS analysis of the sample was performed continuously on the SEC column eluate, as it passed through a μDAWN MALS detector and an Optilab UT-rEX refractive index detector for UHPLC (both Wyatt Technology). Data was analyzed with the ASTRA® software (Wyatt Technology). The results for mAb1 are shown in FIG. 4 and Table 10 and show that fit for the hArg1:mAb1 ratio is 2:3.

TABLE 10

| Name | Description | Calculated MW (Da) | MW SEC MALS (Da) |
|---|---|---|---|
| Control | hArg1 Trimer | 104,205 | 102,000 |
| mAb1 | Anti-hArg1 antibody | 147,075 | 159,000 |

Example 9

Cryo-Electron Microscopy Methods and Image Processing:

All the hArg1:mAb complexes were formed by mixing the protein and the mAb in reaction buffer (25 mM HEPES pH 7.4, 150 mM NaCl, 1.0 mM $MnCl_2$) at 3:1 molar ratio and incubating the mixture for 30 minutes before preparing the grids. Grids were prepared and data were collected at NanoImaging Services (San Diego, CA) according to the following protocol and the specifications in Tables 11and 12A-12B: After incubation, the sample containing the complex was diluted with reaction buffer to approx. Then, 75 μM concentration of monomeric Arginase was then mixed with dodecyl maltoside (DDM) to the critical micelle concentration (CMC) to reduce particle aggregation and used immediately afterwards to freeze grids. Then, 3 μL of each sample were applied to 1.2/1.3 grids (Au/Au Quantifoil or C/Cu C-flat), which have been previously plasma-cleaned using a Gatan Solarus (Pleasanton, California) and mounted in a Vitrobot Mark IV. The sample was then blotted with filter paper for six seconds and plunged in liquid ethane. Electron microscopy was performed using a ThermoFisher Titan Krios (Hillsboro, Oregon) transmission electron microscope operated at 300 kV and equipped with a Gatan Quantum 967 LS imaging filter and Gatan K2 Summit direct detector. Automated data-collection was carried out using Leginon software (Suloway et al., J. Struct. Biol. 151: 41-60 (2005)) in counting mode, collecting between 1500 and 3000 movies per sample at a defocus range between −1.0 and −2.0 μm, calibrated pixel size of 1.04 Å/pix and total dose of 45 $e^-$/Å (Suloway et al., Ibid.).

Movies were aligned using MotionCor2 (Zheng et al., Nat. Methods 14: 331-332 (2017)) and the contrast transfer function (CTF) calculated using CTFFIND4 (Rohou. & Grigorieff, J. Struct. Biol. 192: 216-221 (2015)) within the Appion package (Lander et al., J. Struct. Biol. 166: 95-102 (2009)). Aligned micrographs were imported into cryo-oSPARC (Punjani et al., Nat. Methods 14: 290-296 (2017)) where all the subsequent steps of image processing were realized following a standard single particle workflow until the final reconstruction. Particle picking was performed based on blobs for mAb1. When the 2D classes from mAb1 became available, they were used as templates to select particles for the other samples. Several rounds of 2D classification ab-initio were performed to select the best-looking particles and separate the different oligomerization complexes when they existed. In all the cases non-uniform refinement and higher-order contract transfer function (CTF) refinement were used to generate the best reconstructions. Symmetries C3 or C1 were enforced during the final refinement when applicable. When used during the refinement, masks were generated in Chimera(Pettersen et al., J Comput Chem. 25: 1605-12 (2004)). Initial models for the structures were generated using MOE 2018.01 (Chemical Computing Group ULC, Montreal, QC, Canada) and the available structure of hArg (PDB ID=6V7C) (Mitcheltree. et al., ACS Med. Chem. Lett. 11, 582-588 (2020)). The structures were built in Coot (Emsley et al., Biol. Crystallog. 60: 2126-2132 (2004)) based on the cryoEM density maps and subjected to one round of real space refinement in Phenix (Afonine et al., Comput. Crystallogr. Newsl. 4: 43-44 (2013)). Summary of cryo-EM data collection is shown in Table 11 and statistics data processing, map generation, and model refinement values are shown Tables 12A and 12B. Table 13 summarizes the specific epitope-paratope interactions between hArg1 and mAbs1-3.

TABLE 11

Summary of cryo-EM data collection

| Sample | mAb1 | mAb2 | mAb3 |
|---|---|---|---|
| Microscope | Krios/EF | Krios/EF | Krios/EF |
| Camera | K2 | 2 | K2 |
| Pixel size (Å/pix) | 1.04 | 1.04 | 1.04 |
| Dose ($e^-$/Å) | 45.46 | 44.32 | 44.47 |
| #images | 1172 | 778 | 1046 |
| Defocus range (μm) | 1.0 to −1.8 | 1.2 to −2.0 | 1.0 to −2.0 |

TABLE 12A

Statistics data processing, map generation and model refinement.

| Sample | mAb1 Full Complex (Two trimers: three mAbs) | mAb1 Masked | mAb1 Two trimers: Two mAbs Full |
|---|---|---|---|
| # particles | 37385 | 77986 | 16810 |
| Global resolution (Å) | 3.6 | 3.4 | 4.1 |
| RMSD Bonds (Å) | | 0.011 | 0.007 |
| RMSD Angles (Deg) | | 1.09 | 1.14 |
| CC Mask | | 0.82 | 0.73 |
| CC volume | | 0.81 | 0.73 |
| CC peaks | | 0.72 | 0.69 |
| Ramachandran | | | |
| Outliers (%) | | 0.89 | 0.66 |
| Allowed (%) | | 9.9 | 10.1 |
| Favored (%) | | 89.2 | 89.2 |
| All-atom clashscore | | 6.9 | 11.0 |

For mAb1, the full complex was not refined in Phenix. For the other complexes, the relatively low values for the CCMask, Volume and Peaks observed for the refinement of the full complex reflect the high degree of variability in the resolution range.

TABLE 12B

Statistics data processing, map generation and model refinement

| Sample | mAb2 Complex (Two trimers: three mAbs) | mAb3 Full Complex (Two trimers: Three mAbs) |
|---|---|---|
| # particles | 52550 | 52241 |
| Global resolution (Å) | 3.7 | 4.0 |
| RMSD Bonds (Å) | 0.010 | 0.006 |
| RMSD Angles (Deg) | 1.07 | 1.05 |
| CC Mask | 0.62 | 0.78 |
| CC volume | 0.63 | 0.78 |
| CC peaks | 0.61 | 0.75 |
| Ramachandran | | |
| Outliers (%) | 0.80 | 0.40 |
| Allowed (%) | 11.4 | 12.9 |
| Favored (%) | 87.8 | 86.7 |
| All-atom clashscore | 7.5 | 12.0 |

TABLE 13

Amino acid interactions between the mAb1, mAb2, and mAb3 paratope and the hArg1 epitope.

| Heavy Chain | hArg1 monomer A |
|---|---|
| Tyr54 | Lys39 |
| Gly56 | Thr290 |
| Thr69 | Pro286 |
| Thr72, Asp73 | Lys33 |
| Thr74 | Lys33, Ala34, Gly35, Glu38 |
| Ser75 | Arg32, Glu38 |
| **Light Chain** | **hArg1 monomer B** |
| Ser28 | Glu25 |
| Tyr32 | Ser16, Lys17, Asn69 |
| Ser67 | Asp57 |
| Ser92 | Pro20, Gly22 |
| Leu93 | Ser281 |

TABLE 13-continued

Amino acid interactions between the mAb1, mAb2, and mAb3 paratope and the hArg1 epitope.

| Heavy Chain | hArg1 monomer B |
|---|---|
| Tyr54 | Asp181 |
| Asn57, | Lys284 |
| Thr58 | Arg21 |
| Asn59 | Pro20, Arg21 |
| Tyr102 | Thr246 |
| Gly103 | His126, Asp128, Asn130, Ser137, His141, Gly142, Asp183, Glu186 |
| Tyr104 | Thr136, Asp183 |
| Arg105 | Ser137 |
| Ser106 | Thr136, Ser137 |
| Pro107 | Lys68, Ser137, Asn139 |
| Tyr108 | |

All interactions shown here are within 4 Å.

VH and VL amino acid position numbers are as set forth in SEQ ID NO: 3 and 4, respectively, and not according to Kabat.

Example 10 mAb1-3 2:3 Complexes and Impact of the 2:3 Complex on hArg1 Inhibition

Antibodies mAb1, mAb2, and mAb3 are human antibodies identified via yeast display technologies. Antibody mAb1 is constructed on a mouse IgG2a/kappa backbone with a fairly flexible hinge region. Antibody mAb2 is constructed on a mouse IgG1 D265A/kappa backbone, which is more rigid and conformationally restricted than that of mAb1 and shares identical variable regions with mAb1, differing only in their constant domains. MAb3 is constructed on a human IgG4 S228P/kappa backbone and is an affinity-matured version of mAb1, differing by eight amino acids in the heavy chain variable domain and with identical light chain variable domains. Despite these differences, all three mAbs share the same epitope, leading to identical interactions with hArg1. The overall characterization for these three 2:3 complexes are therefore presented in tandem.

Figure 5A:
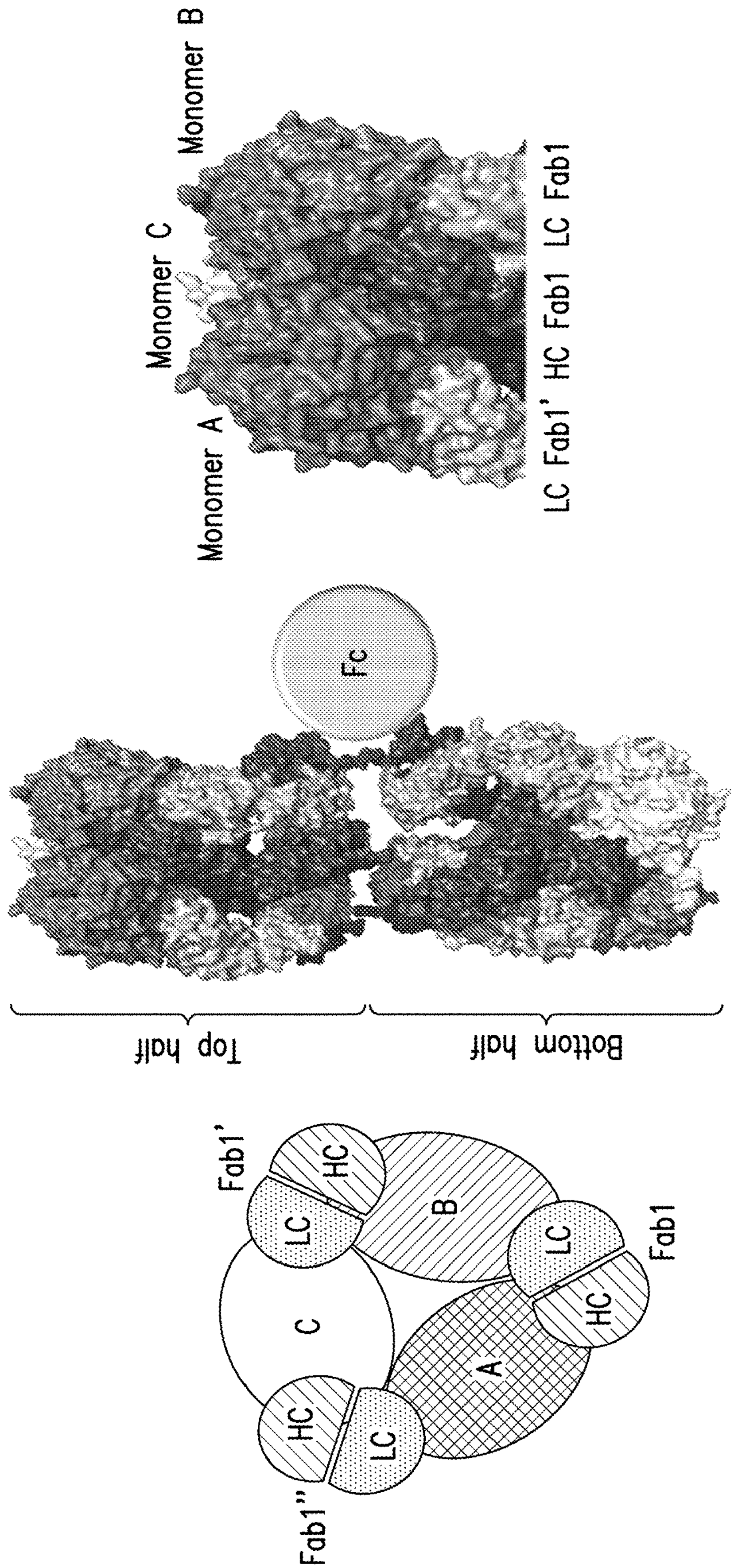
FIG. 5A. Epitope determination for mAb1 parent and affinity matured antibodies and shows an overview of how the large 2:3 hArg1 to mAb1 complex assembles. The three monomers of the hArg1 trimer are shown as monomers A, B, and C, and the mAb1 heavy chain and light chain are colored dark grey and light grey, respectively. Left: surface representation of the mAb1 complexes. Middle: the hArg1 trimer:mAb1 complex is viewed in a simplified cartoon form as viewed from the top. Each HC interacts with two hArg1 monomers while each LC interacts with only one hArg1 monomer; these interactions are symmetric around the hArg1 trimer. The Fragments crystallizable (Fcs) are not visible but one was added here to show the general location for one antibody in this complex. Right: a surface representation provides a closeup view of mAb1's interaction across two hArg1 monomers.
Figure 5B:
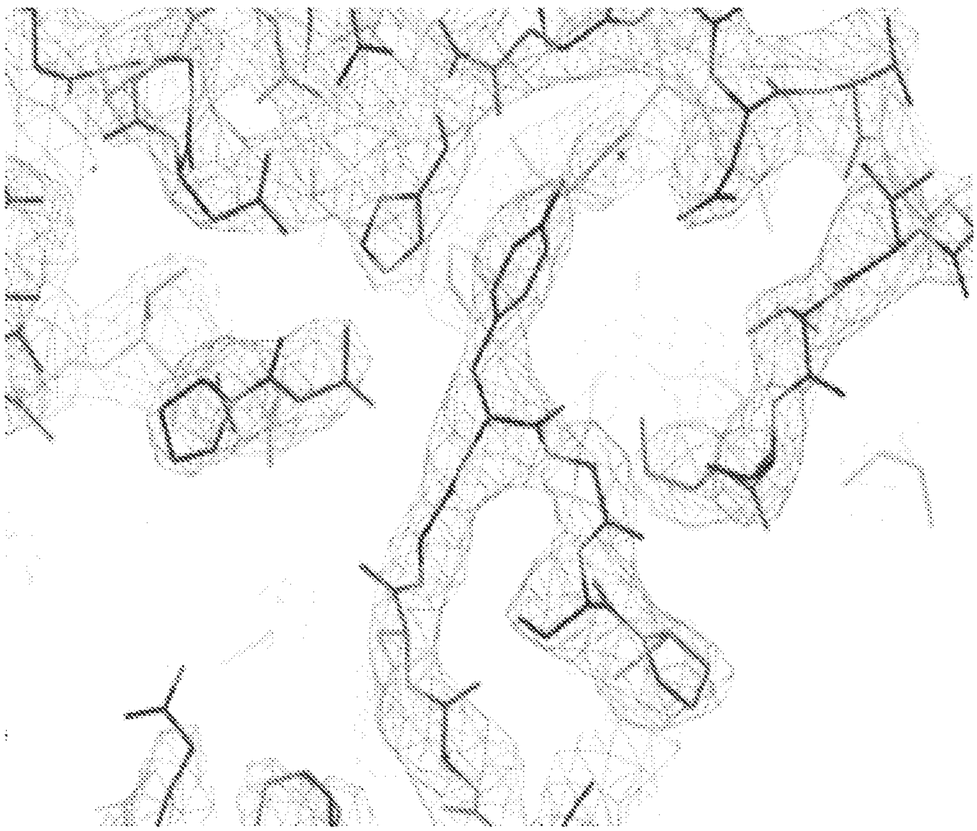
FIG. 5B. A sample of the electron density at the hArg1:Fab interface is shown, highlighting the ability to confidently model all main chain and side chain atoms.

FIG. 5A shows the overall arrangement of the 2:3 complex consisting of two hArg1 trimers and the three mAbs. The hinge region of each mAb1-3 backbone holds an approximate T shape with an angle of about 150° where each Fab from a single mAb interacts with only one of the two trimers. The local resolution of about 3 Å and high-quality electron density map (FIG. 5B) permitted the determination of the epitope and paratope interactions between mAbs1-3 and hArg1. Due to the locally-applied C3 symmetry the interactions between hArg1 and mAb are equivalent around the trimer. For the following analysis, the monomers of each trimer are labeled as A, B, and C (FIG. 5A). Each Fab interaction spans two monomers of the trimer such that Fab1 binds to both monomers A and B in the same hArg1 trimer, Fab1' binds to monomers B and C, and Fab1" binds to monomers C and A. As shown in FIG. 5A, each heavy chain (HC) of each Fab interacts with two monomers while the light chain (LC) interacts with only one. The buried surface area between mAb1 HC+LC and hArg1 is 1020 $Å^2$ while the surface area between hArg1 and mAb1 HC is only 372 $Å^2$ (Table 9). The rest of the complex follows this pattern with each monomer having two sets of interactions: binding to the HC and LC of one Fab and only the HC of a second Fab.

Figure 5C:
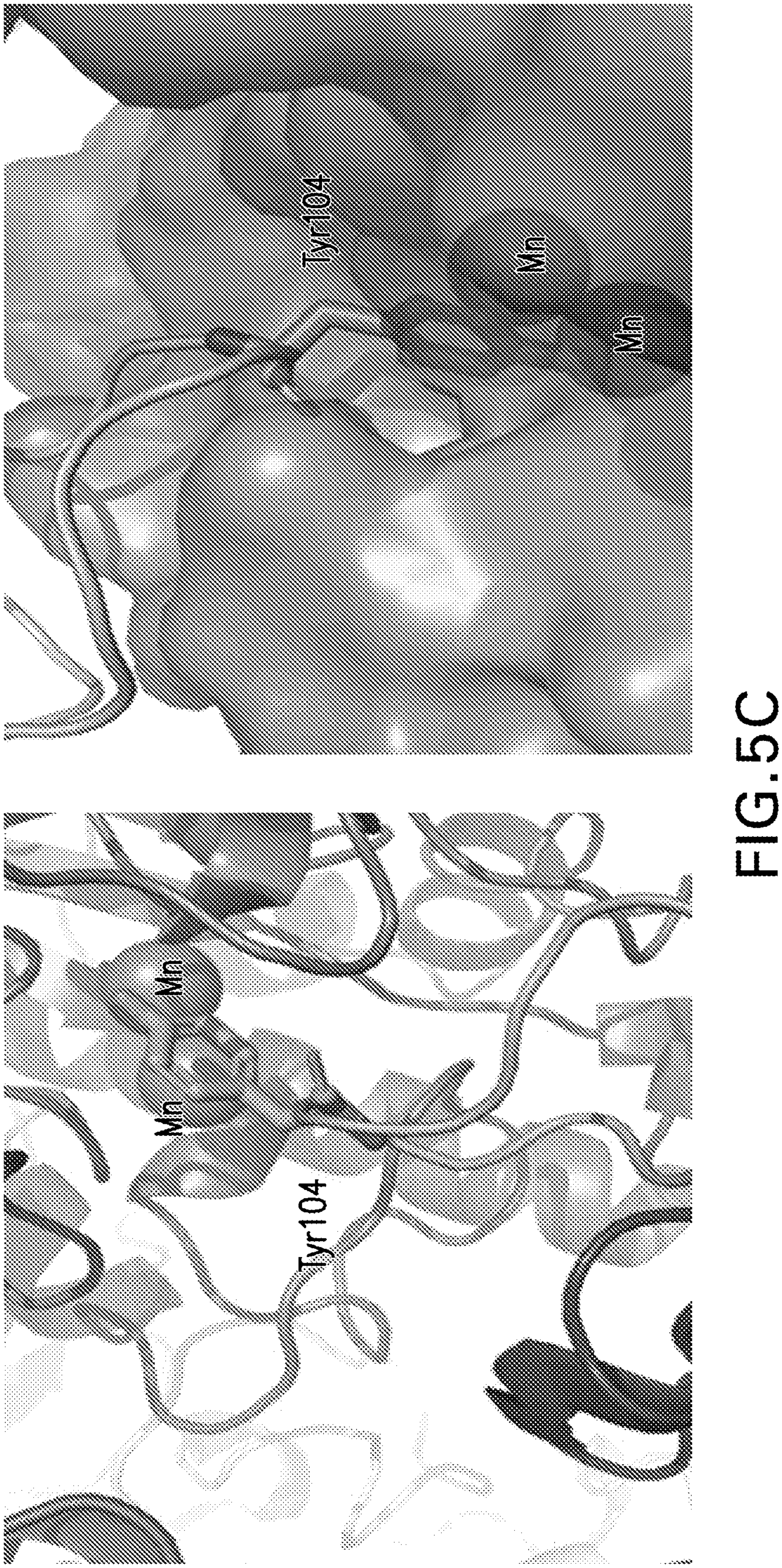
FIG. 5C. mAb1 is characterized by a very long CDR-3 loop. Tyr104 (shown as sticks; Tyr100 according to Kabat numbering of the VH) extends into the hArg1 active site. The binuclear active site manganese ions (Mn) are shown as spheres.

MAbs1-3 have prolonged HC CDR-3 loops that extend toward the opening of the hArg1 active site (FIG. 5C).

Inactivation of hArg1 is achieved by the presence of Tyr104 that inserts into and sterically blocks the hArg1 active site near the exterior surface of the enzyme. Overall steric occlusion of the active site entry channel appears responsible for inhibition of hArg1.

The fully discernable formation of the large macromolecular complexes consisting of two trimers and three full mAbs is unique in the literature. Recently, a similar complex of a single HtrA1 trimer and three anti-HtrA1 Fabs was determined through negative staining EM (Ciferri et al., Biochem. J. 472, 169-181 (2015)) analyses coupled with a previously determined low-resolution SAXS structure of the HtrA1 trimer (Eigenbrot et al., Structure 20, 1040-1050 (2012)) to build a 1:3 model of enzyme:antibody. The full "cage-like" structure was proposed and generated by "juxtaposing and mirroring" two of the HtrA1:Fab 1:3 complexes resulting in a 2:3 HtrA1:Ab complex much like those presented here. In vitro enzymatic assays determined that anti-HtrA1 full-length antibodies had greater than 10-fold higher potency versus Fabs alone, hinting that the ability of HtrA1 to form these large macromolecular complexes of two HtrA1 trimers to three antibodies is instilling higher potency. While singular anti-hArg1 Fab arms were not tested in our studies, we hypothesize that all mAbs that showed distinct 2:3 complexes are also highly potent due in part to the complexation of enzymes and antibodies.

The means of inhibition by mAbs1-3 is based on steric occlusion of the hArg1 active site. As shown in FIG. 5C and described previously, these antibodies function by inserting an amino acid side chain into, and therefore sterically blocking, the narrow active site channel. This is accomplished by Tyr104 on the HC CDR-3 loop in mAbs1-3. While mAb1, mAb2, and mAb3 utilize Tyr104, the subsequent Arg105 of these mAbs is also near the active site opening but does not access the narrow channel.

Rather than relying on a specific residue for inhibition it is clear that overall steric occlusion of the active site is the inhibitory mechanism of the antibodies.

Example 11

Ability of mAb1 to Form a 2:2 Complex

Figure 6A:
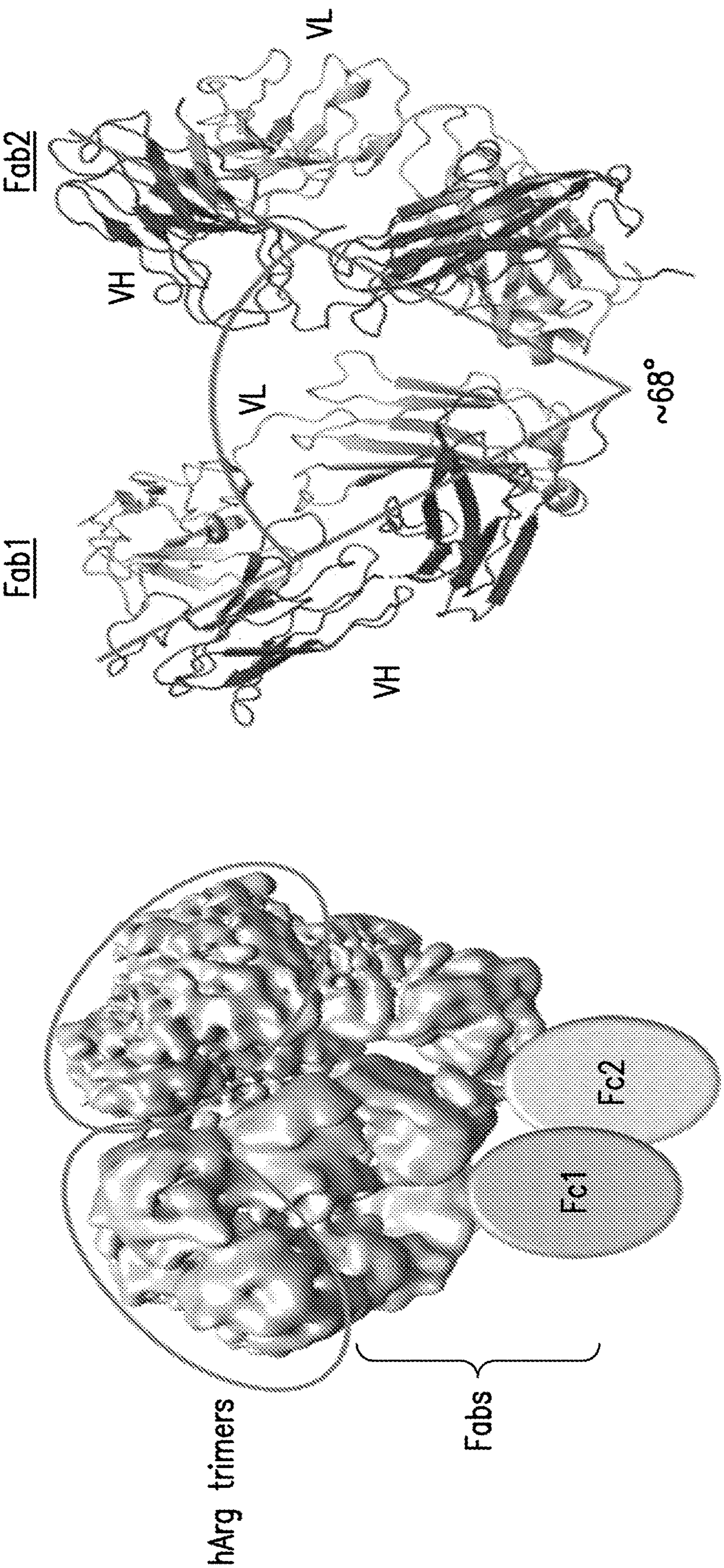
FIG. 6A. The mAb1 2:2 complex. Left panel: the resulting EM maps allow for the identification of the two trimers and two sets of Fabs. As with the 2:3 complex, the FCs were not visible but are added here to show their general location in this complex. The right panel: the angle between the two Fabs of an antibody is ~67° in the 2:2 complex, versus the about 160° in the 2:3 complex.
Figure 6B:
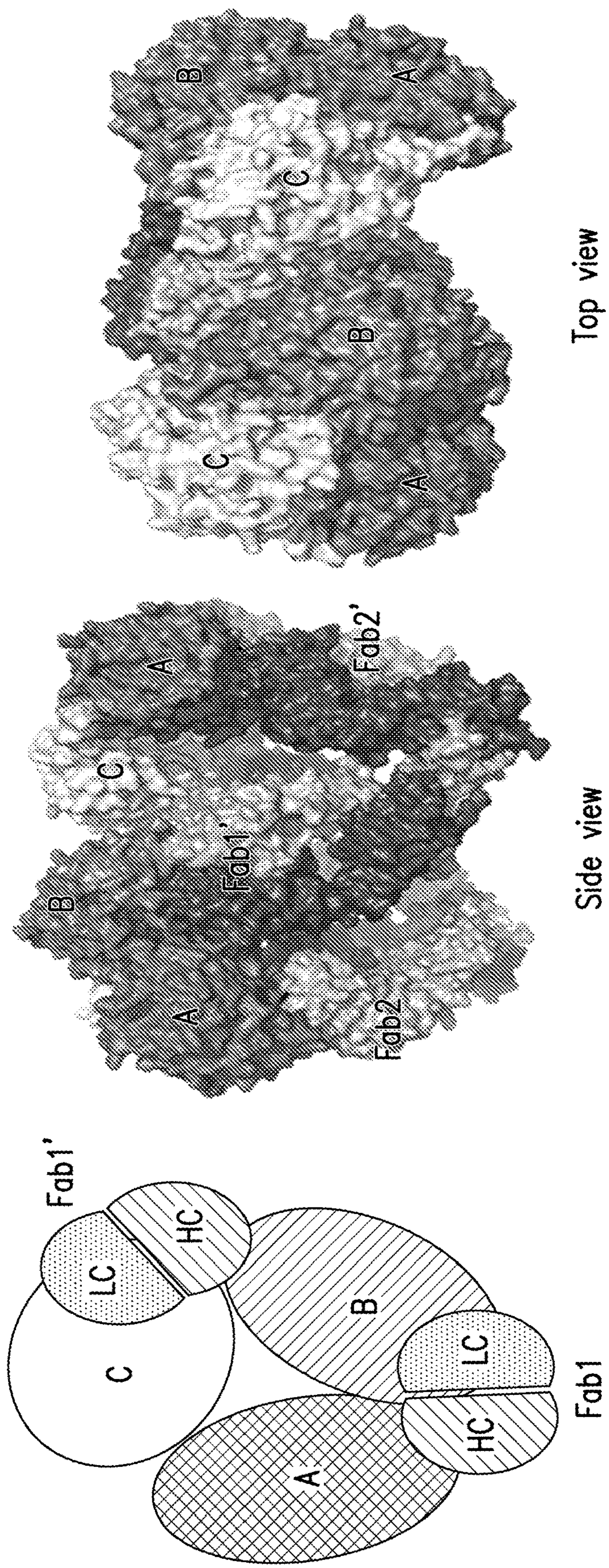
FIG. 6B. Shows an overview of how the 2:2 complex assembles with hArg1 monomers and the mAbs. The three monomers of the hArg1 trimer are shown as monomers A, B, and C, and the mAb1 heavy chain and light chain are colored dark grey and light grey, respectively. The left-hand cartoon representation provides a simplistic depiction of the mAb:hArg1 interactions in the complex. Here it is apparent that that arrangement of the antibodies is quite asymmetric and only one monomer (monomer B here) makes all three mAb interactions (mAb1 LC and HC; and mAb2 HC) as seen in the 2:3 complex. The middle image displays a surface representation in a side-on view of the complex. The right-hand image displays these interactions in a top-down view of the complex.

Interestingly, two classes of hArg1:mAb1 complexes that were identified during 3D classification were not present in the mAb2 or mAb3 samples. Approximately 80% of all complexes identified were composed of two hArg1 trimers and three mAb1s forming a 2:3 complex while the remaining 20% of complexes were composed of two hArg1 trimers and two mAb1s (hereafter called a 2:2 complex). Although the resolution of the map was lower (3.6 Å for 2:3 versus 4.1 Å for 2:2), the high-quality map (FIG. 6A) allowed for both the two hArg1 trimers. and two mAbs to be manually positioned. In this smaller complex the angle between the Fabs is only about 60° and results in the two hArg1 trimers being positioned much closer together (FIG. 6A). The epitope and paratope interactions between each Fab and hArg1 monomers are identical to the 2:3 complex, however one set of interactions is absent due to having only two mAb1s present (FIG. 6B). Here, Fab1 binds to both monomer A and monomer B, Fab1' binds to monomers B and C, but the Fab that would bind across the monomer C and A is absent. Because of this, as shown in the simplified diagram in FIG. 6B, both monomers B and C are inhibited by the HC CDR-3 loops of Fab1 and Fab1', respectively, while the active site of monomer A remains open and uninhibited.

The immunoglobulin backbones differ between antibodies characterized here and seem to play a role in the formation of different structure classes identified microscopically. For instance, while mAbs1, mAb2, and mAb3 all share identical epitope:paratope interactions, only mAb1 exhibited a 2:2 complex. In 2002 (Saphire et al., J. Mol. Biol. 319, 9-18 (2002)) a fully intact human IgG including the hinge region confirmed that IgG hinges resemble "loose tethers," allowing the Fabs to rotate freely while still retaining a covalent link between the Fab and Fc domains. This flexible linkage, along with the specific antibody:antigen interactions, leads to the variance in Fab positioning and reach between the complexes.

As shown herein, the extended length of mAbs1-3 is approximately the same resulting in antibodies which share similar torsional rotations from the top trimer to the bottom. While mAb1 is built on a mouse IgG2a backbone, mAb2 is built on a mouse IgG1 backbone, which have been shown to be less flexible than the mouse IgG2a backbone hinge regions (Dangl et al., EMBO J. 7, 1989-1994 (1988)). This enhanced flexibility in the IgG2a hinge region may be responsible for allowing the 2:2 complex to form with mAb1 but not mAb2. A possible scenario is that the 2:2 complex is formed first, followed by an opening up of first two mAb1s to permit a third mAb1 to bind to one hArg1 trimer and then eventually to the second hArg1 trimer. With a shorter and more rigid IgG1 backbone for mAb2, this extreme movement of the hinge is restricted and therefore only 2:3 complexes are seen. While it is difficult to compare the murine backbones of mAb1 and mAb2 directly to the human IgG4 backbone of mAb3, anisotropy decay studies showed that the mean time for decay of murine IgG2a was shorter than that of human IgG4, hinting at a more flexible murine IgG2a (Dangl e al., ibid.). Therefore, although not directly assessed herein, it suggests that the human IgG4 hinge region is more rigid than murine IgG2a, allowing only the 2:3 complexes to form.

Example 12

Comparison of Complex Sizes and Shapes

Figure 7:
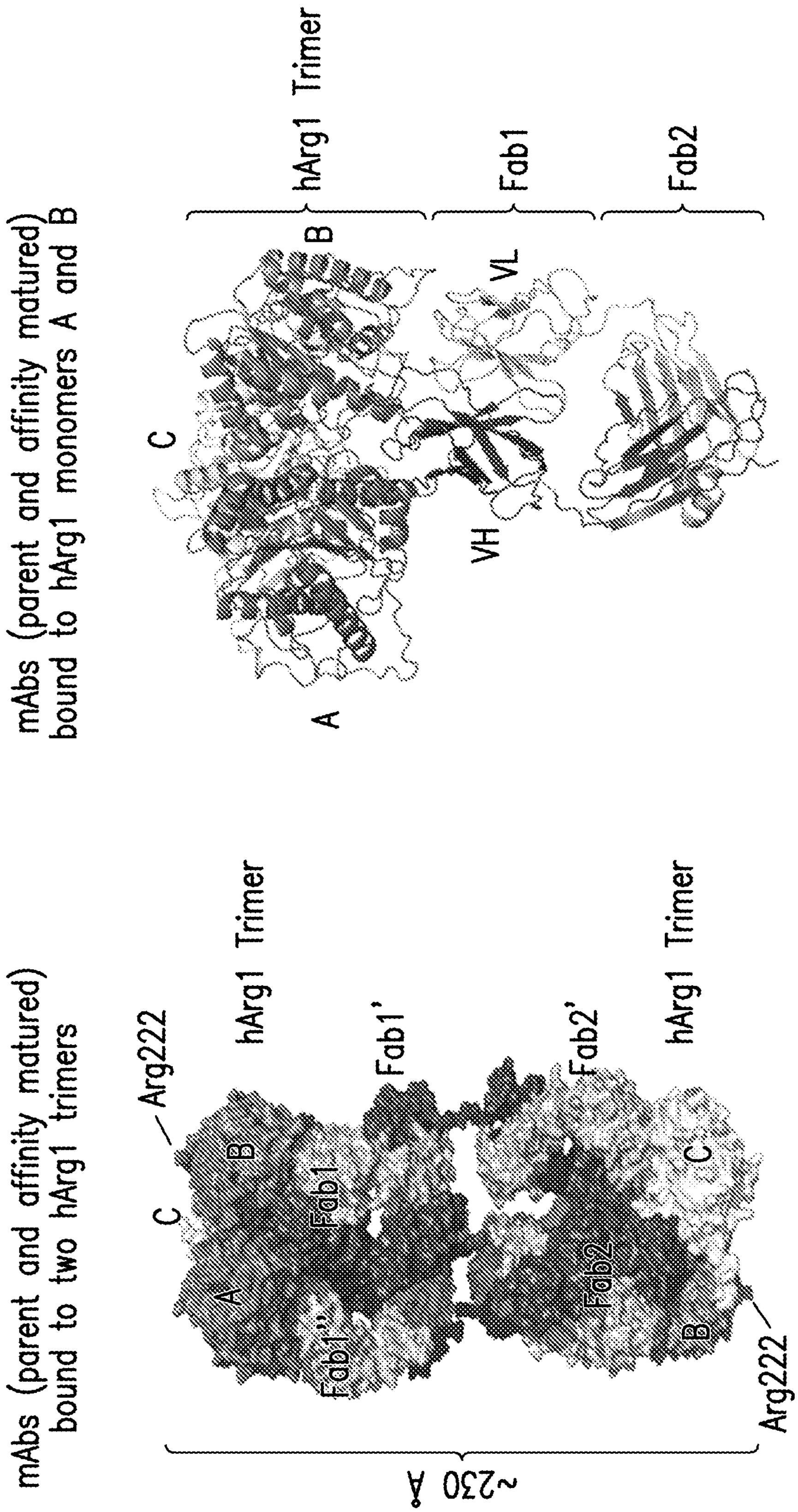
FIG. 7. Size and shape comparison of an hArg1:mAb (parent or affinity matured) 2:3 trimer. Left panel: the hArg1:mAb complex is approximately 230 Å in length when measuring between the C-α of the Arg222 residues in both the top and bottom B monomers of hArg1. Right Panel: the binding of one Fab of the mAb to monomers A and B of an hArg1 trimer is depicted in cartoon form and illustrate how the Fab binds to the monomer. The three monomers of the hArg1 trimer are shown as monomers A, B, and C, and the mAb1 heavy chain and light chains are colored dark grey and light grey, respectively.

When considering the overall shape and size of the complexes (FIG. 7), it is clear that some of these differences are due to the varying backbone characteristics as described above. However, the epitope of the antibody is responsible for determining how and where the antibody binds to the hArg1 trimer which also plays a role in the antibody orientation and therefore the overall complex shape. For mAbs1-3, the epitope is at the very tip of the antibody (FIG. 7) with the HC accounting for the majority of the interactions with hArg1, resulting in the Fab binding almost perpendicular to the hArg1 trimer. Considering that cryoEM, Isothermal titration calorimetry (ITC), and SEC-MALS data confirm the presence of the 2:3 complexes, the conformation of the mAbs binding to both the top and bottom halves of these complexes results in the antibodies taking on an almost T-shape appearance in which the angle of the backbone is about 150 degrees. This results in an elongated complex approximately 230 Λ in length (FIG. 7).

TABLE OF SEQUENCES

| SEQ ID NO: | Description | Sequence |
|---|---|---|
| 1 | Human arginase 1 | MSAKSRTIGIIGAPFSKGQPRGGVEEGPTVLRKAGLLEKL<br>KEQECDVKDYGDLPFADIPNDSPFQIVKNPRSVGKASEQ<br>LAGKVAEVKKNGRISLVLGGDHSLAIGSISGHARVHPDL<br>GVIWVDAHTDINTPLTTTSGNLHGQPVSFLLKELKGKIPD<br>VPGFSWVTPCISAKDIVYIGLRDVDPGEHYILKTLGIKYF<br>SMTEVDRLGIGKVMEETLSYLLGRKKRPIHLSFDVDGLD<br>PSFTPATGTPVVGGLTYREGLYITEEIYKTGLLSGLDIME<br>VNPSLGKTPEEVTRTVNTAVAITLACFGLAREGNHKPID<br>YLNPPK |
| 2 | VH1 (parent) | QVQLVQSGAEVKKPGASVKVSCKASGYTFTNYGISWVR<br>QAPGQGLEWMGWISAYNGNTNYAQKLQGRVTMTTDTS<br>TSTAYMELRSLRSDDTAVYYCAREGAYGYRSPYHNWF<br>DPWGQGTLVTVSS |
| 3 | VH2 (affinity matured) | **E**VQLVQSGAEVKKPGASVKVSCKASGYTF**F**KYGISWVR<br>QAPGQGLEWMGSIS**P**Y**T**G**E**T**H**YAQKLQGRVTMTTDTST<br>STAYMELRSLRSDDTAVYYCAREGAYGYRSPY**Q**NWFD<br>PWGQGTLVTVSS |
| 4 | VL | EIVMTQSPATLSLSPGERATLSCRASQSVSSYLAWYQQK<br>PGQAPRLLIYDASNRATGIPARFSGSGSGTDFTLTISSLEP<br>EDFAVYYCQQHSLLPRTFGGGTKVEIK |
| 5 | VH1-CDR1 Kabat | NYGIS |
| 6 | VH1-CDR2<br>Kabat/Kabat + Chothia | WISAYNGNTNYAQKLQG |
| 7 | VH1-CDR3<br>Kabat/Chothia/Kabat +<br>Chothia/AbM | EGAYGYRSPYHNWFDP |
| 8 | VH1-CDR1 Chothia | GYTFTNY |
| 9 | VH1-CDR2 Chothia | SAYNGN |
| 10 | VH1-CDR1<br>Kabat + Chothia/AbM | GYTFTNYGIS |
| 11 | VH1-CDR2 AbM | WISAYNGNTN |
| 12 | VH1-CDR1 IMGT | GYTFTNYG |
| 13 | VH1-CDR2 IMGT | ISAYNGN |
| 14 | VH1-CDR3 IMGT | AREGAYGYRSPYHNWFDP |
| 15 | VH1-CDR1 Contact | TNYGIS |
| 16 | VH1-CDR2 Contact | WMGWISAYNGNTN |
| 17 | VH1-CDR3 Contact | AREGAYGYRSPYHNWFD |
| 18 | VH2-CDR1 Kabat | **K**YGIS |
| 19 | VH2-CDR2<br>Kabat/Kabat + Chothia | SIS**P**Y**T**G**E**T**H**YAQKLQG |
| 20 | VH2-CDR3<br>Kabat/Chothia/Kabat +<br>Chothia/AbM | EGAYGYRSPY**Q**NWFDP |
| 21 | VH2-CDR1 Chothia | GYTF**FK**Y |
| 22 | VH2-CDR2 Chothia | S**P**Y**T**G**E** |
| 23 | VH2-CDR1<br>Kabat + Chothia/AbM | GYTF**FK**YGIS |
| 24 | VH2-CDR2 AbM | SIS**P**Y**T**G**E**TN |
| 25 | VH2-CDR1 IMGT | GYT**FK**NYG |
| 26 | VH2-CDR2 IMGT | IS**P**Y**T**G**E** |

TABLE OF SEQUENCES-continued

| SEQ ID NO: | Description | Sequence |
|---|---|---|
| 27 | VH2-CDR3 IMGT | AREGAYGYRSPY**Q**NWFDP |
| 28 | VH2-CDR1Contact | **FK**YGIS |
| 29 | VH2-CDR2 Contact | WMGSIS**PYTGE**TN |
| 30 | VH2-CDR3 Contact | AREGAYGYRSPY**Q**NWFD |
| 31 | VL-CDR1 Kabat/Chothia/Kabat + Chothia/AbM | RASQSVSSYLA |
| 32 | VL-CDR2 Kabat/Chothia/Kabat + Chothia/AbM | DASNRAT |
| 33 | VL-CDR3 Kabat/Chothia/Kabat + Chothia/AbM/IMGT | QQHSLLPRT |
| 34 | VL-CDR1 IMGT | QSVSSYLA |
| 35 | VL-CDR1 Contact | SSYLAWY |
| 36 | VL-CDR2 Contact | LLIYDASNRA |
| 37 | VL-CDR3 Contact | QQHSLLPR |
| 38 | Human IgG1 HC constant domain | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPELL GGPSVFLFPPKPKDTLMISRTPEVTCVVVDVSHEDPEVKF NWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVM HEALHNHYTQKSLSLSPGK |
| 39 | Human IgG1 HC Constant domain (L234A L235A D265S) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPE**AA** GGPSVFLFPPKPKDTLMISRTPEVTCVVVSVSHEDPEVKF NWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVM HEALHNHYTQKSLSLSPGK |
| 40 | Human IgG1 HC Constant domain (L234A L235A P329G) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPE**AA** GGPSVFLFPPKPKDTLMISRTPEVTCVVVSVSHEDPEVKF NWYVDGVEVHNAKTKPREEQYNSTYRVVSVLTVLHQD WLNGKEYKCKVSNKAL**G**APIEKTISKAKGQPREPQVYT LPPSRDELTKNQVSLTCLVKGFYPSDIAVEWESNGQPEN NYKTTPPVLDSDGSFFLYSKLTVDKSRWQQGNVFSCSV MHEALHNHYTQKSLSLSPGK |
| 41 | Human IgG1 HC Constant domain (L235E) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPEL**E** GGPSVFLFPPKPKDTLMISRTPEVTCVVVDVSHEDPEVKF NWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVM HEALHNHYTQKSLSLSPGK |
| 42 | Human IgG1 HC Constant domain (D265A) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPELL GGPSVFLFPPKPKDTLMISRTPEVTCVVV**A**VSHEDPEVKF NWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN |

TABLE OF SEQUENCES-continued

| SEQ ID NO: | Description | Sequence |
|---|---|---|
| | | YKTTPPVLDSDGSFFLYSKLTVDKSRWQQGNVFSCSVM HEALHNHYTQKSLSLSPGK |
| 43 | Human IgG1 HC Constant domain (D265A N297G) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPELL GGPSVFLFPPKPKDTLMISRTPEVTCVVV**A**VSHEDPEVKF NWYVDGVEVHNAKTKPREEQY**G**STYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVM HEALHNHYTQKSLSLSPGK |
| 44 | Human IgG1 HC Constant domain (E233A/L235A) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAP**ALA** GGPSVFLFPPKPKDTLMISRTPEVTCVVVDVSHEDPEVKF NWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVM HEALHNHYTQKSLSLSPGK |
| 45 | Human IgG1 HC Constant domain (N297X, wherein X is any amino acid other than N) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPELL GGPSVFLFPPKPKDTLMISRTPEVTCVVVDVSHEDPEVKF NWYVDGVEVHNAKTKPREEQY**X**STYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVM HEALHNHYTQKSLSLSPGK |
| 46 | Human IgG2 HC Constant domain | ASTKGPSVFPLAPCSRSTSESTAALGCLVKDYFPEPVTVS WNSGALTSGVHTFPAVLQSSGLYSLSSVVTVPSSNFGTQ TYTCNVDHKPSNTKVDKTVERKCCVECPPCPAPPVAGPS VFLFPPKPKDTLMISRTPEVTCVVVDVSHEDPEVQFNWY VDGVEVHNAKTKPREEQFNSTFRVVSVLTVVHQDWLN GKEYKCKVSNKGLPAPIEKTISKTKGQPREPQVYTLPPSR EEMTKNQVSLTCLVKGFYPSDISVEWESNGQPENNYKTT PPMLDSDGSFFLYSKLTVDKSRWQQGNVFSCSVMHEAL HNHYTQKSLSLSPGK |
| 47 | Human IgG2 HC Constant domain (D265S) | ASTKGPSVFPLAPCSRSTSESTAALGCLVKDYFPEPVTVS WNSGALTSGVHTFPAVLQSSGLYSLSSVVTVPSSNFGTQ TYTCNVDHKPSNTKVDKTVERKCCVECPPCPAPPVAGPS VFLFPPKPKDTLMISRTPEVTCVVV**S**VSHEDPEVQFNWY VDGVEVHNAKTKPREEQFNSTFRVVSVLTVVHQDWLN GKEYKCKVSNKGLPAPIEKTISKTKGQPREPQVYTLPPSR EEMTKNQVSLTCLVKGFYPSDISVEWESNGQPENNYKTT PPMLDSDGSFFLYSKLTVDKSRWQQGNVFSCSVMHEAL HNHYTQKSLSLSPGK |
| 48 | Human IgG2 HC Constant domain (P329G) | ASTKGPSVFPLAPCSRSTSESTAALGCLVKDYFPEPVTVS WNSGALTSGVHTFPAVLQSSGLYSLSSVVTVPSSNFGTQ TYTCNVDHKPSNTKVDKTVERKCCVECPPCPAPPVAGPS VFLFPPKPKDTLMISRTPEVTCVVVDVSHEDPEVQFNWY VDGVEVHNAKTKPREEQFNSTFRVVSVLTVVHQDWLN GKEYKCKVSNKGL**G**APIEKTISKTKGQPREPQVYTLPPS REEMTKNQVSLTCLVKGFYPSDISVEWESNGQPENNYK TTPPMLDSDGSFFLYSKLTVDKSRWQQGNVFSCSVMHE ALHNHYTQKSLSLSPGK |
| 49 | Human IgG2 HC Constant domain (D265A) | ASTKGPSVFPLAPCSRSTSESTAALGCLVKDYFPEPVTVS WNSGALTSGVHTFPAVLQSSGLYSLSSVVTVPSSNFGTQ TYTCNVDHKPSNTKVDKTVERKCCVECPPCPAPPVAGPS VFLFPPKPKDTLMISRTPEVTCVVV**A**VSHEDPEVQFNWY VDGVEVHNAKTKPREEQFNSTFRVVSVLTVVHQDWLN GKEYKCKVSNKGLPAPIEKTISKTKGQPREPQVYTLPPSR EEMTKNQVSLTCLVKGFYPSDISVEWESNGQPENNYKTT PPMLDSDGSFFLYSKLTVDKSRWQQGNVFSCSVMHEAL HNHYTQKSLSLSPGK |
| 50 | Human IgG2 HC Constant domain (D265A N297G) | ASTKGPSVFPLAPCSRSTSESTAALGCLVKDYFPEPVTVS WNSGALTSGVHTFPAVLQSSGLYSLSSVVTVPSSNFGTQ TYTCNVDHKPSNTKVDKTVERKCCVECPPCPAPPVAGPS |

TABLE OF SEQUENCES-continued

| SEQ ID NO: | Description | Sequence |
|---|---|---|
| | | VFLFPPKPKDTLMISRTPEVTCVVV**A**VSHEDPEVQFNWY VDGVEVHNAKTKPREEQF**G**STFRVVSVLTVVHQDWLN GKEYKCKVSNKGLPAPIEKTISKTKGQPREPQVYTLPPSR EEMTKNQVSLTCLVKGFYPSDISVEWESNGQPENNYKTT PPMLDSDGSFFLYSKLTVDKSRWQQGNVFSCSVMHEAL HNHYTQKSLSLSPGK |
| 51 | Human IgG2 HC Constant domain (N297X, wherein X is any amino acid other than N) | ASTKGPSVFPLAPCSRSTSESTAALGCLVKDYFPEPVTVS WNSGALTSGVHTFPAVLQSSGLYSLSSVVTVPSSNFGTQ TYTCNVDHKPSNTKVDKTVERKCCVECPPCPAPPVAGPS VFLFPPKPKDTLMISRTPEVTCVVVDVSHEDPEVQFNWY VDGVEVHNAKTKPREEQF**X**STFRVVSVLTVVHQDWLN GKEYKCKVSNKGLPAPIEKTISKTKGQPREPQVYTLPPSR EEMTKNQVSLTCLVKGFYPSDISVEWESNGQPENNYKTT PPMLDSDGSFFLYSKLTVDKSRWQQGNVFSCSVMHEAL HNHYTQKSLSLSPGK |
| 52 | Human IgG2 HC Constant domain (V234A G237A P238S H268A V309L A330S P331S X378S/A)(See IgGsigma SEQ ID No: 78 in WO2017079112) | ASTKGPSVFPLAPCSRSTSESTAALGCLVKDYFPEPVTVS WNSGALTSGVHTFPAVLQSSGLYSLSSVVTVPSSNFGTQ TYTCNVDHKPSNTKVDKTVERKCCVECPPCPAPP**AAA**SS VFLFPPKPKDTLMISRTPEVTCVVVDVS**A**EDPEVQFNWY VDGVEVHNAKTKPREEQFNSTFRVVSVLTV**L**HQDWLN GKEYKCKVSNKGLP**S**SIEKTISKTKGQPREPQVYTLPPSR EEMTKNQVSLTCLVKGFYPSDI**X**VEWESNGQPENNYKT TPPMLDSDGSFFLYSKLTVDKSRWQQGNVFSCSVMHEA LHNHYTQKSLSLSPGK |
| 53 | Human IgG4 HC Constant domain (S228P) | ASTKGPSVFPLAPCSRSTSESTAALGCLVKDYFPEPVTVS WNSGALTSGVHTFPAVLQSSGLYSLSSVVTVPSSSLGTK TYTCNVDHKPSNTKVDKRVESKYGPPCP**P**CPAPEFLGGP SVFLFPPKPKDTLMISRTPEVTCVVVDVSQEDPEVQFNW YVDGVEVHNAKTKPREEQFNSTYRVVSVLTVLHQDWL NGKEYKCKVSNKGLPSSIEKTISKAKGQPREPQVYTLPPS QEEMTKNQVSLTCLVKGFYPSDIAVEWESNGQPENNYK TTPPVLDSDGSFFLYSRLTVDKSRWQEGNVFSCSVMHEA LHNHYTQKSLSLSLGK |
| 54 | Human IgG4 HC Constant domain (S228P P329G) | ASTKGPSVFPLAPCSRSTSESTAALGCLVKDYFPEPVTVS WNSGALTSGVHTFPAVLQSSGLYSLSSVVTVPSSSLGTK TYTCNVDHKPSNTKVDKRVESKYGPPCP**P**CPAPEFLGGP SVFLFPPKPKDTLMISRTPEVTCVVVDVSQEDPEVQFNW YVDGVEVHNAKTKPREEQFNSTYRVVSVLTVLHQDWL NGKEYKCKVSNKGL**G**SSIEKTISKAKGQPREPQVYTLPP SQEEMTKNQVSLTCLVKGFYPSDIAVEWESNGQPENNY KTTPPVLDSDGSFFLYSRLTVDKSRWQEGNVFSCSVMHE ALHNHYTQKSLSLSLGK |
| 55 | Human IgG4 HC Constant domain (S228P D265A) | ASTKGPSVFPLAPCSRSTSESTAALGCLVKDYFPEPVTVS WNSGALTSGVHTFPAVLQSSGLYSLSSVVTVPSSSLGTK TYTCNVDHKPSNTKVDKRVESKYGPPCP**P**CPAPEFLGGP SVFLFPPKPKDTLMISRTPEVTCVVV**A**VSQEDPEVQFNW YVDGVEVHNAKTKPREEQFNSTYRVVSVLTVLHQDWL NGKEYKCKVSNKGLPSSIEKTISKAKGQPREPQVYTLPPS QEEMTKNQVSLTCLVKGFYPSDIAVEWESNGQPENNYK TTPPVLDSDGSFFLYSRLTVDKSRWQEGNVFSCSVMHEA LHNHYTQKSLSLSLGK |
| 56 | Human IgG4 HC Constant domain (S228P D265A N297G) | ASTKGPSVFPLAPCSRSTSESTAALGCLVKDYFPEPVTVS WNSGALTSGVHTFPAVLQSSGLYSLSSVVTVPSSSLGTK TYTCNVDHKPSNTKVDKRVESKYGPPCP**P**CPAPEFLGGP SVFLFPPKPKDTLMISRTPEVTCVVV**A**VSQEDPEVQFNW YVDGVEVHNAKTKPREEQFBSTYRVVSVLTVLHQDWL NGKEYKCKVSNKGLPSSIEKTISKAKGQPREPQVYTLPPS QEEMTKNQVSLTCLVKGFYPSDIAVEWESNGQPENNYK TTPPVLDSDGSFFLYSRLTVDKSRWQEGNVFSCSVMHEA LHNHYTQKSLSLSLGK |
| 57 | Human IgG4 HC Constant domain (S228P N297X, wherein X is any amino acid other than N) | ASTKGPSVFPLAPCSRSTSESTAALGCLVKDYFPEPVTVS WNSGALTSGVHTFPAVLQSSGLYSLSSVVTVPSSSLGTK TYTCNVDHKPSNTKVDKRVESKYGPPCP**P**CPAPEFLGGP SVFLFPPKPKDTLMISRTPEVTCVVVDVSQEDPEVQFNW YVDGVEVHNAKTKPREEQF**X**STYRVVSVLTVLHQDWL NGKEYKCKVSNKGLPSSIEKTISKAKGQPREPQVYTLPPS QEEMTKNQVSLTCLVKGFYPSDIAVEWESNGQPENNYK TTPPVLDSDGSFFLYSRLTVDKSRWQEGNVFSCSVMHEA LHNHYTQKSLSLSLGK |

TABLE OF SEQUENCES-continued

| SEQ ID NO: | Description | Sequence |
|---|---|---|
| 58 | Human LC Kappa Constant domain | RTVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC |
| 59 | Human IgG1 HC Constant domain (N297A/D356E/L358M) | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPELL GGPSVFLFPPKPKDTLMISRTPEVTCVVVDVSHEDPEVKF NWYVDGVEVHNAKTKPREEQYASTYRVVSVLTVLHQD WLNGKEYKCKVSNKALPAPIEKTISKAKGQPREPQVYTL PPSREEMTKNQVSLTCLVKGFYPSDIAVEWESNGQPENN YKTTPPVLDSDGSFFLYSKLTVDKSRWQQGNVFSCSVM HEALHNHYTQKSLSLSPGK |
| 60 | Human IgG1 HC Constant domain (L234F/L235E/P331S/ D356E/L358M) | ASTKGPSVFPLAPCSRSTSESTAALGCLVKDYFPEPVTVS WNSGALTSGVHTFPAVLQSSGLYSLSSVVTVPSSSLGTK TYTCNVDHKPSNTKVDKRVESKYGPPCPPCPAPEFLGGP SVFLFPPKPKDTLMISRTPEVTCVVVDVSQEDPEVQFNW YVDGVEVHNAKTKPREEQFNSTYRVVSVLTVLHQDWL NGKEYKCKVSNKGLPSSIEKTISKAKGQPREPQVYTLPPS LTCLVKGFYPSDIAVEWESNGQPENNYKTTPPVLDSDGS FFLYSRLTVDKSRWQEGNVFSCSVMHEALHNHYTQKSL SLSLGK |
| 61 | Human LC lambda Constant domain | GQPKANPTVTLFPPSSEELQANKATLVCLISDFYPGAVTV AWKADGSPVKAGVETTKPSKQSNNKYAASSYLSLTPEQ WKSHRSYSCQVTHEGSTVEKTVAPTECS |
| 62 | Mouse HC IgG1 (D265A) constant domain | AKTTPPSVYPLAPGSAAQTNSMVTLGCLVKGYFPEPVTV TWNSGSLSSGVHTFPAVLQSDLYTLSSSVTVPSSTWPSET VTCNVAHPASSTKVDKKIVPRDCGCKPCICTVPEVSSVFI FPPKPKDVLTITLTPKVTCVVVAISKDDPEVQFSWFVDD VEVHTAQTQPREEQFNSTFRSVSELPIMHQDWLNGKEFK CRVNSAAFPAPIEKTISKTKGRPKAPQVYTIPPPKEQMAK DKVSLTCMITDFFPEDITVEWQWNGQPAENYKNTQPIM DTDGSYFVYSKLNVQKSNWEAGNTFTCSVLHEGLHNHH TEKSLSHSPGK |
| 63 | Mouse HC IgG2 constant domain | AKTTAPSVYPLAPVCGDTTGSSVTLGCLVKGYFPEPVTL TWNSGSLSSGVHTFPAVLQSDLYTLSSSVTVTSSTWPSQ SITCNVAHPASSTKVDKKIEPRGPTIKPCPPCKCPAPNLLG GPSVFIFPPKIKDVLMISLSPIVTCVVVDVSEDDPDVQISW FVNNVEVHTAQTQTHREDYNSTLRVVSALPIQHQDWMS GKEFKCKVNNKDLPAPIERTISKPKGSVRAPQVYVLPPPE EEMTKKQVTLTCMVTDFMPEDIYVEWTNNGKTELNYK NTEPVLDSDGSYFMYSKLRVEKKNWVERNSYSCSVVHE GLHNHHTTKSFSRTPGK |
| 64 | Mouse LC kappa constant domain | RTVAAPTVSIFPPSSEQLTSGGASVVCFLNNFYPKDINVK WKIDGSERQNGVLNSWTDQDSKDSTYSMSSTLTLTKDE YERHNSYTCEATHKTSTSPIVKSFNRNEC |
| 65 | Nucleotide sequence encoding VH1 | CAGGTGCAGCTGGTGCAGAGCGGCGCCGAGGTGAAG AAGCCCGGCGCCAGCGTGAAGGTGAGCTGCAAGGCC AGCGGCTACACCTTCACCAACTACGGCATCAGCTGGG TGAGACAGGCCCCCGGCCAGGGCCTGGAGTGGATGGG CTGGATCAGCGCCTACAACGGCAACACCAACTACGCC CAGAAGCTGCAGGGCAGAGTGACCATGACCACCGAC ACCAGCACCAGCACCGCCTACATGGAGCTGAGAAGCC TGAGAAGCGACGACACCGCCGTGTACTACTGCGCCAG AGAGGGCGCCTACGGCTACAGAAGCCCCTACCACAAC TGGTTCGACCCCTGGGGCCAGGGCACCCTGGTGACCG TGAGCAGC |
| 66 | Nucleotide sequence encoding VH2 | GAGGTGCAGCTGGTGCAGAGCGGCGCCGAGGTGAAG AAGCCCGGCGCCAGCGTGAAGGTGAGCTGCAAGGCC AGCGGCTACACCTTCTTCAAGTACGGCATCAGCTGGG TGAGACAGGCCCCCGGCCAGGGCCTGGAGTGGATGGG CAGCATCAGCCCCTACACCGGCGAGACCCACTACGCC CAGAAGCTGCAGGGCAGAGTGACCATGACCACCGAC ACCAGCACCAGCACCGCCTACATGGAGCTGAGAAGCC TGAGAAGCGACGACACCGCCGTGTACTACTGCGCCAG AGAGGGCGCCTACGGCTACAGAAGCCCCTACCAGAAC TGGTTCGACCCCTGGGGCCAGGGCACCCTGGTGACCG TGAGCAGC |

TABLE OF SEQUENCES-continued

| SEQ ID NO: | Description | Sequence |
|---|---|---|
| 67 | Nucleotide sequence encoding VL | GAGATCGTGATGACCCAGAGCCCCGCCACCCTGAGCC TGAGCCCCGGCGAGAGAGCCACCCTGAGCTGCAGAGC CAGCCAGAGCGTGAGCAGCTACCTGGCCTGGTACCAG CAGAAGCCCGGCCAGGCCCCCAGACTGCTGATCTACG ACGCCAGCAACAGAGCCACCGGCATCCCCGCCAGATT CAGCGGCAGCGGCAGCGGCACCGACTTCACCCTGACC ATCAGCAGCCTGGAGCCCGAGGACTTCGCCGTGTACT ACTGCCAGCAGCACAGCCTGCTGCCCAGAACCTTCGG CGGCGGCACCAAGGTGGAGATCAAG |
| 68 | Nucleotide sequence encoding human IgG1 HC constant domain | GCCAGCACCAAGGGCCCCAGCGTGTTCCCCCTGGCCC CCAGCAGCAAGAGCACCAGCGGCGGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AGCCTGGGCACCCAGACCTACATCTGCAACGTGAACC ACAAGCCCAGCAACACCAAGGTGGACAAGAAGGTGG AGCCCAAGAGCTGCGACAAGACCCACACCTGCCCCCC CTGCCCCGCCCCCGAGCTGCTGGGCGGCCCCAGCGTG TTCCTGTTCCCCCCCAAGCCCAAGGACACCCTGATGAT CAGCAGAACCCCCGAGGTGACCTGCGTGGTGGTGGAC GTGAGCCACGAGGACCCCGAGGTGAAGTTCAACTGGT ACGTGGACGGCGTGGAGGTGCACAACGCCAAGACCA AGCCCAGAGAGGAGCAGTACAACAGCACCTACAGAG TGGTGAGCGTGCTGACCGTGCTGCACCAGGACTGGCT GAACGGCAAGGAGTACAAGTGCAAGGTGAGCAACAA GGCCCTGCCCGCCCCCATCGAGAAGACCATCAGCAAG GCCAAGGGCCAGCCCAGAGAGCCCCAGGTGTACACCC TGCCCCCCAGCAGAGACGAGCTGACCAAGAACCAGGT GAGCCTGACCTGCCTGGTGAAGGGCTTCTACCCCAGC GACATCGCCGTGGAGTGGGAGAGCAACGGCCAGCCC GAGAACAACTACAAGACCACCCCCCCCGTGCTGGACA GCGACGGCAGCTTCTTCCTGTACAGCAAGCTGACCGT GGACAAGAGCAGATGGCAGCAGGGCAACGTGTTCAG CTGCAGCGTGATGCACGAGGCCCTGCACAACCACTAC ACCCAGAAGAGCCTGAGCCTGAGCCCCGGCAAG |
| 69 | Nucleotide sequence encoding human IgG1 HC Constant domain (L234A L235A D265S) | GCCAGCACCAAGGGCCCCAGCGTGTTCCCCCTGGCCC CCAGCAGCAAGAGCACCAGCGGCGGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AGCCTGGGCACCCAGACCTACATCTGCAACGTGAACC ACAAGCCCAGCAACACCAAGGTGGACAAGAAGGTGG AGCCCAAGAGCTGCGACAAGACCCACACCTGCCCCCC CTGCCCCGCCCCCGAGGCCGCCGGCGGCCCCAGCGTG TTCCTGTTCCCCCCCAAGCCCAAGGACACCCTGATGAT CAGCAGAACCCCCGAGGTGACCTGCGTGGTGGTGAGC GTGAGCCACGAGGACCCCGAGGTGAAGTTCAACTGGT ACGTGGACGGCGTGGAGGTGCACAACGCCAAGACCA AGCCCAGAGAGGAGCAGTACAACAGCACCTACAGAG TGGTGAGCGTGCTGACCGTGCTGCACCAGGACTGGCT GAACGGCAAGGAGTACAAGTGCAAGGTGAGCAACAA GGCCCTGCCCGCCCCCATCGAGAAGACCATCAGCAAG GCCAAGGGCCAGCCCAGAGAGCCCCAGGTGTACACCC TGCCCCCCAGCAGAGACGAGCTGACCAAGAACCAGGT GAGCCTGACCTGCCTGGTGAAGGGCTTCTACCCCAGC GACATCGCCGTGGAGTGGGAGAGCAACGGCCAGCCC GAGAACAACTACAAGACCACCCCCCCCGTGCTGGACA GCGACGGCAGCTTCTTCCTGTACAGCAAGCTGACCGT GGACAAGAGCAGATGGCAGCAGGGCAACGTGTTCAG CTGCAGCGTGATGCACGAGGCCCTGCACAACCACTAC ACCCAGAAGAGCCTGAGCCTGAGCCCCGGCAAG |
| 70 | Nucleotide sequence encoding human IgG1 HC Constant domain (L234A L235A P329G) | GCCAGCACCAAGGGCCCCAGCGTGTTCCCCCTGGCCC CCAGCAGCAAGAGCACCAGCGGCGGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AGCCTGGGCACCCAGACCTACATCTGCAACGTGAACC ACAAGCCCAGCAACACCAAGGTGGACAAGAAGGTGG AGCCCAAGAGCTGCGACAAGACCCACACCTGCCCCCC |

TABLE OF SEQUENCES-continued

| SEQ ID NO: | Description | Sequence |
|---|---|---|
| | | CTGCCCCGCCCCCGAGGCCGCCGGCGGCCCCAGCGTG<br>TTCCTGTTCCCCCCCAAGCCCAAGGACACCCTGATGAT<br>CAGCAGAACCCCCGAGGTGACCTGCGTGGTGGTGAGC<br>GTGAGCCACGAGGACCCCGAGGTGAAGTTCAACTGGT<br>ACGTGGACGGCGTGGAGGTGCACAACGCCAAGACCA<br>AGCCCAGAGAGGAGCAGTACAACAGCACCTACAGAG<br>TGGTGAGCGTGCTGACCGTGCTGCACCAGGACTGGCT<br>GAACGGCAAGGAGTACAAGTGCAAGGTGAGCAACAA<br>GGCCCTGGGCGCCCCCATCGAGAAGACCATCAGCAAG<br>GCCAAGGGCCAGCCCAGAGAGCCCCAGGTGTACACCC<br>TGCCCCCCAGCAGAGACGAGCTGACCAAGAACCAGGT<br>GAGCCTGACCTGCCTGGTGAAGGGCTTCTACCCCAGC<br>GACATCGCCGTGGAGTGGGAGAGCAACGGCCAGCCC<br>GAGAACAACTACAAGACCACCCCCCCCGTGCTGGACA<br>GCGACGGCAGCTTCTTCCTGTACAGCAAGCTGACCGT<br>GGACAAGAGCAGATGGCAGCAGGGCAACGTGTTCAG<br>CTGCAGCGTGATGCACGAGGCCCTGCACAACCACTAC<br>ACCCAGAAGAGCCTGAGCCTGAGCCCCGGCAAG |
| 71 | Nucleotide sequence encoding human IgG1 HC Constant domain (L235E) | GCCAGCACCAAGGGCCCCAGCGTGTTCCCCCTGGCCC<br>CCAGCAGCAAGAGCACCAGCGGCGGCACCGCCGCCCT<br>GGGCTGCCTGGTGAAGGACTACTTCCCCGAGCCCGTG<br>ACCGTGAGCTGGAACAGCGGCGCCCTGACCAGCGGCG<br>TGCACACCTTCCCCGCCGTGCTGCAGAGCAGCGGCCT<br>GTACAGCCTGAGCAGCGTGGTGACCGTGCCCAGCAGC<br>AGCCTGGGCACCCAGACCTACATCTGCAACGTGAACC<br>ACAAGCCCAGCAACACCAAGGTGGACAAGAAGGTGG<br>AGCCCAAGAGCTGCGACAAGACCCACACCTGCCCCCC<br>CTGCCCCGCCCCCGAGCTGGAGGGCGGCCCCAGCGTG<br>TTCCTGTTCCCCCCCAAGCCCAAGGACACCCTGATGAT<br>CAGCAGAACCCCCGAGGTGACCTGCGTGGTGGTGGAC<br>GTGAGCCACGAGGACCCCGAGGTGAAGTTCAACTGGT<br>ACGTGGACGGCGTGGAGGTGCACAACGCCAAGACCA<br>AGCCCAGAGAGGAGCAGTACAACAGCACCTACAGAG<br>TGGTGAGCGTGCTGACCGTGCTGCACCAGGACTGGCT<br>GAACGGCAAGGAGTACAAGTGCAAGGTGAGCAACAA<br>GGCCCTGCCCGCCCCCATCGAGAAGACCATCAGCAAG<br>GCCAAGGGCCAGCCCAGAGAGCCCCAGGTGTACACCC<br>TGCCCCCCAGCAGAGACGAGCTGACCAAGAACCAGGT<br>GAGCCTGACCTGCCTGGTGAAGGGCTTCTACCCCAGC<br>GACATCGCCGTGGAGTGGGAGAGCAACGGCCAGCCC<br>GAGAACAACTACAAGACCACCCCCCCCGTGCTGGACA<br>GCGACGGCAGCTTCTTCCTGTACAGCAAGCTGACCGT<br>GGACAAGAGCAGATGGCAGCAGGGCAACGTGTTCAG<br>CTGCAGCGTGATGCACGAGGCCCTGCACAACCACTAC<br>ACCCAGAAGAGCCTGAGCCTGAGCCCCGGCAAG |
| 72 | Nucleotide sequence encoding human IgG1 HC Constant domain (D265A) | GCCAGCACCAAGGGCCCCAGCGTGTTCCCCCTGGCCC<br>CCAGCAGCAAGAGCACCAGCGGCGGCACCGCCGCCCT<br>GGGCTGCCTGGTGAAGGACTACTTCCCCGAGCCCGTG<br>ACCGTGAGCTGGAACAGCGGCGCCCTGACCAGCGGCG<br>TGCACACCTTCCCCGCCGTGCTGCAGAGCAGCGGCCT<br>GTACAGCCTGAGCAGCGTGGTGACCGTGCCCAGCAGC<br>AGCCTGGGCACCCAGACCTACATCTGCAACGTGAACC<br>ACAAGCCCAGCAACACCAAGGTGGACAAGAAGGTGG<br>AGCCCAAGAGCTGCGACAAGACCCACACCTGCCCCCC<br>CTGCCCCGCCCCCGAGCTGCTGGGCGGCCCCAGCGTG<br>TTCCTGTTCCCCCCCAAGCCCAAGGACACCCTGATGAT<br>CAGCAGAACCCCCGAGGTGACCTGCGTGGTGGTGGCC<br>GTGAGCCACGAGGACCCCGAGGTGAAGTTCAACTGGT<br>ACGTGGACGGCGTGGAGGTGCACAACGCCAAGACCA<br>AGCCCAGAGAGGAGCAGTACAACAGCACCTACAGAG<br>TGGTGAGCGTGCTGACCGTGCTGCACCAGGACTGGCT<br>GAACGGCAAGGAGTACAAGTGCAAGGTGAGCAACAA<br>GGCCCTGCCCGCCCCCATCGAGAAGACCATCAGCAAG<br>GCCAAGGGCCAGCCCAGAGAGCCCCAGGTGTACACCC<br>TGCCCCCCAGCAGAGACGAGCTGACCAAGAACCAGGT<br>GAGCCTGACCTGCCTGGTGAAGGGCTTCTACCCCAGC<br>GACATCGCCGTGGAGTGGGAGAGCAACGGCCAGCCC<br>GAGAACAACTACAAGACCACCCCCCCCGTGCTGGACA<br>GCGACGGCAGCTTCTTCCTGTACAGCAAGCTGACCGT<br>GGACAAGAGCAGATGGCAGCAGGGCAACGTGTTCAG<br>CTGCAGCGTGATGCACGAGGCCCTGCACAACCACTAC<br>ACCCAGAAGAGCCTGAGCCTGAGCCCCGGCAAG |

TABLE OF SEQUENCES-continued

| SEQ ID NO: | Description | Sequence |
|---|---|---|
| 73 | Nucleotide sequence encoding human IgG1 HC Constant domain (D265A N297G) | GCCAGCACCAAGGGCCCCAGCGTGTTCCCCCTGGCCC CCAGCAGCAAGAGCACCAGCGGCGGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AGCCTGGGCACCCAGACCTACATCTGCAACGTGAACC ACAAGCCCAGCAACACCAAGGTGGACAAGAAGGTGG AGCCCAAGAGCTGCGACAAGACCCACACCTGCCCCCC CTGCCCCGCCCCCGAGCTGCTGGGCGGCCCCAGCGTG TTCCTGTTCCCCCCCAAGCCCAAGGACACCCTGATGAT CAGCAGAACCCCCGAGGTGACCTGCGTGGTGGTGGCC GTGAGCCACGAGGACCCCGAGGTGAAGTTCAACTGGT ACGTGGACGGCGTGGAGGTGCACAACGCCAAGACCA AGCCCAGAGAGGAGCAGTACGGCAGCACCTACAGAG TGGTGAGCGTGCTGACCGTGCTGCACCAGGACTGGCT GAACGGCAAGGAGTACAAGTGCAAGGTGAGCAACAA GGCCCTGCCCGCCCCCATCGAGAAGACCATCAGCAAG GCCAAGGGCCAGCCCAGAGAGCCCCAGGTGTACACCC TGCCCCCCAGCAGAGACGAGCTGACCAAGAACCAGGT GAGCCTGACCTGCCTGGTGAAGGGCTTCTACCCCAGC GACATCGCCGTGGAGTGGGAGAGCAACGGCCAGCCC GAGAACAACTACAAGACCACCCCCCCCGTGCTGGACA GCGACGGCAGCTTCTTCCTGTACAGCAAGCTGACCGT GGACAAGAGCAGATGGCAGCAGGGCAACGTGTTCAG CTGCAGCGTGATGCACGAGGCCCTGCACAACCACTAC ACCCAGAAGAGCCTGAGCCTGAGCCCCGGCAAG |
| 74 | Nucleotide sequence encoding human IgG1 HC Constant domain (E233A/L235A) | GCCAGCACCAAGGGCCCCAGCGTGTTCCCCCTGGCCC CCAGCAGCAAGAGCACCAGCGGCGGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AGCCTGGGCACCCAGACCTACATCTGCAACGTGAACC ACAAGCCCAGCAACACCAAGGTGGACAAGAAGGTGG AGCCCAAGAGCTGCGACAAGACCCACACCTGCCCCCC CTGCCCCGCCCCCGCCCTGGCCGGCGGCCCCAGCGTG TTCCTGTTCCCCCCCAAGCCCAAGGACACCCTGATGAT CAGCAGAACCCCCGAGGTGACCTGCGTGGTGGTGGAC GTGAGCCACGAGGACCCCGAGGTGAAGTTCAACTGGT ACGTGGACGGCGTGGAGGTGCACAACGCCAAGACCA AGCCCAGAGAGGAGCAGTACAACAGCACCTACAGAG TGGTGAGCGTGCTGACCGTGCTGCACCAGGACTGGCT GAACGGCAAGGAGTACAAGTGCAAGGTGAGCAACAA GGCCCTGCCCGCCCCCATCGAGAAGACCATCAGCAAG GCCAAGGGCCAGCCCAGAGAGCCCCAGGTGTACACCC TGCCCCCCAGCAGAGACGAGCTGACCAAGAACCAGGT GAGCCTGACCTGCCTGGTGAAGGGCTTCTACCCCAGC GACATCGCCGTGGAGTGGGAGAGCAACGGCCAGCCC GAGAACAACTACAAGACCACCCCCCCCGTGCTGGACA GCGACGGCAGCTTCTTCCTGTACAGCAAGCTGACCGT GGACAAGAGCAGATGGCAGCAGGGCAACGTGTTCAG CTGCAGCGTGATGCACGAGGCCCTGCACAACCACTAC ACCCAGAAGAGCCTGAGCCTGAGCCCCGGCAAG |
| 75 | Nucleotide sequence encoding human IgG1 HC Constant domain (N297X, wherein X is any amino acid other than N); codon 538-540 wherein N is any nucleotide with the proviso that the codon does not encode Asn or form a translation stop codon | GCCAGCACCAAGGGCCCCAGCGTGTTCCCCCTGGCCC CCAGCAGCAAGAGCACCAGCGGCGGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AGCCTGGGCACCCAGACCTACATCTGCAACGTGAACC ACAAGCCCAGCAACACCAAGGTGGACAAGAAGGTGG AGCCCAAGAGCTGCGACAAGACCCACACCTGCCCCCC CTGCCCCGCCCCCGAGCTGCTGGGCGGCCCCAGCGTG TTCCTGTTCCCCCCCAAGCCCAAGGACACCCTGATGAT CAGCAGAACCCCCGAGGTGACCTGCGTGGTGGTGGAC GTGAGCCACGAGGACCCCGAGGTGAAGTTCAACTGGT ACGTGGACGGCGTGGAGGTGCACAACGCCAAGACCA AGCCCAGAGAGGAGCAGTACNNNAGCACCTACAGAG TGGTGAGCGTGCTGACCGTGCTGCACCAGGACTGGCT GAACGGCAAGGAGTACAAGTGCAAGGTGAGCAACAA GGCCCTGCCCGCCCCCATCGAGAAGACCATCAGCAAG GCCAAGGGCCAGCCCAGAGAGCCCCAGGTGTACACCC |

TABLE OF SEQUENCES-continued

| SEQ ID NO: | Description | Sequence |
|---|---|---|
| | | TGCCCCCCAGCAGAGACGAGCTGACCAAGAACCAGGT GAGCCTGACCTGCCTGGTGAAGGGCTTCTACCCCAGC GACATCGCCGTGGAGTGGGAGAGCAACGGCCAGCCC GAGAACAACTACAAGACCACCCCCCCCGTGCTGGACA GCGACGGCAGCTTCTTCCTGTACAGCAAGCTGACCGT GGACAAGAGCAGATGGCAGCAGGGCAACGTGTTCAG CTGCAGCGTGATGCACGAGGCCCTGCACAACCACTAC ACCCAGAAGAGCCTGAGCCTGAGCCCCGGCAAG |
| 76 | Nucleotide sequence encoding human IgG2 HC Constant domain | GCCAGCACCAAGGGCCCCAGCGTGTTCCCCCTGGCCC CCTGCAGCAGAAGCACCAGCGAGAGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AACTTCGGCACCCAGACCTACACCTGCAACGTGGACC ACAAGCCCAGCAACACCAAGGTGGACAAGACCGTGG AGAGAAAGTGCTGCGTGGAGTGCCCCCCCTGCCCCGC CCCCCCCGTGGCCGGCCCCAGCGTGTTCCTGTTCCCCC CCAAGCCCAAGGACACCCTGATGATCAGCAGAACCCC CGAGGTGACCTGCGTGGTGGTGGACGTGAGCCACGAG GACCCCGAGGTGCAGTTCAACTGGTACGTGGACGGCG TGGAGGTGCACAACGCCAAGACCAAGCCCAGAGAGG AGCAGTTCAACAGCACCTTCAGAGTGGTGAGCGTGCT GACCGTGGTGCACCAGGACTGGCTGAACGGCAAGGA GTACAAGTGCAAGGTGAGCAACAAGGGCCTGCCCGCC CCCATCGAGAAGACCATCAGCAAGACCAAGGGCCAG CCCAGAGAGCCCCAGGTGTACACCCTGCCCCCCAGCA GAGAGGAGATGACCAAGAACCAGGTGAGCCTGACCT GCCTGGTGAAGGGCTTCTACCCCAGCGACATCAGCGT GGAGTGGGAGAGCAACGGCCAGCCCGAGAACAACTA CAAGACCACCCCCCCCATGCTGGACAGCGACGGCAGC TTCTTCCTGTACAGCAAGCTGACCGTGGACAAGAGCA GATGGCAGCAGGGCAACGTGTTCAGCTGCAGCGTGAT GCACGAGGCCCTGCACAACCACTACACCCAGAAGAGC CTGAGCCTGAGCCCCGGCAAG |
| 77 | Nucleotide sequence encoding human IgG2 HC Constant domain (D265S) | GCCAGCACCAAGGGCCCCAGCGTGTTCCCCCTGGCCC CCTGCAGCAGAAGCACCAGCGAGAGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AACTTCGGCACCCAGACCTACACCTGCAACGTGGACC ACAAGCCCAGCAACACCAAGGTGGACAAGACCGTGG AGAGAAAGTGCTGCGTGGAGTGCCCCCCCTGCCCCGC CCCCCCCGTGGCCGGCCCCAGCGTGTTCCTGTTCCCCC CCAAGCCCAAGGACACCCTGATGATCAGCAGAACCCC CGAGGTGACCTGCGTGGTGGTGAGCGTGAGCCACGAG GACCCCGAGGTGCAGTTCAACTGGTACGTGGACGGCG TGGAGGTGCACAACGCCAAGACCAAGCCCAGAGAGG AGCAGTTCAACAGCACCTTCAGAGTGGTGAGCGTGCT GACCGTGGTGCACCAGGACTGGCTGAACGGCAAGGA GTACAAGTGCAAGGTGAGCAACAAGGGCCTGCCCGCC CCCATCGAGAAGACCATCAGCAAGACCAAGGGCCAG CCCAGAGAGCCCCAGGTGTACACCCTGCCCCCCAGCA GAGAGGAGATGACCAAGAACCAGGTGAGCCTGACCT GCCTGGTGAAGGGCTTCTACCCCAGCGACATCAGCGT GGAGTGGGAGAGCAACGGCCAGCCCGAGAACAACTA CAAGACCACCCCCCCCATGCTGGACAGCGACGGCAGC TTCTTCCTGTACAGCAAGCTGACCGTGGACAAGAGCA GATGGCAGCAGGGCAACGTGTTCAGCTGCAGCGTGAT GCACGAGGCCCTGCACAACCACTACACCCAGAAGAGC CTGAGCCTGAGCCCCGGCAAG |
| 78 | Nucleotide sequence encoding human IgG2 HC Constant domain (P329G) | GCCAGCACCAAGGGCCCCAGCGTGTTCCCCCTGGCCC CCTGCAGCAGAAGCACCAGCGAGAGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AACTTCGGCACCCAGACCTACACCTGCAACGTGGACC ACAAGCCCAGCAACACCAAGGTGGACAAGACCGTGG AGAGAAAGTGCTGCGTGGAGTGCCCCCCCTGCCCCGC CCCCCCCGTGGCCGGCCCCAGCGTGTTCCTGTTCCCCC CCAAGCCCAAGGACACCCTGATGATCAGCAGAACCCC |

TABLE OF SEQUENCES-continued

| SEQ ID NO: | Description | Sequence |
| --- | --- | --- |
| | | CGAGGTGACCTGCGTGGTGGTGGACGTGAGCCACGAG<br>GACCCCGAGGTGCAGTTCAACTGGTACGTGGACGGCG<br>TGGAGGTGCACAACGCCAAGACCAAGCCCAGAGAGG<br>AGCAGTTCAACAGCACCTTCAGAGTGGTGAGCGTGCT<br>GACCGTGGTGCACCAGGACTGGCTGAACGGCAAGGA<br>GTACAAGTGCAAGGTGAGCAACAAGGGCCTGGGCGC<br>CCCCATCGAGAAGACCATCAGCAAGACCAAGGGCCA<br>GCCCAGAGAGCCCCAGGTGTACACCCTGCCCCCCAGC<br>AGAGAGGAGATGACCAAGAACCAGGTGAGCCTGACC<br>TGCCTGGTGAAGGGCTTCTACCCCAGCGACATCAGCG<br>TGGAGTGGGAGAGCAACGGCCAGCCCGAGAACAACT<br>ACAAGACCACCCCCCCCATGCTGGACAGCGACGGCAG<br>CTTCTTCCTGTACAGCAAGCTGACCGTGGACAAGAGC<br>AGATGGCAGCAGGGCAACGTGTTCAGCTGCAGCGTGA<br>TGCACGAGGCCCTGCACAACCACTACACCCAGAAGAG<br>CCTGAGCCTGAGCCCCGGCAAG |
| 79 | Nucleotide sequence encoding human IgG2 HC Constant domain (D265A) | GCCAGCACCAAGGGCCCCAGCGTGTTCCCCCTGGCCC<br>CCTGCAGCAGAAGCACCAGCGAGAGCACCGCCGCCCT<br>GGGCTGCCTGGTGAAGGACTACTTCCCCGAGCCCGTG<br>ACCGTGAGCTGGAACAGCGGCGCCCTGACCAGCGGCG<br>TGCACACCTTCCCCGCCGTGCTGCAGAGCAGCGGCCT<br>GTACAGCCTGAGCAGCGTGGTGACCGTGCCCAGCAGC<br>AACTTCGGCACCCAGACCTACACCTGCAACGTGGACC<br>ACAAGCCCAGCAACACCAAGGTGGACAAGACCGTGG<br>AGAGAAAGTGCTGCGTGGAGTGCCCCCCCTGCCCCGC<br>CCCCCCCGTGGCCGGCCCCAGCGTGTTCCTGTTCCCCC<br>CCAAGCCCAAGGACACCCTGATGATCAGCAGAACCCC<br>CGAGGTGACCTGCGTGGTGGTGGCCGTGAGCCACGAG<br>GACCCCGAGGTGCAGTTCAACTGGTACGTGGACGGCG<br>TGGAGGTGCACAACGCCAAGACCAAGCCCAGAGAGG<br>AGCAGTTCAACAGCACCTTCAGAGTGGTGAGCGTGCT<br>GACCGTGGTGCACCAGGACTGGCTGAACGGCAAGGA<br>GTACAAGTGCAAGGTGAGCAACAAGGGCCTGCCCGCC<br>CCCATCGAGAAGACCATCAGCAAGACCAAGGGCCAG<br>CCCAGAGAGCCCCAGGTGTACACCCTGCCCCCCAGCA<br>GAGAGGAGATGACCAAGAACCAGGTGAGCCTGACCT<br>GCCTGGTGAAGGGCTTCTACCCCAGCGACATCAGCGT<br>GGAGTGGGAGAGCAACGGCCAGCCCGAGAACAACTA<br>CAAGACCACCCCCCCCATGCTGGACAGCGACGGCAGC<br>TTCTTCCTGTACAGCAAGCTGACCGTGGACAAGAGCA<br>GATGGCAGCAGGGCAACGTGTTCAGCTGCAGCGTGAT<br>GCACGAGGCCCTGCACAACCACTACACCCAGAAGAGC<br>CTGAGCCTGAGCCCCGGCAAG |
| 80 | Nucleotide sequence encoding human IgG2 HC Constant domain (D265A N297G) | GCCAGCACCAAGGGCCCCAGCGTGTTCCCCCTGGCCC<br>CCTGCAGCAGAAGCACCAGCGAGAGCACCGCCGCCCT<br>GGGCTGCCTGGTGAAGGACTACTTCCCCGAGCCCGTG<br>ACCGTGAGCTGGAACAGCGGCGCCCTGACCAGCGGCG<br>TGCACACCTTCCCCGCCGTGCTGCAGAGCAGCGGCCT<br>GTACAGCCTGAGCAGCGTGGTGACCGTGCCCAGCAGC<br>AACTTCGGCACCCAGACCTACACCTGCAACGTGGACC<br>ACAAGCCCAGCAACACCAAGGTGGACAAGACCGTGG<br>AGAGAAAGTGCTGCGTGGAGTGCCCCCCCTGCCCCGC<br>CCCCCCCGTGGCCGGCCCCAGCGTGTTCCTGTTCCCCC<br>CCAAGCCCAAGGACACCCTGATGATCAGCAGAACCCC<br>CGAGGTGACCTGCGTGGTGGTGGCCGTGAGCCACGAG<br>GACCCCGAGGTGCAGTTCAACTGGTACGTGGACGGCG<br>TGGAGGTGCACAACGCCAAGACCAAGCCCAGAGAGG<br>AGCAGTTCGGCAGCACCTTCAGAGTGGTGAGCGTGCT<br>GACCGTGGTGCACCAGGACTGGCTGAACGGCAAGGA<br>GTACAAGTGCAAGGTGAGCAACAAGGGCCTGCCCGCC<br>CCCATCGAGAAGACCATCAGCAAGACCAAGGGCCAG<br>CCCAGAGAGCCCCAGGTGTACACCCTGCCCCCCAGCA<br>GAGAGGAGATGACCAAGAACCAGGTGAGCCTGACCT<br>GCCTGGTGAAGGGCTTCTACCCCAGCGACATCAGCGT<br>GGAGTGGGAGAGCAACGGCCAGCCCGAGAACAACTA<br>CAAGACCACCCCCCCCATGCTGGACAGCGACGGCAGC<br>TTCTTCCTGTACAGCAAGCTGACCGTGGACAAGAGCA<br>GATGGCAGCAGGGCAACGTGTTCAGCTGCAGCGTGAT<br>GCACGAGGCCCTGCACAACCACTACACCCAGAAGAGC<br>CTGAGCCTGAGCCCCGGCAAG |
| 81 | Nucleotide sequence encoding human IgG2 HC Constant domain | GCCAGCACCAAGGGCCCCAGCGTGTTCCCCCTGGCCC<br>CCTGCAGCAGAAGCACCAGCGAGAGCACCGCCGCCCT<br>GGGCTGCCTGGTGAAGGACTACTTCCCCGAGCCCGTG |

TABLE OF SEQUENCES-continued

| SEQ ID NO: | Description | Sequence |
|---|---|---|
| | (N297X, wherein X is any amino acid other than N); codon 526-528 wherein N is any nucleotide with the proviso that the codon does not encode Asn or form a translation stop codon | ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AACTTCGGCACCCAGACCTACACCTGCAACGTGGACC ACAAGCCCAGCAACACCAAGGTGGACAAGACCGTGG AGAGAAAGTGCTGCGTGGAGTGCCCCCCCTGCCCCGC CCCCCCCGTGGCCGGCCCCAGCGTGTTCCTGTTCCCCC CCAAGCCCAAGGACACCCTGATGATCAGCAGAACCCC CGAGGTGACCTGCGTGGTGGTGGACGTGAGCCACGAG GACCCCGAGGTGCAGTTCAACTGGTACGTGGACGGCG TGGAGGTGCACAACGCCAAGACCAAGCCCAGAGAGG AGCAGTTCNNNAGCACCTTCAGAGTGGTGAGCGTGCT GACCGTGGTGCACCAGGACTGGCTGAACGGCAAGGA GTACAAGTGCAAGGTGAGCAACAAGGGCCTGCCCGCC CCCATCGAGAAGACCATCAGCAAGACCAAGGGCCAG CCCAGAGAGCCCCAGGTGTACACCCTGCCCCCCAGCA GAGAGGAGATGACCAAGAACCAGGTGAGCCTGACCT GCCTGGTGAAGGGCTTCTACCCCAGCGACATCAGCGT GGAGTGGGAGAGCAACGGCCAGCCCGAGAACAACTA CAAGACCACCCCCCCCATGCTGGACAGCGACGGCAGC TTCTTCCTGTACAGCAAGCTGACCGTGGACAAGAGCA GATGGCAGCAGGGCAACGTGTTCAGCTGCAGCGTGAT GCACGAGGCCCTGCACAACCACTACACCCAGAAGAGC CTGAGCCTGAGCCCCGGCAAG |
| 82 | Nucleotide sequence encoding human IgG2 HC Constant domain (V234A G237A P238S H268A V309L A330S P331S X378S/A)(See IgGsigma SEQ ID No: 78 in WO2017079112) | GCCAGCACCAAGGGCCCCAGCGTGTTCCCCCTGGCCC CCTGCAGCAGAAGCACCAGCGAGAGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AACTTCGGCACCCAGACCTACACCTGCAACGTGGACC ACAAGCCCAGCAACACCAAGGTGGACAAGACCGTGG AGAGAAAGTGCTGCGTGGAGTGCCCCCCCTGCCCCGC CCCCCCCGCCGCCGCCAGCAGCGTGTTCCTGTTCCCCC CCAAGCCCAAGGACACCCTGATGATCAGCAGAACCCC CGAGGTGACCTGCGTGGTGGTGGACGTGAGCGCCGAG GACCCCGAGGTGCAGTTCAACTGGTACGTGGACGGCG TGGAGGTGCACAACGCCAAGACCAAGCCCAGAGAGG AGCAGTTCAACAGCACCTTCAGAGTGGTGAGCGTGCT GACCGTGCTGCACCAGGACTGGCTGAACGGCAAGGAG TACAAGTGCAAGGTGAGCAACAAGGGCCTGCCCAGCA GCATCGAGAAGACCATCAGCAAGACCAAGGGCCAGC CCAGAGAGCCCCAGGTGTACACCCTGCCCCCCAGCAG AGAGGAGATGACCAAGAACCAGGTGAGCCTGACCTG CCTGGTGAAGGGCTTCTACCCCAGCGACATCNNNGTG GAGTGGGAGAGCAACGGCCAGCCCGAGAACAACTAC AAGACCACCCCCCCCATGCTGGACAGCGACGGCAGCT TCTTCCTGTACAGCAAGCTGACCGTGGACAAGAGCAG ATGGCAGCAGGGCAACGTGTTCAGCTGCAGCGTGATG CACGAGGCCCTGCACAACCACTACACCCAGAAGAGCC TGAGCCTGAGCCCCGGCAAG |
| 83 | Nucleotide sequence encoding human IgG4 HC Constant domain (S228P) | GCCAGCACCAAGGGCCCCAGCGTGTTCCCCCTGGCCC CCTGCAGCAGAAGCACCAGCGAGAGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AGCCTGGGCACCAAGACCTACACCTGCAACGTGGACC ACAAGCCCAGCAACACCAAGGTGGACAAGAGAGTGG AGAGCAAGTACGGCCCCCCCTGCCCCCCCTGCCCCGC CCCCGAGTTCCTGGGCGGCCCCAGCGTGTTCCTGTTCC CCCCCAAGCCCAAGGACACCCTGATGATCAGCAGAAC CCCCGAGGTGACCTGCGTGGTGGTGGACGTGAGCCAG GAGGACCCCGAGGTGCAGTTCAACTGGTACGTGGACG GCGTGGAGGTGCACAACGCCAAGACCAAGCCCAGAG AGGAGCAGTTCAACAGCACCTACAGAGTGGTGAGCGT GCTGACCGTGCTGCACCAGGACTGGCTGAACGGCAAG GAGTACAAGTGCAAGGTGAGCAACAAGGGCCTGCCC AGCAGCATCGAGAAGACCATCAGCAAGGCCAAGGGC CAGCCCAGAGAGCCCCAGGTGTACACCCTGCCCCCCA GCCAGGAGGAGATGACCAAGAACCAGGTGAGCCTGA CCTGCCTGGTGAAGGGCTTCTACCCCAGCGACATCGC CGTGGAGTGGGAGAGCAACGGCCAGCCCGAGAACAA CTACAAGACCACCCCCCCCGTGCTGGACAGCGACGGC |

TABLE OF SEQUENCES-continued

| SEQ ID NO: | Description | Sequence |
|---|---|---|
| | | AGCTTCTTCCTGTACAGCAGACTGACCGTGGACAAGA GCAGATGGCAGGAGGGCAACGTGTTCAGCTGCAGCGT GATGCACGAGGCCCTGCACAACCACTACACCCAGAAG AGCCTGAGCCTGAGCCTGGGCAAG |
| 84 | Nucleotide sequence encoding human IgG4 HC Constant domain (S228P P329G) | GCCAGCACCAAGGGCCCCAGCGTGTTCCCCCTGGCCC CCTGCAGCAGAAGCACCAGCGAGAGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AGCCTGGGCACCAAGACCTACACCTGCAACGTGGACC ACAAGCCCAGCAACACCAAGGTGGACAAGAGAGTGG AGAGCAAGTACGGCCCCCCCTGCCCCCCCTGCCCCGC CCCCGAGTTCCTGGGCGGCCCCAGCGTGTTCCTGTTCC CCCCCAAGCCCAAGGACACCCTGATGATCAGCAGAAC CCCCGAGGTGACCTGCGTGGTGGTGGACGTGAGCCAG GAGGACCCCGAGGTGCAGTTCAACTGGTACGTGGACG GCGTGGAGGTGCACAACGCCAAGACCAAGCCCAGAG AGGAGCAGTTCAACAGCACCTACAGAGTGGTGAGCGT GCTGACCGTGCTGCACCAGGACTGGCTGAACGGCAAG GAGTACAAGTGCAAGGTGAGCAACAAGGGCCTGGGC AGCAGCATCGAGAAGACCATCAGCAAGGCCAAGGGC CAGCCCAGAGAGCCCCAGGTGTACACCCTGCCCCCCA GCCAGGAGGAGATGACCAAGAACCAGGTGAGCCTGA CCTGCCTGGTGAAGGGCTTCTACCCCAGCGACATCGC CGTGGAGTGGGAGAGCAACGGCCAGCCCGAGAACAA CTACAAGACCACCCCCCCCGTGCTGGACAGCGACGGC AGCTTCTTCCTGTACAGCAGACTGACCGTGGACAAGA GCAGATGGCAGGAGGGCAACGTGTTCAGCTGCAGCGT GATGCACGAGGCCCTGCACAACCACTACACCCAGAAG AGC |
| 85 | Nucleotide sequence encoding human IgG4 HC Constant domain (S228P D265A) | GCCAGCACCAAGGGCCCCAGCGTGTTCCCCCTGGCCC CCTGCAGCAGAAGCACCAGCGAGAGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AGCCTGGGCACCAAGACCTACACCTGCAACGTGGACC ACAAGCCCAGCAACACCAAGGTGGACAAGAGAGTGG AGAGCAAGTACGGCCCCCCCTGCCCCCCCTGCCCCGC CCCCGAGTTCCTGGGCGGCCCCAGCGTGTTCCTGTTCC CCCCCAAGCCCAAGGACACCCTGATGATCAGCAGAAC CCCCGAGGTGACCTGCGTGGTGGTGGCCGTGAGCCAG GAGGACCCCGAGGTGCAGTTCAACTGGTACGTGGACG GCGTGGAGGTGCACAACGCCAAGACCAAGCCCAGAG AGGAGCAGTTCAACAGCACCTACAGAGTGGTGAGCGT GCTGACCGTGCTGCACCAGGACTGGCTGAACGGCAAG GAGTACAAGTGCAAGGTGAGCAACAAGGGCCTGCCC AGCAGCATCGAGAAGACCATCAGCAAGGCCAAGGGC CAGCCCAGAGAGCCCCAGGTGTACACCCTGCCCCCCA GCCAGGAGGAGATGACCAAGAACCAGGTGAGCCTGA CCTGCCTGGTGAAGGGCTTCTACCCCAGCGACATCGC CGTGGAGTGGGAGAGCAACGGCCAGCCCGAGAACAA CTACAAGACCACCCCCCCCGTGCTGGACAGCGACGGC AGCTTCTTCCTGTACAGCAGACTGACCGTGGACAAGA GCAGATGGCAGGAGGGCAACGTGTTCAGCTGCAGCGT GATGCACGAGGCCCTGCACAACCACTACACCCAGAAG AGCCTGAGCCTGAGCCTGGGCAAG |
| 86 | Nucleotide sequence encoding human IgG4 HC Constant domain (S228P D265A N297G) | GCCAGCACCAAGGGCCCCAGCGTGTTCCCCCTGGCCC CCTGCAGCAGAAGCACCAGCGAGAGCACCGCCGCCCT GGGCTGCCTGGTGAAGGACTACTTCCCCGAGCCCGTG ACCGTGAGCTGGAACAGCGGCGCCCTGACCAGCGGCG TGCACACCTTCCCCGCCGTGCTGCAGAGCAGCGGCCT GTACAGCCTGAGCAGCGTGGTGACCGTGCCCAGCAGC AGCCTGGGCACCAAGACCTACACCTGCAACGTGGACC ACAAGCCCAGCAACACCAAGGTGGACAAGAGAGTGG AGAGCAAGTACGGCCCCCCCTGCCCCCCCTGCCCCGC CCCCGAGTTCCTGGGCGGCCCCAGCGTGTTCCTGTTCC CCCCCAAGCCCAAGGACACCCTGATGATCAGCAGAAC CCCCGAGGTGACCTGCGTGGTGGTGGCCGTGAGCCAG GAGGACCCCGAGGTGCAGTTCAACTGGTACGTGGACG GCGTGGAGGTGCACAACGCCAAGACCAAGCCCAGAG AGGAGCAGTTCGGCAGCACCTACAGAGTGGTGAGCGT |

TABLE OF SEQUENCES-continued

| SEQ ID NO: | Description | Sequence |
|---|---|---|
| | | GCTGACCGTGCTGCACCAGGACTGGCTGAACGGCAAG<br>GAGTACAAGTGCAAGGTGAGCAACAAGGGCCTGCCC<br>AGCAGCATCGAGAAGACCATCAGCAAGGCCAAGGGC<br>CAGCCCAGAGAGCCCCAGGTGTACACCCTGCCCCCA<br>GCCAGGAGGAGATGACCAAGAACCAGGTGAGCCTGA<br>CCTGCCTGGTGAAGGGCTTCTACCCCAGCGACATCGC<br>CGTGGAGTGGGAGAGCAACGGCCAGCCCGAGAACAA<br>CTACAAGACCACCCCCCCCGTGCTGGACAGCGACGGC<br>AGCTTCTTCCTGTACAGCAGACTGACCGTGGACAAGA<br>GCAGATGGCAGGAGGGCAACGTGTTCAGCTGCAGCGT<br>GATGCACGAGGCCCTGCACAACCACTACACCCAGAAG<br>AGCCTGAGCCTGAGCCTGGGCAAG |
| 87 | Nucleotide sequence encoding human IgG4 HC Constant domain (S228P N297X, wherein X is any amino acid other than N); codon 529-531 wherein N is any nucleotide with the proviso that the codon does not encode Asn or form a translation stop codon | GCCAGCACCAAGGGCCCCAGCGTGTTCCCCCTGGCCC<br>CCTGCAGCAGAAGCACCAGCGAGAGCACCGCCGCCCT<br>GGGCTGCCTGGTGAAGGACTACTTCCCCGAGCCCGTG<br>ACCGTGAGCTGGAACAGCGGCGCCCTGACCAGCGGCG<br>TGCACACCTTCCCCGCCGTGCTGCAGAGCAGCGGCCT<br>GTACAGCCTGAGCAGCGTGGTGACCGTGCCCAGCAGC<br>AGCCTGGGCACCAAGACCTACACCTGCAACGTGGACC<br>ACAAGCCCAGCAACACCAAGGTGGACAAGAGAGTGG<br>AGAGCAAGTACGGCCCCCCCTGCCCCCCCTGCCCCGC<br>CCCCGAGTTCCTGGGCGGCCCCAGCGTGTTCCTGTTCC<br>CCCCCAAGCCCAAGGACACCCTGATGATCAGCAGAAC<br>CCCCGAGGTGACCTGCGTGGTGGTGGACGTGAGCCAG<br>GAGGACCCCGAGGTGCAGTTCAACTGGTACGTGGACG<br>GCGTGGAGGTGCACAACGCCAAGACCAAGCCCAGAG<br>AGGAGCAGTTCNNNAGCACCTACAGAGTGGTGAGCGT<br>GCTGACCGTGCTGCACCAGGACTGGCTGAACGGCAAG<br>GAGTACAAGTGCAAGGTGAGCAACAAGGGCCTGCCC<br>AGCAGCATCGAGAAGACCATCAGCAAGGCCAAGGGC<br>CAGCCCAGAGAGCCCCAGGTGTACACCCTGCCCCCA<br>GCCAGGAGGAGATGACCAAGAACCAGGTGAGCCTGA<br>CCTGCCTGGTGAAGGGCTTCTACCCCAGCGACATCGC<br>CGTGGAGTGGGAGAGCAACGGCCAGCCCGAGAACAA<br>CTACAAGACCACCCCCCCCGTGCTGGACAGCGACGGC<br>AGCTTCTTCCTGTACAGCAGACTGACCGTGGACAAGA<br>GCAGATGGCAGGAGGGCAACGTGTTCAGCTGCAGCGT<br>GATGCACGAGGCCCTGCACAACCACTACACCCAGAAG<br>AGCCTGAGCCTGAGCCTGGGCAAG |
| 88 | Nucleotide sequence encoding human LC Kappa Constant domain | AGAACCGTGGCCGCCCCCAGCGTGTTCATCTTCCCCCC<br>CAGCGACGAGCAGCTGAAGAGCGGCACCGCCAGCGT<br>GGTGTGCCTGCTGAACAACTTCTACCCCAGAGAGGCC<br>AAGGTGCAGTGGAAGGTGGACAACGCCCTGCAGAGC<br>GGCAACAGCCAGGAGAGCGTGACCGAGCAGGACAGC<br>AAGGACAGCACCTACAGCCTGAGCAGCACCCTGACCC<br>TGAGCAAGGCCGACTACGAGAAGCACAAGGTGTACG<br>CCTGCGAGGTGACCCACCAGGGCCTGAGCAGCCCCGT<br>GACCAAGAGCTTCAACAGAGGCGAGTGC |
| 89 | Nucleotide sequence encoding human IgG1 HC Constant domain (N297A/D356E/L358M) | GCCAGCACCAAGGGCCCCAGCGTGTTCCCCCTGGCCC<br>CCAGCAGCAAGAGCACCAGCGGCGGCACCGCCGCCCT<br>GGGCTGCCTGGTGAAGGACTACTTCCCCGAGCCCGTG<br>ACCGTGAGCTGGAACAGCGGCGCCCTGACCAGCGGCG<br>TGCACACCTTCCCCGCCGTGCTGCAGAGCAGCGGCCT<br>GTACAGCCTGAGCAGCGTGGTGACCGTGCCCAGCAGC<br>AGCCTGGGCACCCAGACCTACATCTGCAACGTGAACC<br>ACAAGCCCAGCAACACCAAGGTGGACAAGAAGGTGG<br>AGCCCAAGAGCTGCGACAAGACCCACACCTGCCCCCC<br>CTGCCCCGCCCCCGAGCTGCTGGGCGGCCCCAGCGTG<br>TTCCTGTTCCCCCCCAAGCCCAAGGACACCCTGATGAT<br>CAGCAGAACCCCCGAGGTGACCTGCGTGGTGGTGGAC<br>GTGAGCCACGAGGACCCCGAGGTGAAGTTCAACTGGT<br>ACGTGGACGGCGTGGAGGTGCACAACGCCAAGACCA<br>AGCCCAGAGAGGAGCAGTACGCCAGCACCTACAGAG<br>TGGTGAGCGTGCTGACCGTGCTGCACCAGGACTGGCT<br>GAACGGCAAGGAGTACAAGTGCAAGGTGAGCAACAA<br>GGCCCTGCCCGCCCCCATCGAGAAGACCATCAGCAAG<br>GCCAAGGGCCAGCCCAGAGAGCCCCAGGTGTACACCC<br>TGCCCCCCAGCAGAGAGGAGATGACCAAGAACCAGG<br>TGAGCCTGACCTGCCTGGTGAAGGGCTTCTACCCCAG<br>CGACATCGCCGTGGAGTGGGAGAGCAACGGCCAGCCC<br>GAGAACAACTACAAGACCACCCCCCCCGTGCTGGACA<br>GCGACGGCAGCTTCTTCCTGTACAGCAAGCTGACCGT<br>GGACAAGAGCAGATGGCAGCAGGGCAACGTGTTCAG |

TABLE OF SEQUENCES-continued

| SEQ ID NO: | Description | Sequence |
|---|---|---|
| | | CTGCAGCGTGATGCACGAGGCCCTGCACAACCACTAC<br>ACCCAGAAGAGCCTGAGCCTGAGCCCCGGCAAG |
| 90 | Nucleotide sequence encoding human IgG1 HC Constant domain (L234F/L235E/P331S/ D356E/L358M) | GCCAGCACCAAGGGCCCCAGCGTGTTCCCCCTGGCCC<br>CCTGCAGCAGAAGCACCAGCGAGAGCACCGCCGCCCT<br>GGGCTGCCTGGTGAAGGACTACTTCCCCGAGCCCGTG<br>ACCGTGAGCTGGAACAGCGGCGCCCTGACCAGCGGCG<br>TGCACACCTTCCCCGCCGTGCTGCAGAGCAGCGGCCT<br>GTACAGCCTGAGCAGCGTGGTGACCGTGCCCAGCAGC<br>AGCCTGGGCACCAAGACCTACACCTGCAACGTGGACC<br>ACAAGCCCAGCAACACCAAGGTGGACAAGAGAGTGG<br>AGAGCAAGTACGGCCCCCCCTGCCCCCCCTGCCCCGC<br>CCCCGAGTTCCTGGGCGGCCCCAGCGTGTTCCTGTTCC<br>CCCCCAAGCCCAAGGACACCCTGATGATCAGCAGAAC<br>CCCCGAGGTGACCTGCGTGGTGGTGGACGTGAGCCAG<br>GAGGACCCCGAGGTGCAGTTCAACTGGTACGTGGACG<br>GCGTGGAGGTGCACAACGCCAAGACCAAGCCCAGAG<br>AGGAGCAGTTCAACAGCACCTACAGAGTGGTGAGCGT<br>GCTGACCGTGCTGCACCAGGACTGGCTGAACGGCAAG<br>GAGTACAAGTGCAAGGTGAGCAACAAGGGCCTGCCC<br>AGCAGCATCGAGAAGACCATCAGCAAGGCCAAGGGC<br>CAGCCCAGAGAGCCCCAGGTGTACACCCTGCCCCCCA<br>GCCTGACCTGCCTGGTGAAGGGCTTCTACCCCAGCGA<br>CATCGCCGTGGAGTGGGAGAGCAACGGCCAGCCCGA<br>GAACAACTACAAGACCACCCCCCCCGTGCTGGACAGC<br>GACGGCAGCTTCTTCCTGTACAGCAGACTGACCGTGG<br>ACAAGAGCAGATGGCAGGAGGGCAACGTGTTCAGCT<br>GCAGCGTGATGCACGAGGCCCTGCACAACCACTACAC<br>CCAGAAGAGCCTGAGCCTGAGCCTGGGCAAG |
| 91 | Nucleotide sequence encoding human LC lambda Constant domain | GGCCAGCCCAAGGCCAACCCCACCGTGACCCTGTTCC<br>CCCCCAGCAGCGAGGAGCTGCAGGCCAACAAGGCCA<br>CCCTGGTGTGCCTGATCAGCGACTTCTACCCCGGCGCC<br>GTGACCGTGGCCTGGAAGGCCGACGGCAGCCCCGTGA<br>AGGCCGGCGTGGAGACCACCAAGCCCAGCAAGCAGA<br>GCAACAACAAGTACGCCGCCAGCAGCTACCTGAGCCT<br>GACCCCCGAGCAGTGGAAGAGCCACAGAAGCTACAG<br>CTGCCAGGTGACCCACGAGGGCAGCACCGTGGAGAA<br>GACCGTGGCCCCCACCGAGTGCAGC |
| 92 | Nucleotide sequence encoding mouse HC IgG1 (D265A) constant domain | GCCAAGACCACCCCCCCCAGCGTGTACCCCCTGGCCC<br>CCGGCAGCGCCGCCCAGACCAACAGCATGGTGACCCT<br>GGGCTGCCTGGTGAAGGGCTACTTCCCCGAGCCCGTG<br>ACCGTGACCTGGAACAGCGGCAGCCTGAGCAGCGGCG<br>TGCACACCTTCCCCGCCGTGCTGCAGAGCGACCTGTA<br>CACCCTGAGCAGCAGCGTGACCGTGCCCAGCAGCACC<br>TGGCCCAGCGAGACCGTGACCTGCAACGTGGCCCACC<br>CCGCCAGCAGCACCAAGGTGGACAAGAAGATCGTGCC<br>CAGAGACTGCGGCTGCAAGCCCTGCATCTGCACCGTG<br>CCCGAGGTGAGCAGCGTGTTCATCTTCCCCCCCAAGC<br>CCAAGGACGTGCTGACCATCACCCTGACCCCCAAGGT<br>GACCTGCGTGGTGGTGGCCATCAGCAAGGACGACCCC<br>GAGGTGCAGTTCAGCTGGTTCGTGGACGACGTGGAGG<br>TGCACACCGCCCAGACCCAGCCCAGAGAGGAGCAGTT<br>CAACAGCACCTTCAGAAGCGTGAGCGAGCTGCCCATC<br>ATGCACCAGGACTGGCTGAACGGCAAGGAGTTCAAGT<br>GCAGAGTGAACAGCGCCGCCTTCCCCGCCCCCATCGA<br>GAAGACCATCAGCAAGACCAAGGGCAGACCCAAGGC<br>CCCCCAGGTGTACACCATCCCCCCCCCCAAGGAGCAG<br>ATGGCCAAGGACAAGGTGAGCCTGACCTGCATGATCA<br>CCGACTTCTTCCCCGAGGACATCACCGTGGAGTGGCA<br>GTGGAACGGCCAGCCCGCCGAGAACTACAAGAACAC<br>CCAGCCCATCATGGACACCGACGGCAGCTACTTCGTG<br>TACAGCAAGCTGAACGTGCAGAAGAGCAACTGGGAG<br>GCCGGCAACACCTTCACCTGCAGCGTGCTGCACGAGG<br>GCCTGCACAACCACCACACCGAGAAGAGCCTGAGCCA<br>CAGCCCCGGCAAG |
| 93 | Nucleotide sequence encoding mouse HC IgG2 constant domain | GCCAAGACCACCGCCCCCAGCGTGTACCCCCTGGCCC<br>CCGTGTGCGGCGACACCACCGGCAGCAGCGTGACCCT<br>GGGCTGCCTGGTGAAGGGCTACTTCCCCGAGCCCGTG<br>ACCCTGACCTGGAACAGCGGCAGCCTGAGCAGCGGCG<br>TGCACACCTTCCCCGCCGTGCTGCAGAGCGACCTGTA<br>CACCCTGAGCAGCAGCGTGACCGTGACCAGCAGCACC<br>TGGCCCAGCCAGAGCATCACCTGCAACGTGGCCCACC<br>CCGCCAGCAGCACCAAGGTGGACAAGAAGATCGAGC |

TABLE OF SEQUENCES-continued

| SEQ ID NO: | Description | Sequence |
|---|---|---|
| | | CCAGAGGCCCCACCATCAAGCCCTGCCCCCCCTGCAA GTGCCCCGCCCCCAACCTGCTGGGCGGCCCCAGCGTG TTCATCTTCCCCCCCAAGATCAAGGACGTGCTGATGAT CAGCCTGAGCCCCATCGTGACCTGCGTGGTGGTGGAC GTGAGCGAGGACGACCCCGACGTGCAGATCAGCTGGT TCGTGAACAACGTGGAGGTGCACACCGCCCAGACCCA GACCCACAGAGAGGACTACAACAGCACCCTGAGAGT GGTGAGCGCCCTGCCCATCCAGCACCAGGACTGGATG AGCGGCAAGGAGTTCAAGTGCAAGGTGAACAACAAG GACCTGCCCGCCCCCATCGAGAGAACCATCAGCAAGC CCAAGGGCAGCGTGAGAGCCCCCCAGGTGTACGTGCT GCCCCCCCCCGAGGAGGAGATGACCAAGAAGCAGGT GACCCTGACCTGCATGGTGACCGACTTCATGCCCGAG GACATCTACGTGGAGTGGACCAACAACGGCAAGACCG AGCTGAACTACAAGAACACCGAGCCCGTGCTGGACAG CGACGGCAGCTACTTCATGTACAGCAAGCTGAGAGTG GAGAAGAAGAACTGGGTGGAGAGAAACAGCTACAGC TGCAGCGTGGTGCACGAGGGCCTGCACAACCACCACA CCACCAAGAGCTTCAGCAGAACCCCCGGCAAG |
| 94 | Nucleotide sequence encoding mouse LC kappa constant domain | AGAACCGTGGCCGCCCCCACCGTGAGCATCTTCCCCC CCAGCAGCGAGCAGCTGACCAGCGGCGGCGCCAGCG TGGTGTGCTTCCTGAACAACTTCTACCCCAAGGACATC AACGTGAAGTGGAAGATCGACGGCAGCGAGAGACAG AACGGCGTGCTGAACAGCTGGACCGACCAGGACAGC AAGGACAGCACCTACAGCATGAGCAGCACCCTGACCC TGACCAAGGACGAGTACGAGAGACACAACAGCTACA CCTGCGAGGCCACCCACAAGACCAGCACCAGCCCCAT CGTGAAGAGCTTCAACAGAAACGAGTGC |
| 95 | Leader peptide A | MSVPTQVLGLLLLWLTDARC |
| 96 | Leader peptide B | MEWSWVFLFFLSVTTGVHS |
| 97 | Nucleotide sequence encoding leader peptide A | ATGAGCGTGCCCACCCAGGTGCTGGGCCTGCTGCTGC TGTGGCTGACCGACGCCAGATGC |
| 98 | Nucleotide sequence encoding leader peptide B | ATGGAGTGGAGCTGGGTGTTCCTGTTCTTCCTGAGCGT GACCACCGGCGTGCACAGC |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. An Arginase 1 binder comprising:

(a) three complementarity determining regions (CDRs) of an antibody heavy chain variable domain (VH) comprising the amino acid sequence set forth for VH1 in SEQ ID NO: 2 or an antibody VH comprising the amino acid sequence set forth for VH2 in SEQ ID NO: 3; and (b) the three CDRs of an antibody light chain variable domain (VL) comprising the amino acid sequence set forth in SEQ ID NO: 4.

2. The Arginase 1 binder of claim 1, wherein the Arginase 1 binder specifically binds to two arginase 1 trimers to form a complex comprising three Arginase 1 binders and two arginase trimers, and inhibits arginase 1 activity.

3. The Arginase 1 binder of claim 1, wherein (a) the VH CDRs comprise a VH1-CDR1 comprising the amino acid sequence set forth in SEQ ID NO: 5, a VH1-CDR2 comprising the amino acid sequence set forth in SEQ ID NO: 6, and a VH1-CDR3 comprising the amino acid sequence set forth in SEQ ID NO: 7, and (b) the VL CDRs comprise a VL-CDR1 comprising the amino acid sequence set forth in SEQ ID NO: 31, a VL-CDR2 comprising the amino acid sequence set forth in SEQ ID NO: 32, and a VL-CDR3 comprising the amino acid sequence set forth in SEQ ID NO: 33; or (a) the VH CDRs comprise a VH2-CDR1 comprising the amino acid sequence set forth in SEQ ID NO: 18, a VH2-CDR2 comprising the amino acid sequence set forth in SEQ ID NO: 19, and a VH2-CDR3 comprising the amino acid sequence set forth in SEQ ID NO: 20; and (b) the VL CDRs comprise a VL-CDR1 comprising the amino acid sequence set forth in SEQ ID NO: 31, a VL-CDR2 comprising the amino acid sequence set forth in SEQ ID NO: 32, and a VL-CDR3 comprising the amino acid sequence set forth in SEQ ID NO: 33;

wherein the CDR sequences are defined by Kabat.

4. The Arginase 1 binder of claim 1, wherein the Arginase 1 binder comprises an antibody or antigen-binding fragment VH1 comprising the amino acid sequence set forth in SEQ ID NO: 2 and a VL1 comprising the amino acid sequence set forth in SEQ ID NO: 4.

5. The Arginase 1 binder of claim 1, wherein the Arginase 1 binder comprises an antibody or antigen-binding fragment VH2 comprising the amino acid sequence set forth in SEQ ID NO: 3 and a VL comprising the amino acid sequence set forth in SEQ ID NO: 4.

6. The Arginase 1 binder of claim 1, wherein the antibody further comprises a heavy chain constant domain of the IgG1, IgG2, IgG3, or IgG4 isotype.

7. The Arginase 1 binder of claim 6, wherein the heavy chain constant domain of the IgG1, IgG2, IgG3, or IgG4 isotype comprises an effector-silent Fc domain.

8. A composition comprising an Arginase 1 binder of claim 1 and a pharmaceutically acceptable carrier.

9. A method for treating cancer or proliferative disease in an individual in need thereof comprising:

administering to the individual a therapeutically effective amount an Arginase 1 binder of claim 1 to treat the cancer or a proliferative disease.

10. An arginase 1 binder of claim 1 for treatment of cancer or proliferative disease.

11. A combination therapy for treating cancer or proliferative disease comprising an arginase 1 binder of claim 1 and a therapeutic agent.

12. The combination therapy of claim 11, wherein the therapeutic agent is a chemotherapy agent or a therapeutic antibody.

13. The combination therapy of claim 12, wherein the antibody is an anti-PD1 or anti-PD-L1 antibody.

14. A nucleic acid molecule encoding the VH and VL of the Arginase 1 binder of claim 1.

15. An expression vector comprising one or more of the nucleic acid molecules of claim 14.

16. A host cell comprising the expression vector of claim 15.

17. A method for producing an Arginase 1 binder comprising:

(a) providing the host cell of claim 16;

(b) cultivating the host cell in a medium under conditions suitable for expressing the Arginase 1 binder; and (c) isolating the Arginase 1 binder from the medium.

* * * * *

SEQUENCE LISTING

```
<160> NUMBER OF SEQ ID NOS: 98

<210> SEQ ID NO 1
<211> LENGTH: 322
<212> TYPE: PRT
<213> ORGANISM: Homo Sapiens

<400> SEQUENCE: 1

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45
```

-continued

```
Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
    290                 295                 300

Gly Leu Ala Arg Glu Gly Asn His Lys Pro Ile Asp Tyr Leu Asn Pro
305                 310                 315                 320

Pro Lys


<210> SEQ ID NO 2
<211> LENGTH: 125
<212> TYPE: PRT
<213> ORGANISM: Artificial Sequence
<220> FEATURE:
<223> OTHER INFORMATION: VH1 (parent)

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85                  90                  95

Ala Arg Glu Gly Ala Tyr Gly Tyr Arg Ser Pro Tyr His Asn Trp Phe
            100                 105                 110

Asp Pro Trp Gly Gln Gly Thr Leu Val Thr Val Ser Ser
        115                 120                 125


<210> SEQ ID NO 3
<211> LENGTH: 125
<212> TYPE: PRT
<213> ORGANISM: Artificial Sequence
<220> FEATURE:
<223> OTHER INFORMATION: VH2 (affinity matured)

<400> SEQUENCE: 3

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Phe Lys Tyr
            20                  25                  30

Gly Ile Ser Trp Val Arg Gln Ala Pro Gly Gln Gly Leu Glu Trp Met
        35                  40                  45

Gly Ser Ile Ser Pro Tyr Thr Gly Glu Thr His Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Gly Ala Tyr Gly Tyr Arg Ser Pro Tyr Gln Asn Trp Phe
            100                 105                 110

Asp Pro Trp Gly Gln Gly Thr Leu Val Thr Val Ser Ser
        115                 120                 125


<210> SEQ ID NO 4
<211> LENGTH: 107
<212> TYPE: PRT
<213> ORGANISM: Artificial Sequence
<220> FEATURE:
<223> OTHER INFORMATION: VL

<400> SEQUENCE: 4

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln His Ser Leu Leu Pro Arg
                85                  90                  95

Thr Phe Gly Gly Gly Thr Lys Val Glu Ile Lys
            100                 105


<210> SEQ ID NO 5
<211> LENGTH: 5
<212> TYPE: PRT
```

<213> ORGANISM: Artificial Sequence
<220> FEATURE:
<223> OTHER INFORMATION: VH1-CDR1 Kabat

<400> SEQUENCE: 5

Asn Tyr Gly Ile Ser
1 5

<210> SEQ ID NO 6
<211> LENGTH: 17
<212> TYPE: PRT
<213> ORGANISM: Artificial Sequence
<220> FEATURE:
<223> OTHER INFORMATION: VH1-CDR2 Kabat/Kabat+Chothia

<400> SEQUENCE: 6

Trp Ile Ser Ala Tyr Asn Gly Asn Thr Asn Tyr Ala Gln Lys Leu Gln
1 5 10 15

Gly

<210> SEQ ID NO 7
<211> LENGTH: 16
<212> TYPE: PRT
<213> ORGANISM: Artificial Sequence
<220> FEATURE:
<223> OTHER INFORMATION: VH1-CDR3 Kabat/Chothia/Kabat+Chothia/AbM

<400> SEQUENCE: 7

Glu Gly Ala Tyr Gly Tyr Arg Ser Pro Tyr His Asn Trp Phe Asp Pro
1 5 10 15

<210> SEQ ID NO 8
<211> LENGTH: 7
<212> TYPE: PRT
<213> ORGANISM: Artificial Sequence
<220> FEATURE:
<223> OTHER INFORMATION: VH1-CDR1 Chothia

<400> SEQUENCE: 8

Gly Tyr Thr Phe Thr Asn Tyr
1 5

<210> SEQ ID NO 9
<211> LENGTH: 6
<212> TYPE: PRT
<213> ORGANISM: Artificial Sequence
<220> FEATURE:
<223> OTHER INFORMATION: VH1-CDR2 Chothia

<400> SEQUENCE: 9

Ser Ala Tyr Asn Gly Asn
1 5

<210> SEQ ID NO 10
<211> LENGTH: 10
<212> TYPE: PRT
<213> ORGANISM: Artificial Sequence
<220> FEATURE:
<223> OTHER INFORMATION: VH1-CDR1 Kabat+Chothia/AbM

<400> SEQUENCE: 10

Gly Tyr Thr Phe Thr Asn Tyr Gly Ile Ser
1 5 10

<210> SEQ ID NO 11
<211> LENGTH: 10

```
<212> TYPE: PRT
<213> ORGANISM: Artificial Sequence
<220> FEATURE:
<223> OTHER INFORMATION: VH1-CDR2 AbM

<400> SEQUENCE: 11

Trp Ile Ser Ala Tyr Asn Gly Asn Thr Asn
1               5                   10


<210> SEQ ID NO 12
<211> LENGTH: 8
<212> TYPE: PRT
<213> ORGANISM: Artificial Sequence
<220> FEATURE:
<223> OTHER INFORMATION: VH1-CDR1 IMGT

<400> SEQUENCE: 12

Gly Tyr Thr Phe Thr Asn Tyr Gly
1               5


<210> SEQ ID NO 13
<211> LENGTH: 7
<212> TYPE: PRT
<213> ORGANISM: Artificial Sequence
<220> FEATURE:
<223> OTHER INFORMATION: VH1-CDR2 IMGT

<400> SEQUENCE: 13

Ile Ser Ala Tyr Asn Gly Asn
1               5


<210> SEQ ID NO 14
<211> LENGTH: 18
<212> TYPE: PRT
<213> ORGANISM: Artificial Sequence
<220> FEATURE:
<223> OTHER INFORMATION: VH1-CDR3 IMGT

<400> SEQUENCE: 14

Ala Arg Glu Gly Ala Tyr Gly Tyr Arg Ser Pro Tyr His Asn Trp Phe
1               5                   10                  15

Asp Pro


<210> SEQ ID NO 15
<211> LENGTH: 6
<212> TYPE: PRT
<213> ORGANISM: Artificial Sequence
<220> FEATURE:
<223> OTHER INFORMATION: VH1-CDR1 Contact

<400> SEQUENCE: 15

Thr Asn Tyr Gly Ile Ser
1               5


<210> SEQ ID NO 16
<211> LENGTH: 13
<212> TYPE: PRT
<213> ORGANISM: Artificial Sequence
<220> FEATURE:
<223> OTHER INFORMATION: VH1-CDR2 Contact

<400> SEQUENCE: 16

Trp Met Gly Trp Ile Ser Ala Tyr Asn Gly Asn Thr Asn
1               5                   10


<210> SEQ ID NO 17
```

<211> LENGTH: 17
<212> TYPE: PRT
<213> ORGANISM: Artificial Sequence
<220> FEATURE:
<223> OTHER INFORMATION: VH1-CDR3 Contact

<400> SEQUENCE: 17

Ala Arg Glu Gly Ala Tyr Gly Tyr Arg Ser Pro Tyr His Asn Trp Phe
1 5 10 15

Asp

<210> SEQ ID NO 18
<211> LENGTH: 5
<212> TYPE: PRT
<213> ORGANISM: Artificial Sequence
<220> FEATURE:
<223> OTHER INFORMATION: VH2-CDR1 Kabat

<400> SEQUENCE: 18

Lys Tyr Gly Ile Ser
1 5

<210> SEQ ID NO 19
<211> LENGTH: 17
<212> TYPE: PRT
<213> ORGANISM: Artificial Sequence
<220> FEATURE:
<223> OTHER INFORMATION: VH2-CDR2 Kabat/Kabat+Chothia

<400> SEQUENCE: 19

Ser Ile Ser Pro Tyr Thr Gly Glu Thr His Tyr Ala Gln Lys Leu Gln
1 5 10 15

Gly

<210> SEQ ID NO 20
<211> LENGTH: 16
<212> TYPE: PRT
<213> ORGANISM: Artificial Sequence
<220> FEATURE:
<223> OTHER INFORMATION: VH2-CDR3 Kabat/Chothia/Kabat+Chothia/AbM

<400> SEQUENCE: 20

Glu Gly Ala Tyr Gly Tyr Arg Ser Pro Tyr Gln Asn Trp Phe Asp Pro
1 5 10 15

<210> SEQ ID NO 21
<211> LENGTH: 7
<212> TYPE: PRT
<213> ORGANISM: Artificial Sequence
<220> FEATURE:
<223> OTHER INFORMATION: VH2-CDR1 Chothia

<400> SEQUENCE: 21

Gly Tyr Thr Phe Phe Lys Tyr
1 5

<210> SEQ ID NO 22
<211> LENGTH: 6
<212> TYPE: PRT
<213> ORGANISM: Artificial Sequence
<220> FEATURE:
<223> OTHER INFORMATION: VH2-CDR2 Chothia

<400> SEQUENCE: 22

Ser Pro Tyr Thr Gly Glu
1 5

<210> SEQ ID NO 23
<211> LENGTH: 10
<212> TYPE: PRT
<213> ORGANISM: Artificial Sequence
<220> FEATURE:
<223> OTHER INFORMATION: VH2-CDR1 Kabat+Chothia/AbM

<400> SEQUENCE: 23

Gly Tyr Thr Phe Phe Lys Tyr Gly Ile Ser
1               5                   10

<210> SEQ ID NO 24
<211> LENGTH: 10
<212> TYPE: PRT
<213> ORGANISM: Artificial Sequence
<220> FEATURE:
<223> OTHER INFORMATION: VH2-CDR2 AbM

<400> SEQUENCE: 24

Ser Ile Ser Pro Tyr Thr Gly Glu Thr Asn
1               5                   10

<210> SEQ ID NO 25
<211> LENGTH: 8
<212> TYPE: PRT
<213> ORGANISM: Artificial Sequence
<220> FEATURE:
<223> OTHER INFORMATION: VH2-CDR1 IMGT

<400> SEQUENCE: 25

Gly Tyr Thr Phe Lys Asn Tyr Gly
1               5

<210> SEQ ID NO 26
<211> LENGTH: 7
<212> TYPE: PRT
<213> ORGANISM: Artificial Sequence
<220> FEATURE:
<223> OTHER INFORMATION: VH2-CDR2 IMGT

<400> SEQUENCE: 26

Ile Ser Pro Tyr Thr Gly Glu
1               5

<210> SEQ ID NO 27
<211> LENGTH: 18
<212> TYPE: PRT
<213> ORGANISM: Artificial Sequence
<220> FEATURE:
<223> OTHER INFORMATION: VH2-CDR3 IMGT

<400> SEQUENCE: 27

Ala Arg Glu Gly Ala Tyr Gly Tyr Arg Ser Pro Tyr Gln Asn Trp Phe
1               5                   10                  15

Asp Pro

<210> SEQ ID NO 28
<211> LENGTH: 6
<212> TYPE: PRT
<213> ORGANISM: Artificial Sequence
<220> FEATURE:
<223> OTHER INFORMATION: VH2-CDR1Contact

<400> SEQUENCE: 28

Phe Lys Tyr Gly Ile Ser
1 5

<210> SEQ ID NO 29
<211> LENGTH: 13
<212> TYPE: PRT
<213> ORGANISM: Artificial Sequence
<220> FEATURE:
<223> OTHER INFORMATION: VH2-CDR2 Contact

<400> SEQUENCE: 29

Trp Met Gly Ser Ile Ser Pro Tyr Thr Gly Glu Thr Asn
1 5 10

<210> SEQ ID NO 30
<211> LENGTH: 17
<212> TYPE: PRT
<213> ORGANISM: Artificial Sequence
<220> FEATURE:
<223> OTHER INFORMATION: VH2-CDR3 Contact

<400> SEQUENCE: 30

Ala Arg Glu Gly Ala Tyr Gly Tyr Arg Ser Pro Tyr Gln Asn Trp Phe
1 5 10 15

Asp

<210> SEQ ID NO 31
<211> LENGTH: 11
<212> TYPE: PRT
<213> ORGANISM: Artificial Sequence
<220> FEATURE:
<223> OTHER INFORMATION: VL-CDR1 Kabat/Chothia/Kabat+Chothia/AbM

<400> SEQUENCE: 31

Arg Ala Ser Gln Ser Val Ser Ser Tyr Leu Ala
1 5 10

<210> SEQ ID NO 32
<211> LENGTH: 7
<212> TYPE: PRT
<213> ORGANISM: Artificial Sequence
<220> FEATURE:
<223> OTHER INFORMATION: VL-CDR2 Kabat/Chothia/Kabat+Chothia/AbM

<400> SEQUENCE: 32

Asp Ala Ser Asn Arg Ala Thr
1 5

<210> SEQ ID NO 33
<211> LENGTH: 9
<212> TYPE: PRT
<213> ORGANISM: Artificial Sequence
<220> FEATURE:
<223> OTHER INFORMATION: VL-CDR3 Kabat/Chothia/Kabat+Chothia/AbM/IMGT

<400> SEQUENCE: 33

Gln Gln His Ser Leu Leu Pro Arg Thr
1 5

<210> SEQ ID NO 34
<211> LENGTH: 8
<212> TYPE: PRT
<213> ORGANISM: Artificial Sequence
<220> FEATURE:

<223> OTHER INFORMATION: VL-CDR1 IMGT

<400> SEQUENCE: 34

```
Gln Ser Val Ser Ser Tyr Leu Ala
1               5
```

<210> SEQ ID NO 35
<211> LENGTH: 7
<212> TYPE: PRT
<213> ORGANISM: Artificial Sequence
<220> FEATURE:
<223> OTHER INFORMATION: VL-CDR1 Contact

<400> SEQUENCE: 35

```
Ser Ser Tyr Leu Ala Trp Tyr
1               5
```

<210> SEQ ID NO 36
<211> LENGTH: 10
<212> TYPE: PRT
<213> ORGANISM: Artificial Sequence
<220> FEATURE:
<223> OTHER INFORMATION: VL-CDR2 Contact

<400> SEQUENCE: 36

```
Leu Leu Ile Tyr Asp Ala Ser Asn Arg Ala
1               5                   10
```

<210> SEQ ID NO 37
<211> LENGTH: 8
<212> TYPE: PRT
<213> ORGANISM: Artificial Sequence
<220> FEATURE:
<223> OTHER INFORMATION: VL-CDR3 Contact

<400> SEQUENCE: 37

```
Gln Gln His Ser Leu Leu Pro Arg
1               5
```

<210> SEQ ID NO 38
<211> LENGTH: 330
<212> TYPE: PRT
<213> ORGANISM: Artificial Sequence
<220> FEATURE:
<223> OTHER INFORMATION: Human IgG1 HC constant domain

<400> SEQUENCE: 38

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 39
<211> LENGTH: 330
<212> TYPE: PRT
<213> ORGANISM: Artificial Sequence
<220> FEATURE:
<223> OTHER INFORMATION: Human IgG1 HC Constant domain (L234A L235A
      D265S)

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 40
<211> LENGTH: 330
<212> TYPE: PRT
<213> ORGANISM: Artificial Sequence
<220> FEATURE:
<223> OTHER INFORMATION: Human IgG1 HC Constant domain (L234A L235A P329G)

<400> SEQUENCE: 40

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ser Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 41
<211> LENGTH: 330
<212> TYPE: PRT
<213> ORGANISM: Artificial Sequence
<220> FEATURE:
<223> OTHER INFORMATION: Human IgG1 HC Constant domain (L235E)

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 42
<211> LENGTH: 330
<212> TYPE: PRT
<213> ORGANISM: Artificial Sequence
<220> FEATURE:
<223> OTHER INFORMATION: Human IgG1 HC Constant domain (D265A)

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 43
<211> LENGTH: 330
<212> TYPE: PRT
<213> ORGANISM: Artificial Sequence
<220> FEATURE:
<223> OTHER INFORMATION: Human IgG1 HC Constant domain (D265A N297G)

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 44
<211> LENGTH: 330
<212> TYPE: PRT
<213> ORGANISM: Artificial Sequence
<220> FEATURE:
<223> OTHER INFORMATION: Human IgG1 HC Constant domain (E233A/L235A)

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Ala Leu Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

-continued

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 45
<211> LENGTH: 330
<212> TYPE: PRT
<213> ORGANISM: Artificial Sequence
<220> FEATURE:
<223> OTHER INFORMATION: Human IgG1 HC Constant domain (N297X
<220> FEATURE:
<221> NAME/KEY: MISC_FEATURE
<222> LOCATION: (180)..(180)
<223> OTHER INFORMATION: Xaa is any amino acid other than Asn

<400> SEQUENCE: 45

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Xaa Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 46
<211> LENGTH: 326
<212> TYPE: PRT
<213> ORGANISM: Artificial Sequence
<220> FEATURE:
<223> OTHER INFORMATION: Human IgG2 HC Constant domain

<400> SEQUENCE: 46

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320
```

Ser Leu Ser Pro Gly Lys
325

<210> SEQ ID NO 47
<211> LENGTH: 326
<212> TYPE: PRT
<213> ORGANISM: Artificial Sequence
<220> FEATURE:
<223> OTHER INFORMATION: Human IgG2 HC Constant domain (D265S)

<400> SEQUENCE: 47

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val Glu Arg Lys Cys Cys Val Glu Cys Pro Pro Cys Pro Ala Pro
100 105 110

Pro Val Ala Gly Pro Ser Val Phe Leu Phe Pro Pro Lys Pro Lys Asp
115 120 125

Thr Leu Met Ile Ser Arg Thr Pro Glu Val Thr Cys Val Val Val Ser
130 135 140

Val Ser His Glu Asp Pro Glu Val Gln Phe Asn Trp Tyr Val Asp Gly
145 150 155 160

Val Glu Val His Asn Ala Lys Thr Lys Pro Arg Glu Glu Gln Phe Asn
165 170 175

Ser Thr Phe Arg Val Val Ser Val Leu Thr Val Val His Gln Asp Trp
180 185 190

Leu Asn Gly Lys Glu Tyr Lys Cys Lys Val Ser Asn Lys Gly Leu Pro
195 200 205

Ala Pro Ile Glu Lys Thr Ile Ser Lys Thr Lys Gly Gln Pro Arg Glu
210 215 220

Pro Gln Val Tyr Thr Leu Pro Pro Ser Arg Glu Glu Met Thr Lys Asn
225 230 235 240

Gln Val Ser Leu Thr Cys Leu Val Lys Gly Phe Tyr Pro Ser Asp Ile
245 250 255

Ser Val Glu Trp Glu Ser Asn Gly Gln Pro Glu Asn Asn Tyr Lys Thr
260 265 270

Thr Pro Pro Met Leu Asp Ser Asp Gly Ser Phe Phe Leu Tyr Ser Lys
275 280 285

Leu Thr Val Asp Lys Ser Arg Trp Gln Gln Gly Asn Val Phe Ser Cys
290 295 300

Ser Val Met His Glu Ala Leu His Asn His Tyr Thr Gln Lys Ser Leu
305 310 315 320

Ser Leu Ser Pro Gly Lys
325

<210> SEQ ID NO 48

```
<211> LENGTH: 326
<212> TYPE: PRT
<213> ORGANISM: Artificial Sequence
<220> FEATURE:
<223> OTHER INFORMATION: Human IgG2 HC Constant domain (P329G)

<400> SEQUENCE: 48

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Gly
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 49
<211> LENGTH: 326
<212> TYPE: PRT
<213> ORGANISM: Artificial Sequence
<220> FEATURE:
<223> OTHER INFORMATION: Human IgG2 HC Constant domain (D265A)
```

<400> SEQUENCE: 49

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Ala
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 50
<211> LENGTH: 326
<212> TYPE: PRT
<213> ORGANISM: Artificial Sequence
<220> FEATURE:
<223> OTHER INFORMATION: Human IgG2 HC Constant domain (D265A N297G)

<400> SEQUENCE: 50

Ala Ser Thr Lys Gly Pro Ser Val Phe Pro Leu Ala Pro Cys Ser Arg
1               5                   10                  15

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Ala
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Gly
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 51
<211> LENGTH: 326
<212> TYPE: PRT
<213> ORGANISM: Artificial Sequence
<220> FEATURE:
<223> OTHER INFORMATION: Human IgG2 HC Constant domain (N297X)
<220> FEATURE:
<221> NAME/KEY: MISC_FEATURE
<222> LOCATION: (176)..(176)
<223> OTHER INFORMATION: Xaa is any amino acid other than Asn

<400> SEQUENCE: 51

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Xaa
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 52
<211> LENGTH: 326
<212> TYPE: PRT
<213> ORGANISM: Artificial Sequence
<220> FEATURE:
<223> OTHER INFORMATION: Human IgG2 HC Constant domain (V234A G237A
      P238S H268A V309L A330S P331S X378S/A)
<220> FEATURE:
<221> NAME/KEY: misc_feature
<222> LOCATION: (257)..(257)
<223> OTHER INFORMATION: Xaa can be any naturally occurring amino acid

<400> SEQUENCE: 52

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Ser Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Ala Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Xaa Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 53
<211> LENGTH: 327
<212> TYPE: PRT
<213> ORGANISM: Artificial Sequence
<220> FEATURE:
<223> OTHER INFORMATION: Human IgG4 HC Constant domain (S228P)

<400> SEQUENCE: 53

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 54
<211> LENGTH: 327
<212> TYPE: PRT
<213> ORGANISM: Artificial Sequence
<220> FEATURE:
<223> OTHER INFORMATION: Human IgG4 HC Constant domain (S228P P329G)

<400> SEQUENCE: 54

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

```
Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Gly Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 55
<211> LENGTH: 327
<212> TYPE: PRT
<213> ORGANISM: Artificial Sequence
<220> FEATURE:
<223> OTHER INFORMATION: Human IgG4 HC Constant domain (S228P D265A)

<400> SEQUENCE: 55

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110
```

```
Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 56
<211> LENGTH: 327
<212> TYPE: PRT
<213> ORGANISM: Artificial Sequence
<220> FEATURE:
<223> OTHER INFORMATION: Human IgG4 HC Constant domain (S228P D265A
      N297G)

<400> SEQUENCE: 56

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

```
Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Gly Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 57
<211> LENGTH: 327
<212> TYPE: PRT
<213> ORGANISM: Artificial Sequence
<220> FEATURE:
<223> OTHER INFORMATION: Human IgG4 HC Constant domain (S228P N297X)
<220> FEATURE:
<221> NAME/KEY: MISC_FEATURE
<222> LOCATION: (177)..(177)
<223> OTHER INFORMATION: Xaa is any amino acid other than Asn

<400> SEQUENCE: 57

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Xaa Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 58
<211> LENGTH: 107
<212> TYPE: PRT
<213> ORGANISM: Artificial Sequence
<220> FEATURE:
<223> OTHER INFORMATION: Human LC Kappa Constant domain

<400> SEQUENCE: 58

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 59
<211> LENGTH: 330
<212> TYPE: PRT
<213> ORGANISM: Artificial Sequence
<220> FEATURE:
<223> OTHER INFORMATION: Human IgG1 HC Constant domain
      (N297A/D356E/L358M)
```

-continued

<400> SEQUENCE: 59

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 60
<211> LENGTH: 317
<212> TYPE: PRT
<213> ORGANISM: Artificial Sequence
<220> FEATURE:
<223> OTHER INFORMATION: Human IgG1 HC Constant domain
      (L234F/L235E/P331S/D356E/L358M)

<400> SEQUENCE: 60

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Pro Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Leu Thr Cys Leu Val Lys
225 230 235 240

Gly Phe Tyr Pro Ser Asp Ile Ala Val Glu Trp Glu Ser Asn Gly Gln
245 250 255

Pro Glu Asn Asn Tyr Lys Thr Thr Pro Pro Val Leu Asp Ser Asp Gly
260 265 270

Ser Phe Phe Leu Tyr Ser Arg Leu Thr Val Asp Lys Ser Arg Trp Gln
275 280 285

Glu Gly Asn Val Phe Ser Cys Ser Val Met His Glu Ala Leu His Asn
290 295 300

His Tyr Thr Gln Lys Ser Leu Ser Leu Ser Leu Gly Lys
305 310 315

<210> SEQ ID NO 61
<211> LENGTH: 106
<212> TYPE: PRT
<213> ORGANISM: Artificial Sequence
<220> FEATURE:
<223> OTHER INFORMATION: Human LC lambda Constant domain

<400> SEQUENCE: 61

Gly Gln Pro Lys Ala Asn Pro Thr Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Gly Ser Pro
35 40 45

Val Lys Ala Gly Val Glu Thr Thr Lys Pro Ser Lys Gln Ser Asn Asn
50 55 60

```
Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 62
<211> LENGTH: 324
<212> TYPE: PRT
<213> ORGANISM: Artificial Sequence
<220> FEATURE:
<223> OTHER INFORMATION: Mouse HC IgG1 (D265A) constant domain

<400> SEQUENCE: 62

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Ala Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300
```

Leu His Glu Gly Leu His Asn His His Thr Glu Lys Ser Leu Ser His
305 310 315 320

Ser Pro Gly Lys

<210> SEQ ID NO 63
<211> LENGTH: 330
<212> TYPE: PRT
<213> ORGANISM: Artificial Sequence
<220> FEATURE:
<223> OTHER INFORMATION: Mouse HC IgG2 constant domain

<400> SEQUENCE: 63

Ala Lys Thr Thr Ala Pro Ser Val Tyr Pro Leu Ala Pro Val Cys Gly
1 5 10 15

Asp Thr Thr Gly Ser Ser Val Thr Leu Gly Cys Leu Val Lys Gly Tyr
20 25 30

Phe Pro Glu Pro Val Thr Leu Thr Trp Asn Ser Gly Ser Leu Ser Ser
35 40 45

Gly Val His Thr Phe Pro Ala Val Leu Gln Ser Asp Leu Tyr Thr Leu
50 55 60

Ser Ser Ser Val Thr Val Thr Ser Ser Thr Trp Pro Ser Gln Ser Ile
65 70 75 80

Thr Cys Asn Val Ala His Pro Ala Ser Ser Thr Lys Val Asp Lys Lys
85 90 95

Ile Glu Pro Arg Gly Pro Thr Ile Lys Pro Cys Pro Pro Cys Lys Cys
100 105 110

Pro Ala Pro Asn Leu Leu Gly Gly Pro Ser Val Phe Ile Phe Pro Pro
115 120 125

Lys Ile Lys Asp Val Leu Met Ile Ser Leu Ser Pro Ile Val Thr Cys
130 135 140

Val Val Val Asp Val Ser Glu Asp Asp Pro Asp Val Gln Ile Ser Trp
145 150 155 160

Phe Val Asn Asn Val Glu Val His Thr Ala Gln Thr Gln Thr His Arg
165 170 175

Glu Asp Tyr Asn Ser Thr Leu Arg Val Val Ser Ala Leu Pro Ile Gln
180 185 190

His Gln Asp Trp Met Ser Gly Lys Glu Phe Lys Cys Lys Val Asn Asn
195 200 205

Lys Asp Leu Pro Ala Pro Ile Glu Arg Thr Ile Ser Lys Pro Lys Gly
210 215 220

Ser Val Arg Ala Pro Gln Val Tyr Val Leu Pro Pro Pro Glu Glu Glu
225 230 235 240

Met Thr Lys Lys Gln Val Thr Leu Thr Cys Met Val Thr Asp Phe Met
245 250 255

Pro Glu Asp Ile Tyr Val Glu Trp Thr Asn Asn Gly Lys Thr Glu Leu
260 265 270

Asn Tyr Lys Asn Thr Glu Pro Val Leu Asp Ser Asp Gly Ser Tyr Phe
275 280 285

Met Tyr Ser Lys Leu Arg Val Glu Lys Lys Asn Trp Val Glu Arg Asn
290 295 300

Ser Tyr Ser Cys Ser Val Val His Glu Gly Leu His Asn His His Thr
305 310 315 320

Thr Lys Ser Phe Ser Arg Thr Pro Gly Lys
325 330

<210> SEQ ID NO 64
<211> LENGTH: 107
<212> TYPE: PRT
<213> ORGANISM: Artificial Sequence
<220> FEATURE:
<223> OTHER INFORMATION: Mouse LC kappa constant domain

<400> SEQUENCE: 64

```
Arg Thr Val Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 65
<211> LENGTH: 375
<212> TYPE: DNA
<213> ORGANISM: Artificial Sequence
<220> FEATURE:
<223> OTHER INFORMATION: Nucleotide sequence encoding VH1

<400> SEQUENCE: 65

```
caggtgcagc tggtgcagag cggcgccgag gtgaagaagc ccggcgccag cgtgaaggtg     60

agctgcaagg ccagcggcta caccttcacc aactacggca tcagctgggt gagacaggcc    120

cccggccagg gcctggagtg gatgggctgg atcagcgcct acaacggcaa caccaactac    180

gcccagaagc tgcagggcag agtgaccatg accaccgaca ccagcaccag caccgcctac    240

atggagctga gaagcctgag aagcgacgac accgccgtgt actactgcgc cagagagggc    300

gcctacggct acagaagccc ctaccacaac tggttcgacc cctggggcca gggcaccctg    360

gtgaccgtga gcagc                                                     375
```

<210> SEQ ID NO 66
<211> LENGTH: 375
<212> TYPE: DNA
<213> ORGANISM: Artificial Sequence
<220> FEATURE:
<223> OTHER INFORMATION: Nucleotide sequence encoding VH2

<400> SEQUENCE: 66

```
gaggtgcagc tggtgcagag cggcgccgag gtgaagaagc ccggcgccag cgtgaaggtg     60

agctgcaagg ccagcggcta caccttcttc aagtacggca tcagctgggt gagacaggcc    120

cccggccagg gcctggagtg gatgggcagc atcagcccct acaccggcga gacccactac    180

gcccagaagc tgcagggcag agtgaccatg accaccgaca ccagcaccag caccgcctac    240

atggagctga gaagcctgag aagcgacgac accgccgtgt actactgcgc cagagagggc    300

gcctacggct acagaagccc ctaccagaac tggttcgacc cctggggcca gggcaccctg    360

gtgaccgtga gcagc                                                     375
```

-continued

<210> SEQ ID NO 67
<211> LENGTH: 321
<212> TYPE: DNA
<213> ORGANISM: Artificial Sequence
<220> FEATURE:
<223> OTHER INFORMATION: Nucleotide sequence encoding VL

<400> SEQUENCE: 67
gagatcgtga tgacccagag ccccgccacc ctgagcctga gccccggcga gagagccacc 60
ctgagctgca gagccagcca gagcgtgagc agctacctgg cctggtacca gcagaagccc 120
ggccaggccc ccagactgct gatctacgac gccagcaaca gagccaccgg catccccgcc 180
agattcagcg gcagcggcag cggcaccgac ttcaccctga ccatcagcag cctggagccc 240
gaggacttcg ccgtgtacta ctgccagcag cacagcctgc tgcccagaac cttcggcggc 300
ggcaccaagg tggagatcaa g 321

<210> SEQ ID NO 68
<211> LENGTH: 990
<212> TYPE: DNA
<213> ORGANISM: Artificial Sequence
<220> FEATURE:
<223> OTHER INFORMATION: Nucleotide sequence encoding human IgG1 HC
constant domain

<400> SEQUENCE: 68
gccagcacca agggccccag cgtgttcccc ctggccccca gcagcaagag caccagcggc 60
ggcaccgccg ccctgggctg cctggtgaag gactacttcc ccgagcccgt gaccgtgagc 120
tggaacagcg gcgccctgac cagcggcgtg cacaccttcc ccgccgtgct gcagagcagc 180
ggcctgtaca gcctgagcag cgtggtgacc gtgcccagca gcagcctggg cacccagacc 240
tacatctgca acgtgaacca caagcccagc aacaccaagg tggacaagaa ggtggagccc 300
aagagctgcg acaagaccca cacctgcccc ccctgccccg cccccgagct gctgggcggc 360
cccagcgtgt tcctgttccc ccccaagccc aaggacaccc tgatgatcag cagaaccccc 420
gaggtgacct gcgtggtggt ggacgtgagc cacgaggacc ccgaggtgaa gttcaactgg 480
tacgtggacg gcgtggaggt gcacaacgcc aagaccaagc ccagagagga gcagtacaac 540
agcacctaca gagtggtgag cgtgctgacc gtgctgcacc aggactggct gaacggcaag 600
gagtacaagt gcaaggtgag caacaaggcc ctgcccgccc ccatcgagaa gaccatcagc 660
aaggccaagg gccagcccag agagccccag gtgtacaccc tgccccccag cagagacgag 720
ctgaccaaga accaggtgag cctgacctgc ctggtgaagg gcttctaccc cagcgacatc 780
gccgtggagt gggagagcaa cggccagccc gagaacaact acaagaccac cccccccgtg 840
ctggacagcg acggcagctt cttcctgtac agcaagctga ccgtggacaa gagcagatgg 900
cagcagggca acgtgttcag ctgcagcgtg atgcacgagg ccctgcacaa ccactacacc 960
cagaagagcc tgagcctgag ccccggcaag 990

<210> SEQ ID NO 69
<211> LENGTH: 990
<212> TYPE: DNA
<213> ORGANISM: Artificial Sequence
<220> FEATURE:
<223> OTHER INFORMATION: Nucleotide sequence encoding human IgG1 HC
Constant domain (L234A L235A D265S)

<400> SEQUENCE: 69
gccagcacca agggccccag cgtgttcccc ctggccccca gcagcaagag caccagcggc 60
ggcaccgccg ccctgggctg cctggtgaag gactacttcc ccgagcccgt gaccgtgagc 120
tggaacagcg gcgccctgac cagcggcgtg cacaccttcc ccgccgtgct gcagagcagc 180
ggcctgtaca gcctgagcag cgtggtgacc gtgcccagca gcagcctggg cacccagacc 240
tacatctgca acgtgaacca caagcccagc aacaccaagg tggacaagaa ggtggagccc 300
aagagctgcg acaagaccca cacctgcccc ccctgccccg cccccgaggc cgccggcggc 360
cccagcgtgt tcctgttccc ccccaagccc aaggacaccc tgatgatcag cagaaccccc 420
gaggtgacct gcgtggtggt gagcgtgagc cacgaggacc ccgaggtgaa gttcaactgg 480
tacgtggacg gcgtggaggt gcacaacgcc aagaccaagc ccagagagga gcagtacaac 540
agcacctaca gagtggtgag cgtgctgacc gtgctgcacc aggactggct gaacggcaag 600
gagtacaagt gcaaggtgag caacaaggcc ctgcccgccc ccatcgagaa gaccatcagc 660
aaggccaagg gccagcccag agagccccag gtgtacaccc tgcccccag cagagacgag 720
ctgaccaaga accaggtgag cctgacctgc ctggtgaagg gcttctaccc cagcgacatc 780
gccgtggagt gggagagcaa cggccagccc gagaacaact acaagaccac cccccccgtg 840
ctggacagcg acggcagctt cttcctgtac agcaagctga ccgtggacaa gagcagatgg 900
cagcagggca acgtgttcag ctgcagcgtg atgcacgagg ccctgcacaa ccactacacc 960
cagaagagcc tgagcctgag ccccggcaag 990

<210> SEQ ID NO 70
<211> LENGTH: 990
<212> TYPE: DNA
<213> ORGANISM: Artificial Sequence
<220> FEATURE:
<223> OTHER INFORMATION: Nucleotide sequence encoding human IgG1 HC
Constant domain (L234A L235A P329G)

<400> SEQUENCE: 70
gccagcacca agggccccag cgtgttcccc ctggccccca gcagcaagag caccagcggc 60
ggcaccgccg ccctgggctg cctggtgaag gactacttcc ccgagcccgt gaccgtgagc 120
tggaacagcg gcgccctgac cagcggcgtg cacaccttcc ccgccgtgct gcagagcagc 180
ggcctgtaca gcctgagcag cgtggtgacc gtgcccagca gcagcctggg cacccagacc 240
tacatctgca acgtgaacca caagcccagc aacaccaagg tggacaagaa ggtggagccc 300
aagagctgcg acaagaccca cacctgcccc ccctgccccg cccccgaggc cgccggcggc 360
cccagcgtgt tcctgttccc ccccaagccc aaggacaccc tgatgatcag cagaaccccc 420
gaggtgacct gcgtggtggt gagcgtgagc cacgaggacc ccgaggtgaa gttcaactgg 480
tacgtggacg gcgtggaggt gcacaacgcc aagaccaagc ccagagagga gcagtacaac 540
agcacctaca gagtggtgag cgtgctgacc gtgctgcacc aggactggct gaacggcaag 600
gagtacaagt gcaaggtgag caacaaggcc ctgggcgccc ccatcgagaa gaccatcagc 660
aaggccaagg gccagcccag agagccccag gtgtacaccc tgcccccag cagagacgag 720
ctgaccaaga accaggtgag cctgacctgc ctggtgaagg gcttctaccc cagcgacatc 780
gccgtggagt gggagagcaa cggccagccc gagaacaact acaagaccac cccccccgtg 840
ctggacagcg acggcagctt cttcctgtac agcaagctga ccgtggacaa gagcagatgg 900

```
cagcagggca acgtgttcag ctgcagcgtg atgcacgagg ccctgcacaa ccactacacc    960

cagaagagcc tgagcctgag ccccggcaag                                     990


<210> SEQ ID NO 71
<211> LENGTH: 990
<212> TYPE: DNA
<213> ORGANISM: Artificial Sequence
<220> FEATURE:
<223> OTHER INFORMATION: Nucleotide sequence encoding human IgG1 HC
      Constant domain (L235E)

<400> SEQUENCE: 71

gccagcacca agggccccag cgtgttcccc ctggccccca gcagcaagag caccagcggc     60

ggcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcagcctggg cacccagacc    240

tacatctgca acgtgaacca caagcccagc aacaccaagg tggacaagaa ggtggagccc    300

aagagctgcg acaagaccca cacctgcccc ccctgccccg cccccgagct ggagggcggc    360

cccagcgtgt tcctgttccc ccccaagccc aaggacaccc tgatgatcag cagaaccccc    420

gaggtgacct gcgtggtggt ggacgtgagc cacgaggacc ccgaggtgaa gttcaactgg    480

tacgtggacg gcgtggaggt gcacaacgcc aagaccaagc ccagagagga gcagtacaac    540

agcacctaca gagtggtgag cgtgctgacc gtgctgcacc aggactggct gaacggcaag    600

gagtacaagt gcaaggtgag caacaaggcc ctgcccgccc ccatcgagaa gaccatcagc    660

aaggccaagg gccagcccag agagccccag gtgtacaccc tgccccccag cagagacgag    720

ctgaccaaga accaggtgag cctgacctgc ctggtgaagg gcttctaccc cagcgacatc    780

gccgtggagt gggagagcaa cggccagccc gagaacaact acaagaccac cccccccgtg    840

ctggacagcg acggcagctt cttcctgtac agcaagctga ccgtggacaa gagcagatgg    900

cagcagggca acgtgttcag ctgcagcgtg atgcacgagg ccctgcacaa ccactacacc    960

cagaagagcc tgagcctgag ccccggcaag                                     990


<210> SEQ ID NO 72
<211> LENGTH: 990
<212> TYPE: DNA
<213> ORGANISM: Artificial Sequence
<220> FEATURE:
<223> OTHER INFORMATION: Nucleotide sequence encoding human IgG1 HC
      Constant domain (D265A)

<400> SEQUENCE: 72

gccagcacca agggccccag cgtgttcccc ctggccccca gcagcaagag caccagcggc     60

ggcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcagcctggg cacccagacc    240

tacatctgca acgtgaacca caagcccagc aacaccaagg tggacaagaa ggtggagccc    300

aagagctgcg acaagaccca cacctgcccc ccctgccccg cccccgagct gctgggcggc    360

cccagcgtgt tcctgttccc ccccaagccc aaggacaccc tgatgatcag cagaaccccc    420

gaggtgacct gcgtggtggt ggccgtgagc cacgaggacc ccgaggtgaa gttcaactgg    480

tacgtggacg gcgtggaggt gcacaacgcc aagaccaagc ccagagagga gcagtacaac    540
```

-continued

```
agcacctaca gagtggtgag cgtgctgacc gtgctgcacc aggactggct gaacggcaag    600

gagtacaagt gcaaggtgag caacaaggcc ctgcccgccc ccatcgagaa gaccatcagc    660

aaggccaagg gccagcccag agagccccag gtgtacaccc tgcccccccag cagagacgag    720

ctgaccaaga accaggtgag cctgacctgc ctggtgaagg gcttctaccc cagcgacatc    780

gccgtggagt gggagagcaa cggccagccc gagaacaact acaagaccac cccccccgtg    840

ctggacagcg acggcagctt cttcctgtac agcaagctga ccgtggacaa gagcagatgg    900

cagcagggca acgtgttcag ctgcagcgtg atgcacgagg ccctgcacaa ccactacacc    960

cagaagagcc tgagcctgag ccccggcaag                                    990
```

```
<210> SEQ ID NO 73
<211> LENGTH: 990
<212> TYPE: DNA
<213> ORGANISM: Artificial Sequence
<220> FEATURE:
<223> OTHER INFORMATION: Nucleotide sequence encoding human IgG1 HC
      Constant domain (D265A N297G)

<400> SEQUENCE: 73

gccagcacca agggccccag cgtgttcccc ctggccccca gcagcaagag caccagcggc     60

ggcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcagcctggg cacccagacc    240

tacatctgca acgtgaacca caagcccagc aacaccaagg tggacaagaa ggtggagccc    300

aagagctgcg acaagaccca cacctgcccc ccctgccccg cccccgagct gctgggcggc    360

cccagcgtgt tcctgttccc ccccaagccc aaggacaccc tgatgatcag cagaaccccc    420

gaggtgacct gcgtggtggt ggccgtgagc cacgaggacc ccgaggtgaa gttcaactgg    480

tacgtggacg gcgtggaggt gcacaacgcc aagaccaagc ccagagagga gcagtacggc    540

agcacctaca gagtggtgag cgtgctgacc gtgctgcacc aggactggct gaacggcaag    600

gagtacaagt gcaaggtgag caacaaggcc ctgcccgccc ccatcgagaa gaccatcagc    660

aaggccaagg gccagcccag agagccccag gtgtacaccc tgcccccccag cagagacgag    720

ctgaccaaga accaggtgag cctgacctgc ctggtgaagg gcttctaccc cagcgacatc    780

gccgtggagt gggagagcaa cggccagccc gagaacaact acaagaccac cccccccgtg    840

ctggacagcg acggcagctt cttcctgtac agcaagctga ccgtggacaa gagcagatgg    900

cagcagggca acgtgttcag ctgcagcgtg atgcacgagg ccctgcacaa ccactacacc    960

cagaagagcc tgagcctgag ccccggcaag                                    990
```

```
<210> SEQ ID NO 74
<211> LENGTH: 990
<212> TYPE: DNA
<213> ORGANISM: Artificial Sequence
<220> FEATURE:
<223> OTHER INFORMATION: Nucleotide sequence encoding human IgG1 HC
      Constant domain (E233A/L235A)

<400> SEQUENCE: 74

gccagcacca agggccccag cgtgttcccc ctggccccca gcagcaagag caccagcggc     60

ggcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcagcctggg cacccagacc    240
```

```
tacatctgca acgtgaacca caagcccagc aacaccaagg tggacaagaa ggtggagccc    300

aagagctgcg acaagaccca cacctgcccc ccctgccccg cccccgccct ggccggcggc    360

cccagcgtgt tcctgttccc ccccaagccc aaggacaccc tgatgatcag cagaaccccc    420

gaggtgacct gcgtggtggt ggacgtgagc cacgaggacc ccgaggtgaa gttcaactgg    480

tacgtggacg gcgtggaggt gcacaacgcc aagaccaagc ccagagagga gcagtacaac    540

agcacctaca gagtggtgag cgtgctgacc gtgctgcacc aggactggct gaacggcaag    600

gagtacaagt gcaaggtgag caacaaggcc ctgcccgccc ccatcgagaa gaccatcagc    660

aaggccaagg gccagcccag agagccccag gtgtacaccc tgccccccag cagagacgag    720

ctgaccaaga accaggtgag cctgacctgc ctggtgaagg gcttctaccc cagcgacatc    780

gccgtggagt gggagagcaa cggccagccc gagaacaact acaagaccac cccccccgtg    840

ctggacagcg acggcagctt cttcctgtac agcaagctga ccgtggacaa gagcagatgg    900

cagcagggca acgtgttcag ctgcagcgtg atgcacgagg ccctgcacaa ccactacacc    960

cagaagagcc tgagcctgag ccccggcaag                                      990
```

```
<210> SEQ ID NO 75
<211> LENGTH: 990
<212> TYPE: DNA
<213> ORGANISM: Artificial Sequence
<220> FEATURE:
<223> OTHER INFORMATION: Nucleotide sequence encoding human IgG1 HC
      Constant domain (N297X, wherein X is any amino acid other than N)
<220> FEATURE:
<221> NAME/KEY: misc_feature
<222> LOCATION: (538)..(540)
<223> OTHER INFORMATION: Codon wherein each N is any nucleotide with the
      proviso that the codon does not encode Asn or form a translation
      stop codon

<400> SEQUENCE: 75

gccagcacca agggccccag cgtgttcccc ctggccccca gcagcaagag caccagcggc     60

ggcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcagcctggg cacccagacc    240

tacatctgca acgtgaacca caagcccagc aacaccaagg tggacaagaa ggtggagccc    300

aagagctgcg acaagaccca cacctgcccc ccctgccccg cccccgagct gctgggcggc    360

cccagcgtgt tcctgttccc ccccaagccc aaggacaccc tgatgatcag cagaaccccc    420

gaggtgacct gcgtggtggt ggacgtgagc cacgaggacc ccgaggtgaa gttcaactgg    480

tacgtggacg gcgtggaggt gcacaacgcc aagaccaagc ccagagagga gcagtacnnn    540

agcacctaca gagtggtgag cgtgctgacc gtgctgcacc aggactggct gaacggcaag    600

gagtacaagt gcaaggtgag caacaaggcc ctgcccgccc ccatcgagaa gaccatcagc    660

aaggccaagg gccagcccag agagccccag gtgtacaccc tgccccccag cagagacgag    720

ctgaccaaga accaggtgag cctgacctgc ctggtgaagg gcttctaccc cagcgacatc    780

gccgtggagt gggagagcaa cggccagccc gagaacaact acaagaccac cccccccgtg    840

ctggacagcg acggcagctt cttcctgtac agcaagctga ccgtggacaa gagcagatgg    900

cagcagggca acgtgttcag ctgcagcgtg atgcacgagg ccctgcacaa ccactacacc    960

cagaagagcc tgagcctgag ccccggcaag                                      990
```

```
<210> SEQ ID NO 76
<211> LENGTH: 978
<212> TYPE: DNA
<213> ORGANISM: Artificial Sequence
<220> FEATURE:
<223> OTHER INFORMATION: Nucleotide sequence encoding human IgG2 HC
      Constant domain

<400> SEQUENCE: 76

gccagcacca agggccccag cgtgttcccc ctggccccct gcagcagaag caccagcgag     60

agcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcaacttcgg cacccagacc    240

tacacctgca acgtggacca caagcccagc aacaccaagg tggacaagac cgtggagaga    300

aagtgctgcg tggagtgccc cccctgcccc gccccccccg tggccggccc cagcgtgttc    360

ctgttccccc ccaagcccaa ggacaccctg atgatcagca gaacccccga ggtgacctgc    420

gtggtggtgg acgtgagcca cgaggacccc gaggtgcagt tcaactggta cgtggacggc    480

gtggaggtgc acaacgccaa gaccaagccc agagaggagc agttcaacag caccttcaga    540

gtggtgagcg tgctgaccgt ggtgcaccag gactggctga acggcaagga gtacaagtgc    600

aaggtgagca acaagggcct gcccgccccc atcgagaaga ccatcagcaa gaccaagggc    660

cagcccagag agccccaggt gtacaccctg ccccccagca gagaggagat gaccaagaac    720

caggtgagcc tgacctgcct ggtgaagggc ttctacccca gcgacatcag cgtggagtgg    780

gagagcaacg gccagcccga gaacaactac aagaccaccc cccccatgct ggacagcgac    840

ggcagcttct tcctgtacag caagctgacc gtggacaaga gcagatggca gcagggcaac    900

gtgttcagct gcagcgtgat gcacgaggcc ctgcacaacc actacaccca gaagagcctg    960

agcctgagcc ccggcaag                                                  978


<210> SEQ ID NO 77
<211> LENGTH: 978
<212> TYPE: DNA
<213> ORGANISM: Artificial Sequence
<220> FEATURE:
<223> OTHER INFORMATION: Nucleotide sequence encoding human IgG2 HC
      Constant domain (D265S)

<400> SEQUENCE: 77

gccagcacca agggccccag cgtgttcccc ctggccccct gcagcagaag caccagcgag     60

agcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcaacttcgg cacccagacc    240

tacacctgca acgtggacca caagcccagc aacaccaagg tggacaagac cgtggagaga    300

aagtgctgcg tggagtgccc cccctgcccc gccccccccg tggccggccc cagcgtgttc    360

ctgttccccc ccaagcccaa ggacaccctg atgatcagca gaacccccga ggtgacctgc    420

gtggtggtga gcgtgagcca cgaggacccc gaggtgcagt tcaactggta cgtggacggc    480

gtggaggtgc acaacgccaa gaccaagccc agagaggagc agttcaacag caccttcaga    540

gtggtgagcg tgctgaccgt ggtgcaccag gactggctga acggcaagga gtacaagtgc    600

aaggtgagca acaagggcct gcccgccccc atcgagaaga ccatcagcaa gaccaagggc    660

cagcccagag agccccaggt gtacaccctg ccccccagca gagaggagat gaccaagaac    720
```

```
caggtgagcc tgacctgcct ggtgaagggc ttctacccca gcgacatcag cgtggagtgg    780

gagagcaacg gccagcccga gaacaactac aagaccaccc cccccatgct ggacagcgac    840

ggcagcttct tcctgtacag caagctgacc gtggacaaga gcagatggca gcagggcaac    900

gtgttcagct gcagcgtgat gcacgaggcc ctgcacaacc actacaccca gaagagcctg    960

agcctgagcc ccggcaag                                                  978
```

<210> SEQ ID NO 78
<211> LENGTH: 978
<212> TYPE: DNA
<213> ORGANISM: Artificial Sequence
<220> FEATURE:
<223> OTHER INFORMATION: Nucleotide sequence encoding human IgG2 HC
Constant domain (P329G)

<400> SEQUENCE: 78

```
gccagcacca agggccccag cgtgttcccc ctggccccct gcagcagaag caccagcgag     60

agcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcaacttcgg cacccagacc    240

tacacctgca acgtggacca caagcccagc aacaccaagg tggacaagac cgtggagaga    300

aagtgctgcg tggagtgccc cccctgcccc gccccccccg tggccggccc cagcgtgttc    360

ctgttccccc ccaagcccaa ggacaccctg atgatcagca gaacccccga ggtgacctgc    420

gtggtggtgg acgtgagcca cgaggacccc gaggtgcagt tcaactggta cgtggacggc    480

gtggaggtgc acaacgccaa gaccaagccc agagaggagc agttcaacag caccttcaga    540

gtggtgagcg tgctgaccgt ggtgcaccag gactggctga acggcaagga gtacaagtgc    600

aaggtgagca acaagggcct gggcgccccc atcgagaaga ccatcagcaa gaccaagggc    660

cagcccagag agccccaggt gtacaccctg ccccccagca gagaggagat gaccaagaac    720

caggtgagcc tgacctgcct ggtgaagggc ttctacccca gcgacatcag cgtggagtgg    780

gagagcaacg gccagcccga gaacaactac aagaccaccc cccccatgct ggacagcgac    840

ggcagcttct tcctgtacag caagctgacc gtggacaaga gcagatggca gcagggcaac    900

gtgttcagct gcagcgtgat gcacgaggcc ctgcacaacc actacaccca gaagagcctg    960

agcctgagcc ccggcaag                                                  978
```

<210> SEQ ID NO 79
<211> LENGTH: 978
<212> TYPE: DNA
<213> ORGANISM: Artificial Sequence
<220> FEATURE:
<223> OTHER INFORMATION: Nucleotide sequence encoding human IgG2 HC
Constant domain (D265A)

<400> SEQUENCE: 79

```
gccagcacca agggccccag cgtgttcccc ctggccccct gcagcagaag caccagcgag     60

agcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcaacttcgg cacccagacc    240

tacacctgca acgtggacca caagcccagc aacaccaagg tggacaagac cgtggagaga    300

aagtgctgcg tggagtgccc cccctgcccc gccccccccg tggccggccc cagcgtgttc    360

ctgttccccc ccaagcccaa ggacaccctg atgatcagca gaacccccga ggtgacctgc    420
```

```
gtggtggtgg ccgtgagcca cgaggacccc gaggtgcagt tcaactggta cgtggacggc    480

gtggaggtgc acaacgccaa gaccaagccc agagaggagc agttcaacag caccttcaga    540

gtggtgagcg tgctgaccgt ggtgcaccag gactggctga acggcaagga gtacaagtgc    600

aaggtgagca acaagggcct gcccgccccc atcgagaaga ccatcagcaa gaccaagggc    660

cagcccagag agccccaggt gtacaccctg ccccccagca gagaggagat gaccaagaac    720

caggtgagcc tgacctgcct ggtgaagggc ttctacccca gcgacatcag cgtggagtgg    780

gagagcaacg gccagcccga gaacaactac aagaccaccc cccccatgct ggacagcgac    840

ggcagcttct tcctgtacag caagctgacc gtggacaaga gcagatggca gcagggcaac    900

gtgttcagct gcagcgtgat gcacgaggcc ctgcacaacc actacaccca gaagagcctg    960

agcctgagcc ccggcaag                                                  978
```

<210> SEQ ID NO 80
<211> LENGTH: 978
<212> TYPE: DNA
<213> ORGANISM: Artificial Sequence
<220> FEATURE:
<223> OTHER INFORMATION: Nucleotide sequence encoding human IgG2 HC
Constant domain (D265A N297G)

<400> SEQUENCE: 80

```
gccagcacca agggccccag cgtgttcccc ctggccccct gcagcagaag caccagcgag     60

agcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcaacttcgg cacccagacc    240

tacacctgca acgtggacca caagcccagc aacaccaagg tggacaagac cgtggagaga    300

aagtgctgcg tggagtgccc cccctgcccc gcccccccccg tggccggccc cagcgtgttc    360

ctgttccccc ccaagcccaa ggacaccctg atgatcagca gaacccccga ggtgacctgc    420

gtggtggtgg ccgtgagcca cgaggacccc gaggtgcagt tcaactggta cgtggacggc    480

gtggaggtgc acaacgccaa gaccaagccc agagaggagc agttcggcag caccttcaga    540

gtggtgagcg tgctgaccgt ggtgcaccag gactggctga acggcaagga gtacaagtgc    600

aaggtgagca acaagggcct gcccgccccc atcgagaaga ccatcagcaa gaccaagggc    660

cagcccagag agccccaggt gtacaccctg ccccccagca gagaggagat gaccaagaac    720

caggtgagcc tgacctgcct ggtgaagggc ttctacccca gcgacatcag cgtggagtgg    780

gagagcaacg gccagcccga gaacaactac aagaccaccc cccccatgct ggacagcgac    840

ggcagcttct tcctgtacag caagctgacc gtggacaaga gcagatggca gcagggcaac    900

gtgttcagct gcagcgtgat gcacgaggcc ctgcacaacc actacaccca gaagagcctg    960

agcctgagcc ccggcaag                                                  978
```

<210> SEQ ID NO 81
<211> LENGTH: 978
<212> TYPE: DNA
<213> ORGANISM: Artificial Sequence
<220> FEATURE:
<223> OTHER INFORMATION: Nucleotide sequence encoding human IgG2 HC
Constant domain (N297X, wherein X is any amino acid other than N)
<220> FEATURE:
<221> NAME/KEY: misc_feature
<222> LOCATION: (526)..(528)

<223> OTHER INFORMATION: Codon wherein each N is any nucleotide with the proviso that the codon does not encode Asn or form a translation stop codon

<400> SEQUENCE: 81

```
gccagcacca agggccccag cgtgttcccc ctggcccccct gcagcagaag caccagcgag     60

agcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcaacttcgg cacccagacc    240

tacacctgca acgtggacca caagcccagc aacaccaagg tggacaagac cgtggagaga    300

aagtgctgcg tggagtgccc cccctgcccc gcccccccccg tggccggccc cagcgtgttc    360

ctgttccccc ccaagcccaa ggacaccctg atgatcagca gaacccccga ggtgacctgc    420

gtggtggtgg acgtgagcca cgaggacccc gaggtgcagt tcaactggta cgtggacggc    480

gtggaggtgc acaacgccaa gaccaagccc agagaggagc agttcnnnag caccttcaga    540

gtggtgagcg tgctgaccgt ggtgcaccag gactggctga acggcaagga gtacaagtgc    600

aaggtgagca acaagggcct gcccgccccc atcgagaaga ccatcagcaa gaccaagggc    660

cagcccagag agccccaggt gtacaccctg ccccccagca gagaggagat gaccaagaac    720

caggtgagcc tgacctgcct ggtgaagggc ttctacccca gcgacatcag cgtggagtgg    780

gagagcaacg gccagcccga gaacaactac aagaccaccc cccccatgct ggacagcgac    840

ggcagcttct tcctgtacag caagctgacc gtggacaaga gcagatggca gcagggcaac    900

gtgttcagct gcagcgtgat gcacgaggcc ctgcacaacc actacaccca gaagagcctg    960

agcctgagcc ccggcaag                                                  978
```

<210> SEQ ID NO 82
<211> LENGTH: 978
<212> TYPE: DNA
<213> ORGANISM: Artificial Sequence
<220> FEATURE:
<223> OTHER INFORMATION: Nucleotide sequence encoding human IgG2 HC Constant domain (V234A G237A P238S H268A V309L A330S P331S X378S/A)
<220> FEATURE:
<221> NAME/KEY: misc_feature
<222> LOCATION: (769)..(771)
<223> OTHER INFORMATION: n is a, c, g, or t

<400> SEQUENCE: 82

```
gccagcacca agggccccag cgtgttcccc ctggcccccct gcagcagaag caccagcgag     60

agcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcaacttcgg cacccagacc    240

tacacctgca acgtggacca caagcccagc aacaccaagg tggacaagac cgtggagaga    300

aagtgctgcg tggagtgccc cccctgcccc gcccccccccg ccgccgccag cagcgtgttc    360

ctgttccccc ccaagcccaa ggacaccctg atgatcagca gaacccccga ggtgacctgc    420

gtggtggtgg acgtgagcgc cgaggacccc gaggtgcagt tcaactggta cgtggacggc    480

gtggaggtgc acaacgccaa gaccaagccc agagaggagc agttcaacag caccttcaga    540

gtggtgagcg tgctgaccgt gctgcaccag gactggctga acggcaagga gtacaagtgc    600

aaggtgagca acaagggcct gcccagcagc atcgagaaga ccatcagcaa gaccaagggc    660

cagcccagag agccccaggt gtacaccctg ccccccagca gagaggagat gaccaagaac    720
```

caggtgagcc tgacctgcct ggtgaagggc ttctacccca gcgacatcnn ngtggagtgg 780
gagagcaacg gccagcccga gaacaactac aagaccaccc cccccatgct ggacagcgac 840
ggcagcttct tcctgtacag caagctgacc gtggacaaga gcagatggca gcagggcaac 900
gtgttcagct gcagcgtgat gcacgaggcc ctgcacaacc actacaccca gaagagcctg 960
agcctgagcc ccggcaag 978

<210> SEQ ID NO 83
<211> LENGTH: 981
<212> TYPE: DNA
<213> ORGANISM: Artificial Sequence
<220> FEATURE:
<223> OTHER INFORMATION: Nucleotide sequence encoding human IgG4 HC
Constant domain (S228P)

<400> SEQUENCE: 83
gccagcacca agggccccag cgtgttcccc ctggccccct gcagcagaag caccagcgag 60
agcaccgccg ccctgggctg cctggtgaag gactacttcc ccgagcccgt gaccgtgagc 120
tggaacagcg gcgccctgac cagcggcgtg cacaccttcc ccgccgtgct gcagagcagc 180
ggcctgtaca gcctgagcag cgtggtgacc gtgcccagca gcagcctggg caccaagacc 240
tacacctgca acgtggacca caagcccagc aacaccaagg tggacaagag agtggagagc 300
aagtacggcc ccccctgccc ccctgcccc gcccccgagt tcctgggcgg ccccagcgtg 360
ttcctgttcc cccccaagcc caaggacacc ctgatgatca gcagaacccc cgaggtgacc 420
tgcgtggtgg tggacgtgag ccaggaggac cccgaggtgc agttcaactg gtacgtggac 480
ggcgtggagg tgcacaacgc caagaccaag cccagagagg agcagttcaa cagcacctac 540
agagtggtga gcgtgctgac cgtgctgcac caggactggc tgaacggcaa ggagtacaag 600
tgcaaggtga gcaacaaggg cctgcccagc agcatcgaga agaccatcag caaggccaag 660
ggccagccca gagagcccca ggtgtacacc ctgcccccca gccaggagga gatgaccaag 720
aaccaggtga gcctgacctg cctggtgaag ggcttctacc ccagcgacat cgccgtggag 780
tgggagagca acggccagcc cgagaacaac tacaagacca ccccccccgt gctggacagc 840
gacggcagct tcttcctgta cagcagactg accgtggaca agagcagatg gcaggagggc 900
aacgtgttca gctgcagcgt gatgcacgag gccctgcaca accactacac ccagaagagc 960
ctgagcctga gcctgggcaa g 981

<210> SEQ ID NO 84
<211> LENGTH: 960
<212> TYPE: DNA
<213> ORGANISM: Artificial Sequence
<220> FEATURE:
<223> OTHER INFORMATION: Nucleotide sequence encoding human IgG4 HC
Constant domain (S228P P329G)

<400> SEQUENCE: 84
gccagcacca agggccccag cgtgttcccc ctggccccct gcagcagaag caccagcgag 60
agcaccgccg ccctgggctg cctggtgaag gactacttcc ccgagcccgt gaccgtgagc 120
tggaacagcg gcgccctgac cagcggcgtg cacaccttcc ccgccgtgct gcagagcagc 180
ggcctgtaca gcctgagcag cgtggtgacc gtgcccagca gcagcctggg caccaagacc 240
tacacctgca acgtggacca caagcccagc aacaccaagg tggacaagag agtggagagc 300
aagtacggcc ccccctgccc ccctgcccc gcccccgagt tcctgggcgg ccccagcgtg 360

-continued

```
ttcctgttcc cccccaagcc caaggacacc ctgatgatca gcagaacccc cgaggtgacc    420

tgcgtggtgg tggacgtgag ccaggaggac cccgaggtgc agttcaactg gtacgtggac    480

ggcgtggagg tgcacaacgc caagaccaag cccagagagg agcagttcaa cagcacctac    540

agagtggtga gcgtgctgac cgtgctgcac caggactggc tgaacggcaa ggagtacaag    600

tgcaaggtga gcaacaaggg cctgggcagc agcatcgaga agaccatcag caaggccaag    660

ggccagccca gagagcccca ggtgtacacc ctgcccccca gccaggagga gatgaccaag    720

aaccaggtga gcctgacctg cctggtgaag ggcttctacc ccagcgacat cgccgtggag    780

tgggagagca acggccagcc cgagaacaac tacaagacca cccccccgt gctggacagc    840

gacggcagct tcttcctgta cagcagactg accgtggaca agagcagatg gcaggagggc    900

aacgtgttca gctgcagcgt gatgcacgag gccctgcaca accactacac ccagaagagc    960
```

```
<210> SEQ ID NO 85
<211> LENGTH: 981
<212> TYPE: DNA
<213> ORGANISM: Artificial Sequence
<220> FEATURE:
<223> OTHER INFORMATION: Nucleotide sequence encoding human IgG4 HC
      Constant domain (S228P D265A)

<400> SEQUENCE: 85

gccagcacca agggccccag cgtgttcccc ctggccccct gcagcagaag caccagcgag     60

agcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcagcctggg caccaagacc    240

tacacctgca acgtggacca caagcccagc aacaccaagg tggacaagag agtggagagc    300

aagtacggcc cccccgcccc cccctgcccc gcccccgagt tcctgggcgg ccccagcgtg    360

ttcctgttcc cccccaagcc caaggacacc ctgatgatca gcagaacccc cgaggtgacc    420

tgcgtggtgg tggccgtgag ccaggaggac cccgaggtgc agttcaactg gtacgtggac    480

ggcgtggagg tgcacaacgc caagaccaag cccagagagg agcagttcaa cagcacctac    540

agagtggtga gcgtgctgac cgtgctgcac caggactggc tgaacggcaa ggagtacaag    600

tgcaaggtga gcaacaaggg cctgcccagc agcatcgaga agaccatcag caaggccaag    660

ggccagccca gagagcccca ggtgtacacc ctgcccccca gccaggagga gatgaccaag    720

aaccaggtga gcctgacctg cctggtgaag ggcttctacc ccagcgacat cgccgtggag    780

tgggagagca acggccagcc cgagaacaac tacaagacca cccccccgt gctggacagc    840

gacggcagct tcttcctgta cagcagactg accgtggaca agagcagatg gcaggagggc    900

aacgtgttca gctgcagcgt gatgcacgag gccctgcaca accactacac ccagaagagc    960

ctgagcctga gcctgggcaa g                                              981
```

```
<210> SEQ ID NO 86
<211> LENGTH: 981
<212> TYPE: DNA
<213> ORGANISM: Artificial Sequence
<220> FEATURE:
<223> OTHER INFORMATION: Nucleotide sequence encoding human IgG4 HC
      Constant domain (S228P D265A N297G)

<400> SEQUENCE: 86

gccagcacca agggccccag cgtgttcccc ctggccccct gcagcagaag caccagcgag     60

agcaccgccg ccctgggctg cctggtgaag gactacttcc ccgagcccgt gaccgtgagc    120
```

```
tggaacagcg gcgccctgac cagcggcgtg cacaccttcc ccgccgtgct gcagagcagc    180

ggcctgtaca gcctgagcag cgtggtgacc gtgcccagca gcagcctggg caccaagacc    240

tacacctgca acgtggacca caagcccagc aacaccaagg tggacaagag agtggagagc    300

aagtacggcc ccccctgccc cccctgcccc gcccccgagt tcctgggcgg ccccagcgtg    360

ttcctgttcc cccccaagcc caaggacacc ctgatgatca gcagaacccc cgaggtgacc    420

tgcgtggtgg tggccgtgag ccaggaggac cccgaggtgc agttcaactg gtacgtggac    480

ggcgtggagg tgcacaacgc caagaccaag cccagagagg agcagttcgg cagcacctac    540

agagtggtga gcgtgctgac cgtgctgcac caggactggc tgaacggcaa ggagtacaag    600

tgcaaggtga gcaacaaggg cctgcccagc agcatcgaga agaccatcag caaggccaag    660

ggccagccca gagagcccca ggtgtacacc ctgcccccca gccaggagga gatgaccaag    720

aaccaggtga gcctgacctg cctggtgaag ggcttctacc ccagcgacat cgccgtggag    780

tgggagagca acggccagcc cgagaacaac tacaagacca ccccccccgt gctggacagc    840

gacggcagct tcttcctgta cagcagactg accgtggaca agagcagatg gcaggagggc    900

aacgtgttca gctgcagcgt gatgcacgag gccctgcaca accactacac ccagaagagc    960

ctgagcctga gcctgggcaa g                                              981
```

<210> SEQ ID NO 87
<211> LENGTH: 981
<212> TYPE: DNA
<213> ORGANISM: Artificial Sequence
<220> FEATURE:
<223> OTHER INFORMATION: Nucleotide sequence encoding human IgG4 HC Constant domain (S228P N297X, wherein X is any amino acid other than N)
<220> FEATURE:
<221> NAME/KEY: misc_feature
<222> LOCATION: (529)..(531)
<223> OTHER INFORMATION: Codon wherein each N is any nucleotide with the proviso that the codon does not encode Asn or form a translation stop codon

<400> SEQUENCE: 87

```
gccagcacca agggccccag cgtgttcccc ctggccccct gcagcagaag caccagcgag     60

agcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcagcctggg caccaagacc    240

tacacctgca acgtggacca caagcccagc aacaccaagg tggacaagag agtggagagc    300

aagtacggcc ccccctgccc cccctgcccc gcccccgagt tcctgggcgg ccccagcgtg    360

ttcctgttcc cccccaagcc caaggacacc ctgatgatca gcagaacccc cgaggtgacc    420

tgcgtggtgg tggacgtgag ccaggaggac cccgaggtgc agttcaactg gtacgtggac    480

ggcgtggagg tgcacaacgc caagaccaag cccagagagg agcagttcnn nagcacctac    540

agagtggtga gcgtgctgac cgtgctgcac caggactggc tgaacggcaa ggagtacaag    600

tgcaaggtga gcaacaaggg cctgcccagc agcatcgaga agaccatcag caaggccaag    660

ggccagccca gagagcccca ggtgtacacc ctgcccccca gccaggagga gatgaccaag    720

aaccaggtga gcctgacctg cctggtgaag ggcttctacc ccagcgacat cgccgtggag    780

tgggagagca acggccagcc cgagaacaac tacaagacca ccccccccgt gctggacagc    840

gacggcagct tcttcctgta cagcagactg accgtggaca agagcagatg gcaggagggc    900
```

-continued

```
aacgtgttca gctgcagcgt gatgcacgag gccctgcaca accactacac ccagaagagc    960

ctgagcctga gcctgggcaa g                                               981


<210> SEQ ID NO 88
<211> LENGTH: 321
<212> TYPE: DNA
<213> ORGANISM: Artificial Sequence
<220> FEATURE:
<223> OTHER INFORMATION: Nucleotide sequence encoding human LC Kappa
      Constant domain

<400> SEQUENCE: 88

agaaccgtgg ccgcccccag cgtgttcatc ttcccccca gcgacgagca gctgaagagc      60

ggcaccgcca gcgtggtgtg cctgctgaac aacttctacc ccagagaggc caaggtgcag    120

tggaaggtgg acaacgccct gcagagcggc aacagccagg agagcgtgac cgagcaggac    180

agcaaggaca gcacctacag cctgagcagc accctgaccc tgagcaaggc cgactacgag    240

aagcacaagg tgtacgcctg cgaggtgacc caccagggcc tgagcagccc cgtgaccaag    300

agcttcaaca gaggcgagtg c                                               321


<210> SEQ ID NO 89
<211> LENGTH: 990
<212> TYPE: DNA
<213> ORGANISM: Artificial Sequence
<220> FEATURE:
<223> OTHER INFORMATION: Nucleotide sequence encoding human IgG1 HC
      Constant domain (N297A/D356E/L358M)

<400> SEQUENCE: 89

gccagcacca agggccccag cgtgttcccc ctggccccca gcagcaagag caccagcggc     60

ggcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcagcctggg cacccagacc    240

tacatctgca acgtgaacca caagcccagc aacaccaagg tggacaagaa ggtggagccc    300

aagagctgcg acaagaccca cacctgcccc ccctgccccg cccccgagct gctgggcggc    360

cccagcgtgt tcctgttccc ccccaagccc aaggacaccc tgatgatcag cagaaccccc    420

gaggtgacct gcgtggtggt ggacgtgagc cacgaggacc ccgaggtgaa gttcaactgg    480

tacgtggacg gcgtggaggt gcacaacgcc aagaccaagc ccagagagga gcagtacgcc    540

agcacctaca gagtggtgag cgtgctgacc gtgctgcacc aggactggct gaacggcaag    600

gagtacaagt gcaaggtgag caacaaggcc ctgcccgccc ccatcgagaa gaccatcagc    660

aaggccaagg gccagcccag agagccccag gtgtacaccc tgccccccag cagagaggag    720

atgaccaaga accaggtgag cctgacctgc ctggtgaagg gcttctaccc cagcgacatc    780

gccgtggagt gggagagcaa cggccagccc gagaacaact acaagaccac cccccccgtg    840

ctggacagcg acggcagctt cttcctgtac agcaagctga ccgtggacaa gagcagatgg    900

cagcagggca acgtgttcag ctgcagcgtg atgcacgagg ccctgcacaa ccactacacc    960

cagaagagcc tgagcctgag ccccggcaag                                      990


<210> SEQ ID NO 90
<211> LENGTH: 951
<212> TYPE: DNA
<213> ORGANISM: Artificial Sequence
```

<220> FEATURE:
<223> OTHER INFORMATION: Nucleotide sequence encoding human IgG1 HC
      Constant domain (L234F/L235E/P331S/D356E/L358M)

<400> SEQUENCE: 90

```
gccagcacca agggccccag cgtgttcccc ctggcccccct gcagcagaag caccagcgag     60

agcaccgccg ccctgggctg cctggtgaag gactacttcc ccgagcccgt gaccgtgagc    120

tggaacagcg gcgccctgac cagcggcgtg cacaccttcc ccgccgtgct gcagagcagc    180

ggcctgtaca gcctgagcag cgtggtgacc gtgcccagca gcagcctggg caccaagacc    240

tacacctgca acgtggacca caagcccagc aacaccaagg tggacaagag agtggagagc    300

aagtacggcc cccctgccc cccctgcccc gcccccgagt tcctgggcgg ccccagcgtg    360

ttcctgttcc cccccaagcc caaggacacc ctgatgatca gcagaacccc cgaggtgacc    420

tgcgtggtgg tggacgtgag ccaggaggac cccgaggtgc agttcaactg gtacgtggac    480

ggcgtggagg tgcacaacgc caagaccaag cccagagagg agcagttcaa cagcacctac    540

agagtggtga gcgtgctgac cgtgctgcac caggactggc tgaacggcaa ggagtacaag    600

tgcaaggtga gcaacaaggg cctgcccagc agcatcgaga agaccatcag caaggccaag    660

ggccagccca gagagcccca ggtgtacacc ctgcccccca gcctgacctg cctggtgaag    720

ggcttctacc ccagcgacat cgccgtggag tgggagagca acggccagcc cgagaacaac    780

tacaagacca cccccccgt gctggacagc gacggcagct tcttcctgta cagcagactg    840

accgtggaca agagcagatg gcaggagggc aacgtgttca gctgcagcgt gatgcacgag    900

gccctgcaca accactacac ccagaagagc ctgagcctga gcctgggcaa g             951
```

<210> SEQ ID NO 91
<211> LENGTH: 318
<212> TYPE: DNA
<213> ORGANISM: Artificial Sequence
<220> FEATURE:
<223> OTHER INFORMATION: Nucleotide sequence encoding human LC lambda
      Constant domain

<400> SEQUENCE: 91

```
ggccagccca aggccaaccc caccgtgacc ctgttccccc ccagcagcga ggagctgcag     60

gccaacaagg ccaccctggt gtgcctgatc agcgacttct accccggcgc cgtgaccgtg    120

gcctggaagg ccgacggcag ccccgtgaag gccggcgtgg agaccaccaa gcccagcaag    180

cagagcaaca acaagtacgc cgccagcagc tacctgagcc tgacccccga gcagtggaag    240

agccacagaa gctacagctg ccaggtgacc cacgagggca gcaccgtgga gaagaccgtg    300

gcccccaccg agtgcagc                                                  318
```

<210> SEQ ID NO 92
<211> LENGTH: 972
<212> TYPE: DNA
<213> ORGANISM: Artificial Sequence
<220> FEATURE:
<223> OTHER INFORMATION: Nucleotide sequence encoding mouse HC IgG1
      (D265A) constant domain

<400> SEQUENCE: 92

```
gccaagacca cccccccag cgtgtacccc ctggcccccg gcagcgccgc ccagaccaac     60

agcatggtga ccctgggctg cctggtgaag ggctacttcc ccgagcccgt gaccgtgacc    120

tggaacagcg gcagcctgag cagcggcgtg cacaccttcc ccgccgtgct gcagagcgac    180

ctgtacaccc tgagcagcag cgtgaccgtg cccagcagca cctggcccag cgagaccgtg    240
```

-continued acctgcaacg tggcccaccc cgccagcagc accaaggtgg acaagaagat cgtgcccaga 300
gactgcggct gcaagccctg catctgcacc gtgcccgagg tgagcagcgt gttcatcttc 360
ccccccaagc ccaaggacgt gctgaccatc accctgaccc ccaaggtgac ctgcgtggtg 420
gtggccatca gcaaggacga ccccgaggtg cagttcagct ggttcgtgga cgacgtggag 480
gtgcacaccg cccagaccca gcccagagag gagcagttca acagcacctt cagaagcgtg 540
agcgagctgc ccatcatgca ccaggactgg ctgaacggca aggagttcaa gtgcagagtg 600
aacagcgccg ccttccccgc ccccatcgag aagaccatca gcaagaccaa gggcagaccc 660
aaggcccccc aggtgtacac catccccccc cccaaggagc agatggccaa ggacaaggtg 720
agcctgacct gcatgatcac cgacttcttc cccgaggaca tcaccgtgga gtggcagtgg 780
aacggccagc ccgccgagaa ctacaagaac acccagccca tcatggacac cgacggcagc 840
tacttcgtgt acagcaagct gaacgtgcag aagagcaact gggaggccgg caacaccttc 900
acctgcagcg tgctgcacga gggcctgcac aaccaccaca ccgagaagag cctgagccac 960
agccccggca ag 972

<210> SEQ ID NO 93
<211> LENGTH: 990
<212> TYPE: DNA
<213> ORGANISM: Artificial Sequence
<220> FEATURE:
<223> OTHER INFORMATION: Nucleotide sequence encoding mouse HC IgG2
constant domain

<400> SEQUENCE: 93
gccaagacca ccgcccccag cgtgtacccc ctggcccccg tgtgcggcga caccaccggc 60
agcagcgtga ccctgggctg cctggtgaag ggctacttcc ccgagcccgt gaccctgacc 120
tggaacagcg gcagcctgag cagcggcgtg cacaccttcc ccgccgtgct gcagagcgac 180
ctgtacaccc tgagcagcag cgtgaccgtg accagcagca cctggcccag ccagagcatc 240
acctgcaacg tggcccaccc cgccagcagc accaaggtgg acaagaagat cgagcccaga 300
ggccccacca tcaagccctg ccccccctgc aagtgccccg cccccaacct gctgggcggc 360
cccagcgtgt tcatcttccc ccccaagatc aaggacgtgc tgatgatcag cctgagcccc 420
atcgtgacct gcgtggtggt ggacgtgagc gaggacgacc ccgacgtgca gatcagctgg 480
ttcgtgaaca acgtggaggt gcacaccgcc cagacccaga cccacagaga ggactacaac 540
agcaccctga gagtggtgag cgccctgccc atccagcacc aggactggat gagcggcaag 600
gagttcaagt gcaaggtgaa caacaaggac ctgcccgccc ccatcgagag aaccatcagc 660
aagcccaagg gcagcgtgag agcccccccag gtgtacgtgc tgcccccccc cgaggaggag 720
atgaccaaga agcaggtgac cctgacctgc atggtgaccg acttcatgcc cgaggacatc 780
tacgtggagt ggaccaacaa cggcaagacc gagctgaact acaagaacac cgagcccgtg 840
ctggacagcg acggcagcta cttcatgtac agcaagctga gagtggagaa gaagaactgg 900
gtggagagaa acagctacag ctgcagcgtg gtgcacgagg gcctgcacaa ccaccacacc 960
accaagagct tcagcagaac ccccggcaag 990

<210> SEQ ID NO 94
<211> LENGTH: 321
<212> TYPE: DNA
<213> ORGANISM: Artificial Sequence -continued
<220> FEATURE:
<223> OTHER INFORMATION: Nucleotide sequence encoding mouse LC kappa
      constant domain

<400> SEQUENCE: 94
agaaccgtgg ccgcccccac cgtgagcatc ttccccccca gcagcgagca gctgaccagc     60
ggcggcgcca gcgtggtgtg cttcctgaac aacttctacc ccaaggacat caacgtgaag    120
tggaagatcg acggcagcga gagacagaac ggcgtgctga acagctggac cgaccaggac    180
agcaaggaca gcacctacag catgagcagc accctgaccc tgaccaagga cgagtacgag    240
agacacaaca gctacacctg cgaggccacc cacaagacca gcaccagccc catcgtgaag    300
agcttcaaca gaaacgagtg c                                              321

<210> SEQ ID NO 95
<211> LENGTH: 20
<212> TYPE: PRT
<213> ORGANISM: Artificial Sequence
<220> FEATURE:
<223> OTHER INFORMATION: Leader peptide A

<400> SEQUENCE: 95

Met Ser Val Pro Thr Gln Val Leu Gly Leu Leu Leu Leu Trp Leu Thr
1               5                   10                  15

Asp Ala Arg Cys
            20

<210> SEQ ID NO 96
<211> LENGTH: 19
<212> TYPE: PRT
<213> ORGANISM: Artificial Sequence
<220> FEATURE:
<223> OTHER INFORMATION: Leader peptide B

<400> SEQUENCE: 96

Met Glu Trp Ser Trp Val Phe Leu Phe Phe Leu Ser Val Thr Thr Gly
1               5                   10                  15

Val His Ser

<210> SEQ ID NO 97
<211> LENGTH: 60
<212> TYPE: DNA
<213> ORGANISM: Artificial Sequence
<220> FEATURE:
<223> OTHER INFORMATION: Nucleotide sequence encoding leader peptide A

<400> SEQUENCE: 97
atgagcgtgc ccacccaggt gctgggcctg ctgctgctgt ggctgaccga cgccagatgc     60

<210> SEQ ID NO 98
<211> LENGTH: 57
<212> TYPE: DNA
<213> ORGANISM: Artificial Sequence
<220> FEATURE:
<223> OTHER INFORMATION: Nucleotide sequence encoding leader peptide B

<400> SEQUENCE: 98
atggagtgga gctgggtgtt cctgttcttc ctgagcgtga ccaccggcgt gcacagc        57